US008152821B2

(12) United States Patent
Gambale et al.

(10) Patent No.: US 8,152,821 B2
(45) Date of Patent: Apr. 10, 2012

(54) ENDOSCOPIC TISSUE APPOSITION DEVICE WITH MULTIPLE SUCTION PORTS

(75) Inventors: Richard A. Gambale, Tyngsboro, MA (US); Michael F. Weiser, Groton, MA (US); Edward C. Page, Baldwinville, MA (US); Peter J. Lukin, Lancaster, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 1029 days.

(21) Appl. No.: 12/070,809

(22) Filed: Feb. 21, 2008

(65) Prior Publication Data

US 2008/0215069 A1   Sep. 4, 2008

Related U.S. Application Data

(63) Continuation of application No. 10/220,379, filed as application No. PCT/US01/06835 on Mar. 24, 2003, now Pat. No. 7,399,304.

(60) Provisional application No. 60/186,771, filed on Mar. 3, 2000, provisional application No. 60/186,650, filed on Mar. 3, 2000, provisional application No. 60/187,275, filed on Mar. 6, 2000.

(51) Int. Cl.
*A61B 17/10* (2006.01)
*A61B 17/04* (2006.01)

(52) U.S. Cl. .................................. 606/139; 606/144

(58) Field of Classification Search .................. 606/139, 606/144, 148–150, 153, 159, 213, 215, 216, 606/219, 221; 112/169; 227/175.1
See application file for complete search history.

(56) References Cited

U.S. PATENT DOCUMENTS

| 3,868,448 | A | 2/1975 | Hahn et al. |
| 4,133,315 | A | 1/1979 | Berman et al. |
| 4,246,893 | A | 1/1981 | Berson |
| 4,403,604 | A | 9/1983 | Wilkinson et al. |
| 4,416,267 | A | 11/1983 | Garren et al. |

(Continued)

FOREIGN PATENT DOCUMENTS

EP   0 571 938 A2   12/1993
(Continued)

OTHER PUBLICATIONS

Awan, A., et al., "Endoscopic Vertical Band Gastroplasty with an Endoscopic Sewing Machine", Gastrointestinal Endoscopy (2002) pp. 254-256, vol. 55, No. 2.

(Continued)

*Primary Examiner* — Julian Woo
(74) *Attorney, Agent, or Firm* — Wolf, Greenfield & Sacks, P.C.

(57) ABSTRACT

The present invention relates to an improved endoscopic tissue apposition device having multiple suction ports. The invention permits multiple folds of tissue to be captured in the suction ports with a single positioning of the device and attached together by a tissue securement mechanism such as a suture, staple or other form of tissue bonding. The improvement reduces the number of intubations required during an endoscopic procedure to suture tissue or join areas of tissue together. The suction ports may be arranged in a variety of configurations on the apposition device to best suit the desired resulting tissue orientation. The inventive tissue apposition device may also incorporate tissue abrasion means to activate the healing process on surfaces of tissue areas that are to be joined by operation of the device to promote a more secure attachment by permanent tissue bonding.

10 Claims, 35 Drawing Sheets

U.S. PATENT DOCUMENTS

| | | | |
|---|---|---|---|
| 4,739,758 A | 4/1988 | Lai et al. | |
| 4,899,747 A | 2/1990 | Garren et al. | |
| 5,037,021 A * | 8/1991 | Mills et al. | 227/175.1 |
| 5,080,663 A * | 1/1992 | Mills et al. | 606/139 |
| 5,084,061 A | 1/1992 | Gau et al. | |
| 5,250,053 A | 10/1993 | Snyder | |
| 5,259,399 A | 11/1993 | Brown | |
| 5,327,914 A | 7/1994 | Shlain | |
| 5,474,565 A | 12/1995 | Trott | |
| 5,562,689 A | 10/1996 | Green et al. | |
| 5,571,116 A | 11/1996 | Bolanos et al. | |
| 5,665,376 A | 9/1997 | Russo | |
| 5,792,153 A | 8/1998 | Swain et al. | |
| 5,868,141 A | 2/1999 | Ellias | |
| 5,868,760 A | 2/1999 | McGuckin | |
| 5,887,594 A | 3/1999 | LoCicero, III | |
| 5,938,668 A | 8/1999 | Scirica et al. | |
| 5,977,175 A | 11/1999 | Lin | |
| 6,009,877 A | 1/2000 | Edwards | |
| 6,044,846 A | 4/2000 | Edwards | |
| 6,092,528 A | 7/2000 | Edwards | |
| 6,102,922 A | 8/2000 | Jakobsson et al. | |
| 6,139,555 A | 10/2000 | Hart et al. | |
| 6,234,955 B1 | 5/2001 | Silverman et al. | |
| 6,238,335 B1 | 5/2001 | Silverman et al. | |
| 6,248,058 B1 | 6/2001 | Silverman et al. | |
| 6,251,063 B1 | 6/2001 | Silverman et al. | |
| 6,251,064 B1 | 6/2001 | Silverman et al. | |
| 6,398,795 B1 | 6/2002 | McAlister et al. | |
| 6,427,089 B1 | 7/2002 | Knowlton | |
| 6,447,533 B1 | 9/2002 | Adams | |
| 6,494,888 B1 | 12/2002 | Laufer et al. | |
| 6,530,878 B2 | 3/2003 | Silverman et al. | |
| 6,533,717 B2 | 3/2003 | Silverman et al. | |
| 6,540,789 B2 | 4/2003 | Silverman | |
| 6,543,456 B1 | 4/2003 | Freeman | |
| 6,558,400 B2 | 5/2003 | Deem et al. | |
| 6,572,629 B2 | 6/2003 | Kalloo et al. | |
| 6,575,896 B2 | 6/2003 | Silverman et al. | |
| 6,592,596 B1 | 7/2003 | Geitz | |
| 6,595,909 B2 | 7/2003 | Silverman et al. | |
| 6,595,910 B2 | 7/2003 | Silverman et al. | |
| 6,608,029 B1 | 8/2003 | Kolterman et al. | |
| 6,627,206 B2 | 9/2003 | Lloyd | |
| 6,663,639 B1 | 12/2003 | Laufer et al. | |
| 6,675,809 B2 | 1/2004 | Stack et al. | |
| 6,712,814 B2 | 3/2004 | Edwards et al. | |
| 6,716,222 B2 | 4/2004 | McAlister et al. | |
| 6,749,607 B2 | 6/2004 | Edwards et al. | |
| 6,758,219 B2 | 7/2004 | Sapala et al. | |
| 6,773,440 B2 | 8/2004 | Gannoe | |
| 6,773,441 B1 | 8/2004 | Laufer et al. | |
| 6,845,776 B2 | 1/2005 | Stack et al. | |
| 6,846,312 B2 | 1/2005 | Edwards et al. | |
| 6,858,576 B1 | 2/2005 | Young et al. | |
| 6,955,643 B2 | 10/2005 | Gellman | |
| 6,997,931 B2 | 2/2006 | Sauer | |
| 7,037,315 B2 | 5/2006 | Sancoff et al. | |
| 7,037,344 B2 | 5/2006 | Kagan et al. | |
| 7,083,630 B2 | 8/2006 | DeVries et al. | |
| 7,090,684 B2 | 8/2006 | McGuckin et al. | |
| 7,125,413 B2 | 10/2006 | Grigoryants | |
| 7,175,638 B2 | 2/2007 | Gannoe et al. | |
| 7,204,842 B2 | 4/2007 | Geitz | |
| 7,229,428 B2 | 6/2007 | Gannoe | |
| 2001/0011543 A1 | 8/2001 | Forsell et al. | |
| 2002/0022851 A1 | 2/2002 | Kalloo et al. | |
| 2002/0055750 A1 | 5/2002 | Durgin et al. | |
| 2002/0065523 A1 | 5/2002 | McAlister et al. | |
| 2002/0082616 A1 | 6/2002 | McAlister et al. | |
| 2002/0107530 A1 | 8/2002 | Sauer et al. | |
| 2002/0115991 A1 | 8/2002 | Edwards | |
| 2002/0139379 A1 | 10/2002 | Edwards et al. | |
| 2002/0143346 A1 | 10/2002 | McGuckin et al. | |
| 2002/0169357 A1 | 11/2002 | Chen | |
| 2002/0183765 A1 | 12/2002 | Adams | |
| 2002/0183768 A1 | 12/2002 | Deem et al. | |
| 2002/0193816 A1 | 12/2002 | Laufer et al. | |
| 2003/0009165 A1 | 1/2003 | Edwards et al. | |
| 2003/0021822 A1 | 1/2003 | Lloyd | |
| 2003/0109892 A1 | 6/2003 | Deem et al. | |
| 2003/0113310 A1 | 6/2003 | Van Laere et al. | |
| 2003/0158601 A1 | 8/2003 | Silverman et al. | |
| 2003/0188755 A1 | 10/2003 | Milbocker | |
| 2003/0208209 A1 | 11/2003 | Gambale et al. | |
| 2003/0233108 A1 | 12/2003 | Gellman et al. | |
| 2003/0236536 A1 | 12/2003 | Grigoryants et al. | |
| 2004/0006351 A1 | 1/2004 | Gannoe et al. | |
| 2004/0039452 A1 | 2/2004 | Bessler | |
| 2004/0044353 A1 | 3/2004 | Gannoe | |
| 2004/0044354 A1 | 3/2004 | Gannoe et al. | |
| 2004/0059289 A1 | 3/2004 | Alvarez | |
| 2004/0082963 A1 | 4/2004 | Gannoe et al. | |
| 2004/0087977 A1 | 5/2004 | Nolan et al. | |
| 2004/0092892 A1 | 5/2004 | Kagan et al. | |
| 2004/0097415 A1 | 5/2004 | Kolterman et al. | |
| 2004/0097986 A1 | 5/2004 | Adams | |
| 2004/0097989 A1 | 5/2004 | Trigueros | |
| 2004/0116949 A1 | 6/2004 | Ewers et al. | |
| 2004/0117031 A1 | 6/2004 | Stack et al. | |
| 2004/0122456 A1 | 6/2004 | Saadat et al. | |
| 2004/0122473 A1 | 6/2004 | Ewers et al. | |
| 2004/0133147 A1 | 7/2004 | Woo et al. | |
| 2004/0158263 A1 | 8/2004 | McAlister et al. | |
| 2004/0162567 A9 | 8/2004 | Adams | |
| 2004/0162568 A1 | 8/2004 | Saadat et al. | |
| 2004/0167546 A1 | 8/2004 | Saadat | |
| 2004/0193190 A1 | 9/2004 | Liddicoat et al. | |
| 2004/0194157 A1 | 9/2004 | Meguid | |
| 2004/0194790 A1 | 10/2004 | Laufer et al. | |
| 2004/0199180 A1 | 10/2004 | Knodel et al. | |
| 2004/0210243 A1 | 10/2004 | Gannoe et al. | |
| 2004/0220682 A1 | 11/2004 | Levine et al. | |
| 2004/0225183 A1 | 11/2004 | Michlitsch et al. | |
| 2004/0225305 A1 | 11/2004 | Ewers | |
| 2004/0236356 A1 | 11/2004 | Rioux et al. | |
| 2004/0258621 A1 | 12/2004 | Stern | |
| 2004/0267378 A1 | 12/2004 | Gazi | |
| 2005/0022827 A1 | 2/2005 | Woo et al. | |
| 2005/0033319 A1 | 2/2005 | Gambale et al. | |
| 2005/0033320 A1 | 2/2005 | McGuckin et al. | |
| 2005/0043817 A1 | 2/2005 | McKenna | |
| 2005/0049614 A1 | 3/2005 | Cendan | |
| 2005/0055038 A1 | 3/2005 | Kelleher et al. | |
| 2005/0065536 A1 | 3/2005 | Ewers et al. | |
| 2005/0075653 A1 | 4/2005 | Saadat et al. | |
| 2005/0080444 A1 | 4/2005 | Kramer et al. | |
| 2005/0090837 A1 | 4/2005 | Sixto et al. | |
| 2005/0119671 A1 | 6/2005 | Reydel et al. | |
| 2005/0119674 A1 | 6/2005 | Gingras | |
| 2005/0143760 A1 | 6/2005 | Imran | |
| 2005/0149067 A1 | 7/2005 | Takemoto et al. | |
| 2005/0149072 A1 | 7/2005 | DeVries et al. | |
| 2005/0149200 A1 | 7/2005 | Silverman et al. | |
| 2005/0171556 A1 | 8/2005 | Murphy | |
| 2005/0177176 A1 | 8/2005 | Gerbi et al. | |
| 2005/0216036 A1 | 9/2005 | Nakao | |
| 2005/0251162 A1 | 11/2005 | Rothe et al. | |
| 2005/0256587 A1 | 11/2005 | Egan | |
| 2006/0020277 A1 | 1/2006 | Gostout et al. | |
| 2006/0047289 A1 | 3/2006 | Fogel | |
| 2006/0149316 A1 | 7/2006 | DeVries et al. | |
| 2006/0212053 A1 | 9/2006 | Gertner | |
| 2006/0282087 A1 | 12/2006 | Binmoeller | |
| 2007/0055292 A1 | 3/2007 | Ortiz et al. | |
| 2007/0129735 A1 | 6/2007 | Filipi et al. | |
| 2007/0167963 A1 | 7/2007 | Deem et al. | |
| 2007/0173931 A1 | 7/2007 | Tremulis et al. | |
| 2007/0175488 A1 | 8/2007 | Cox et al. | |

FOREIGN PATENT DOCUMENTS

| | | |
|---|---|---|
| EP | 1 397 998 A1 | 3/2004 |
| EP | 1 749 480 A1 | 2/2007 |
| EP | 1 749 482 A2 | 2/2007 |
| EP | 1 759 639 A1 | 3/2007 |
| WO | WO 93/20819 A1 | 10/1993 |
| WO | WO 95/25468 A1 | 9/1995 |

| | | | |
|---|---|---|---|
| WO | WO 99/35987 A1 | 7/1999 |
| WO | WO 99/60931 A1 | 12/1999 |
| WO | WO 00/48672 A1 | 8/2000 |
| WO | WO 01/66020 A2 | 9/2001 |
| WO | WO 02/060328 A1 | 8/2002 |
| WO | WO 02/096327 A2 | 12/2002 |
| WO | WO 2004/019765 A2 | 3/2004 |
| WO | WO 2004/021894 A1 | 3/2004 |
| WO | WO 2004/034973 A1 | 4/2004 |
| WO | WO 2004/069056 A1 | 8/2004 |
| WO | WO 2004/084808 A1 | 10/2004 |
| WO | WO 2004/112563 A2 | 12/2004 |
| WO | WO 2005/011463 A2 | 2/2005 |
| WO | WO 2005/011519 A2 | 2/2005 |
| WO | WO 2005/020802 A1 | 3/2005 |
| WO | WO 2005/037072 A1 | 4/2005 |
| WO | WO 2005/037152 A1 | 4/2005 |
| WO | WO 2005/039458 A2 | 5/2005 |
| WO | WO 2005/058239 A2 | 6/2005 |
| WO | WO 2007/019268 A2 | 2/2007 |
| WO | WO 2007/095096 A2 | 8/2007 |

OTHER PUBLICATIONS

Awan, A., et al., "Endoscopic Vertical Band Gastroplasty (VBG) with Outlet Ring Using Endoscopic Sewing Machine", Gastroenterology (Apr. 2000) vol. 118, No. 4, Suppl. 2, Abstract 4131.

Schwartz, R., et al., "Gastric Bypass Revision: Lessons Learned From 920 Cases", Surgery (Oct. 1988) pp. 806-812, vol. 104, No. 4.

Schweitzer, M., "Endoscopic Intraluminal Suture Plication of the Gastric Pouch and Stoma in Postoperative Roux-en-Y Gastric Bypass Patients", Journal of Laparoendoscopic & Advanced Surgical Techniques (2004) pp. 223-226, vol. 14, No. 4.

Spaulding, L., "Treatment of Dilated Gastrojejunostomy with Sclerotherapy", Obesity Surgery (2003) pp. 254-257, vol. 13.

Sugerman, H., "Bariatric Surgery for Severe Obesity", Journal of the Association for Academic Minority Physicians (Jul. 2001) pp. 129-136, vol. 12, No. 3.

European Examination Report dated Apr. 3, 2009, Applicant C.R. Bard, Inc., Application No. 01 913 282.8.

* cited by examiner

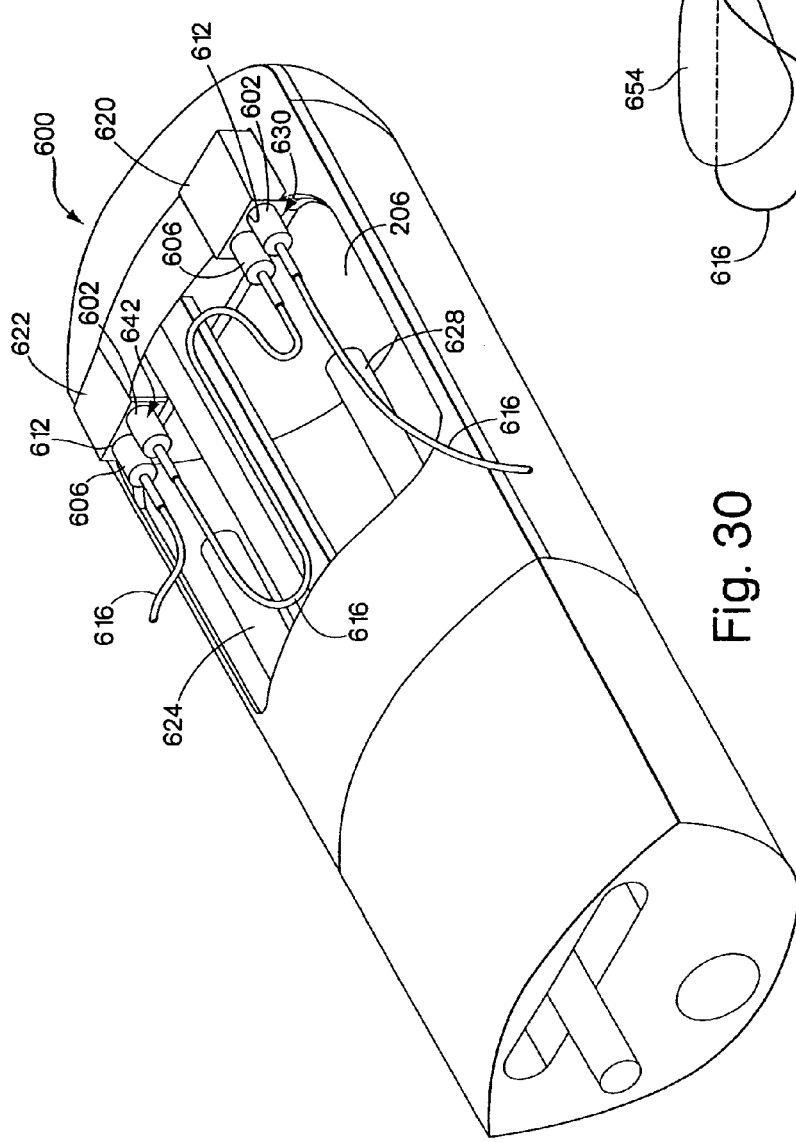

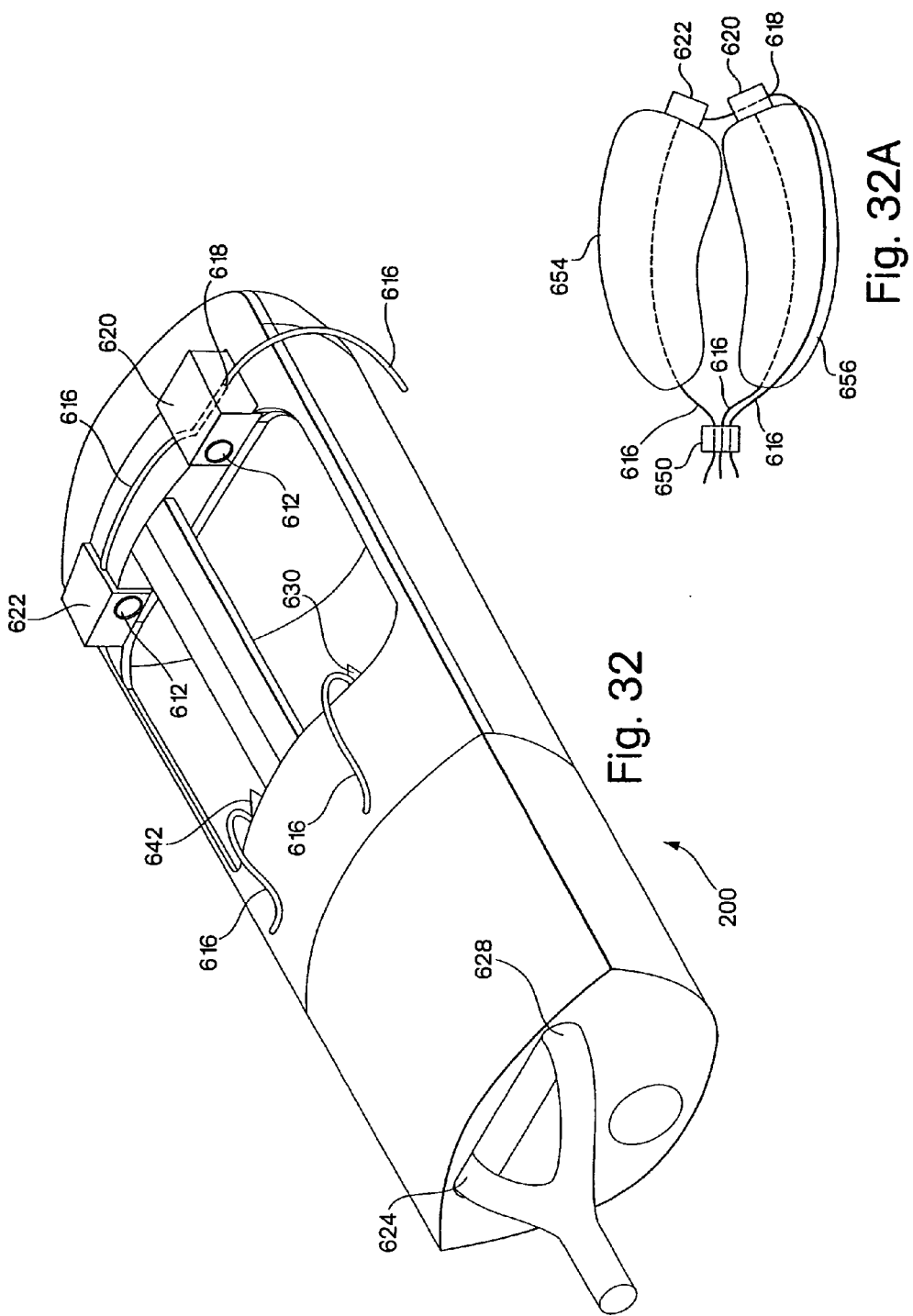

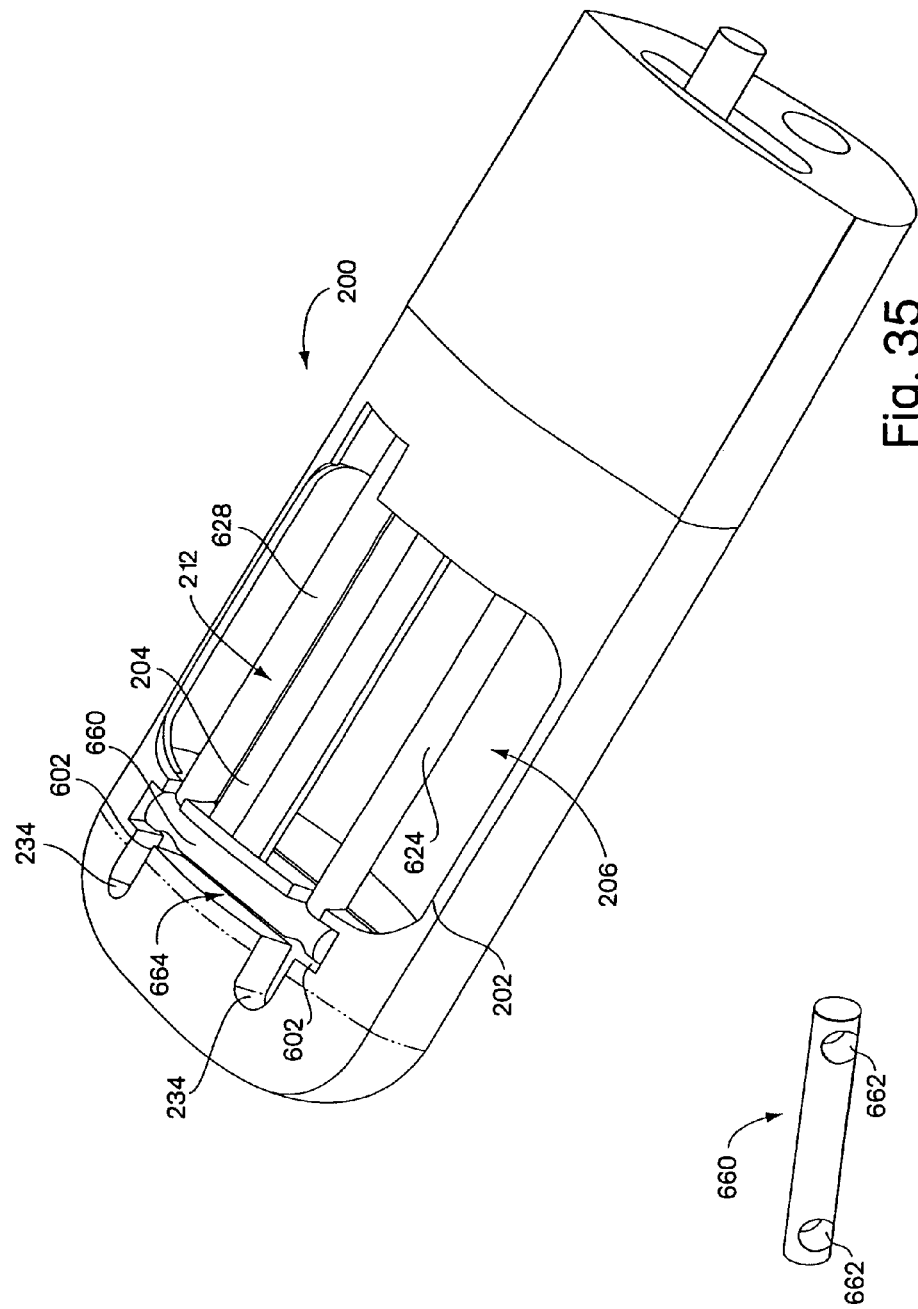
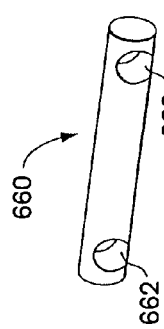

ENDOSCOPIC TISSUE APPOSITION DEVICE WITH MULTIPLE SUCTION PORTS

RELATED APPLICATIONS

This application is a continuation of U.S. application Ser. No. 10/220,379, filed Mar. 24, 2003, now U.S. Pat. No. 7,399,304 which is the U.S. National Stage of International Application No. PCT/US01/06835, filed Mar. 2, 2001, which claims the benefit to U.S. Provisional Applications Nos. 60/186,771, filed Mar. 3, 2000, 60/186,650, filed Mar. 3, 2000, and 60/187,275, filed Mar. 6, 2000, the entire contents of which are incorporated herein by reference.

FIELD OF THE INVENTION

The present invention relates to improvements for endoscopic tissue apposition devices. Specifically, the invention provides an endoscopic apposition device configured to collect a plurality of tissue portions with a single operation of the device so that the tissue can be joined together by a tissue securing means.

BACKGROUND OF THE INVENTION

Endoscopic apposition devices are devices that can be used in the body of a patient without the need to make an external incision in the patient, the device being controlled externally of the patient by endoscopic means. Apposition devices may comprise a sewing or stapling device for use in flexible endoscopy, though it is also applicable to devices for use in rigid endoscopy.

Endoscopic tissue apposition devices are useful to help perform a gastroplasty procedure to correct gastro-esophageal reflux disease (GERD). This condition results from the inability of the valve at the junction between the stomach and the esophagus to function properly. Such malfunction enables reflux of stomach acid into the esophagus. The object of the gastroplasty procedure is to stitch together certain portions of stomach tissue in a manner that forms a valve-like structure adapted to prevent such reflux.

To perform the procedure, an apposition device, such as a sewing capsule is attached to the end of a viewing endoscope and is inserted through a patient's esophagus to form a plurality of stitches in stomach tissue slightly below the lower end of the esophagus. A first stitch is made through stomach tissue to one side of the esophagus, and a second stitch is made, with the same suture thread, in stomach tissue adjacent to the first stitch. The two stitches then are drawn together to pull together the diametrically opposed, stitched stomach portions. In a preferred procedure, a tubular configuration having a somewhat figure-eight cross-sectional configuration is formed.

After the sutures are applied, the endoscope is removed from the patient and a knot is tied with the free ends of the suture thread that extend outside of the patient to maintain the figure-eight configuration. The knot is pushed down to the site of the sutures by the thread guide device that has been positioned at the distal end of the endoscope. To help navigate the knot to a location where it will effectively hold the tissue, it is helpful to view the knot through the viewing channel of the endoscope as it is guided to the stomach. To be visible through the endoscope, the knot must be maintained in front of the viewing channel port at the distal face of the endoscope, yet the structure of the thread guide device must not block the viewing channel.

The suturing and knotting procedure is repeated several times at longitudinally spaced intervals to create a plurality of figure-eight configurations extending longitudinally of the esophagus into the stomach. Suturing the stomach tissue in this manner essentially lengthens the esophageal passage and defines a structure having a valving action that is effective to prevent gastro-esophageal reflux. After a sufficient number of knots and sutures have been placed, a thread cutter, also operable through the endoscope, may be employed to cut the suture thread at points that are close to the tissue.

Endoscopic sewing devices are described in, for example, U.S. Pat. Nos. 5,080,663 and 5,792,153. Those patents disclose a sewing device for passing a thread through a tissue portion, which comprises a hollow needle movable between a first position in which it is out of the said tissue portion and a second position in which it passes through the said tissue portion, and a thread carrier adapted to be attached to the thread and being receivable within the hollow needle. The sewing device comprises a body, which defines a cavity within which the tissue portion can be held by means of suction, and the hollow needle is mounted for movement in the body between the first and second positions.

U.S. Pat. No. 5,792,153 discloses two suturing device embodiments: a single stitch sewing device and a multiple stitch sewing device. In the single stitch device, a thread carrier is transported by the needle through the tissue as the latter passes from its first position to its second position. When the needle returns to its first position, the thread carrier is left behind in the distal end of the sewing capsule. In the multiple stitch device, the same procedure occurs, but it is followed by a further step in which the hollow needle travels from its first position to its second position, picks up the thread carrier, and returns it. A second stitch may be formed during the next step. The whole sequence of steps is repeated as many times as may be required to form the desired number of stitches.

Minimizing the number of intubations and reducing the procedure time during which the patient must be kept under conscious sedation are important considerations in any endoscopic procedure. The prior art suturing device must be withdrawn from the patient for each successive stitch made with the single-stitch embodiment and must otherwise be repositioned for each stitch made with the multi-stitch embodiment. The use of the devices is, thus, long and cumbersome. It would be desirable to provide an endoscopic tissue apposition device that minimizes procedure time and the number of intubations while still joining the same number of tissue plications together during the procedure. The present invention endeavors to provide such an improvement with a multiple suction port tissue apposition device.

A variable in the success of keeping tissue joined together with the above-described suturing procedure is the quality of the surgical knot tied to secure the tissue. Surgical knots are difficult to tie successfully, especially for non-surgical physicians that may be performing the endoscopic suturing procedure. It would be desirable to improve the reliability of the suture knot to increase the level of confidence in the procedures performed using the above-mentioned endoscopic devices. To improve the reliability of know methods of securing tissue together, the methods should be improved, or safeguarded with a secondary securement operation or eliminated entirely in favor of another procedure. The present invention is intended to provide an improved mechanism for joining internal tissue.

SUMMARY OF THE INVENTION

The present invention pertains to improvements to an endoscopic apposition device. The improvements may be embodied in a tissue apposition device similar to those disclosed in U.S. Pat. Nos. 5,792,153 or 5,080,663, or a stapling device such as is disclosed in U.S. Pat. No. 5,037,021. The disclosures of the above listed patents are incorporated by reference herein, in their entirety. The prior art endoscopic tissue apposition devices provided a mechanism for capturing only a single fold, double thickness of tissue through which a needle and suture were passed. The present invention provides a multiple suction port tissue apposition device is capable of capturing two or more separate folds of tissue simultaneously so that a tissue securement device, such as a suture, permanent suture tag and or tag lock system, implant clip or staple, may be passed through the multiple folds with one endoscopic intubation.

The device is comprised of a capsule attachable to the distal end of an endoscope, preferably a flexible viewing endoscope. The capsule comprises a body having multiple suction ports into which can be captured multiple portions of tissue. Each suction port defines an opening to an independent vacuum chamber or a vacuum chamber shared commonly with another suction port. Independent vacuum chambers may be operated simultaneously, through one vacuum source line, or sequentially, with each chamber in communication with an independent vacuum source.

Alternatively, the capsule may be configured such that multiple suction ports are in communication with a single, common vacuum chamber. Because only one vacuum chamber is provided, tissue is sucked into all suction ports simultaneously, when vacuum is applied to the common chamber. However, although a common vacuum chamber is used, tissue is collected into distinct multiple portions drawn through the separately defined suction ports. The multiple portions of collected tissue may then be secured by a tissue securement device such as a suture, permanent tag, implant, clip, staple or other means.

The several suction ports maybe arranged in a variety of configurations on the capsule. Ideally, the ports are arranged to coincide with desired final arrangement of secured tissue portions. Therefore, with appreciation for how the capsule will approach the subject tissue area being navigated at the distal end of an endoscope, the capsule should be configured such that the suction ports are positioned in relation to each other where the captured tissue portions are desired to be secured in relation to each other. In addition to the desired arrangement of tissue portions, consideration must be given to how securement means will be applied to the tissue portion given the arrangement of suction ports in relation to the working channel or channels of the endoscope.

In the example of a cylindrically shaped capsule, the ports are configured as arc shaped openings formed into the outside surface of the capsule. In one embodiment, the openings may be arranged in-line, parallel to the longitudinal axis of the capsule. Alternatively, the ports may be arranged to be side by side such that they are angularly displaced about the circumference of the capsule, but not displaced longitudinally along the length of the capsule. In one embodiment, four ports are arranged around the circumference of the capsule at equally spaced angular intervals. Ports can be arranged to be spaced apart at virtually any angular or longitudinal distance apart on the suturing capsule. For example ports arranged 90 degrees apart angularly and slightly apart longitudinally are positioned diagonally across the circumference of the capsule. The description of several various arrangements below is believed to be sufficient to enable one to extrapolate the requisite parameters to construct capsules having any desired arrangement of suction ports.

In the side-by-side tissue apposition embodiments, novel needle arrangements may be employed to penetrate tissue portions that are captured in the suction ports that are arranged away from the longitudinal axis of the capsule. A forked needle capable of simultaneously penetrating tissue portions held side-by-side is provided. For independent penetration of the tissue portions held captured in a side-by-side arrangement, a capsule design having a diverter in the needle track serves to guide independent needles to the selected suction port as they are advanced distally to penetrate tissue.

The multiple port apposition device of the present invention offers another advantage over previous designs in that the entire capsule body may be injection molded from a polymer material. A single piece injection molded unit is easier to produce than previous capsule designs, which were machined from metal and comprise several assembled components.

Another feature of the present invention is increased flexibility of the body. One or more points of longitudinal flexibility may be provided along the length of the capsule body by means of hinge. Due to the added length of the sewing capsule required to house two or more suction ports, the capsule may be too long to pass comfortably through natural body passageways such as the esophagus during an endoscopic procedure. To address the issue of passing a long rigid instrument through a curved natural body lumen, the present invention incorporates one or more hinged points along the length of the sewing capsule. The hinged portion permits the sewing capsule body to bend longitudinally, in at least one direction, so that the capsule body can be passed around a curve in the body lumen. If the hinge operates in only one direction, the endoscope and, thus, the sewing capsule body can be rotated upon reaching a curved portion of the body lumen so that the direction of bending flexibility coincides with the direction of the curve. After being navigated to the intended treatment location, a reinforcing rod may be advanced distally through all segments of the tissue apposition capsule body, locking the hinged body in place so that no bending at the hinges occurs during the procedure.

In another aspect of the invention, the tissue apposition capsule body is modified to utilize special tissue securement mechanisms. One tissue securement mechanism embodiment comprises sutures having anchoring elements at one end that permit them to be passed through tissue and then become anchored behind the tissue layer to permit suturing and retention of the fold of tissue. The anchoring element of the special suture material, such as polypropylene, may comprise a T-structure. The anchoring element is arranged in a T-structure in that the anchoring element is perpendicular to the longitudinal axis of the main portion of the suture element. In this arrangement the T-portion may be easily deformed so that it lies parallel to the main portion of the suture so that it may be passed through tissue when carried by a hollow needle that is part of the sewing capsule. After passing through the tissue, the T-portion of the suture may be ejected from the needle and the needle withdrawn from the tissue so that the T-portion resiliently returns to an orientation that is perpendicular to the axis of the main body portion of the suture, thus becoming anchored on the through side of the tissue.

The sewing capsule body can be modified to facilitate the operation of such a T-style suture anchor by formation of a ramp positioned distal to the most distal vacuum chamber that guides the T-portion of a suture being ejected from an advanced needle upward and outward, away from the sewing capsule so that it becomes oriented perpendicular to the longitudinal axis of the suture behind tissue through which the suture has been passed.

Another aspect of the invention provides for a multiple suture or staple magazine incorporated in the capsule body. The magazine helps to reduce a number of intubations required to place multiple tissue securement devices such as staples or sutures by holding several such devices and incorporating a mechanism to automatically and sequentially advance new securement devices into position for insertion into the tissue. Specifically, in the case of the suturing device having a reciprocating needle, multiple suture tags, or T's may be stored within the magazine during an endoscopic procedure. After the needle advances the first suture tag through tissue portions, the needle may be retracted to a proximal position whereby a spring loaded advancement mechanism may cue forward the next suture tag stored in the magazine into position to be carried by the needle through the next tissue location.

Another tissue securement device for use with the multiple suction port devices employs a suture tag lock system. The tag lock system uses a series of sutures and associated suture tags and tag lock blocks to hold the tissue portions in the desired plication orientation after the completing the procedure. The tag lock system hold sutures in a pre-arranged orientation on the suture capsule during navigation to the treatment site. Delivery of suture carrying tags through captured tissue by the needles serves to lock the tags into the lock blocks on the through side of the tissue, thereby completing the preconceived arrangement of sutures necessary to accomplish the plication form desired. A tag lock band may alternatively be employed to capture the suture tags on the through side of the tissue in place of the lock blocks.

Another tissue securement device for the multiple suction port embodiments comprises a helical coil implant that is threaded into the captured portions of tissue to hold them together. The coil implant embodiment may be used in a variety of procedure where endoscopic delivery of a tissue implant may be desirable. An example of other uses for the tissue implant may be to achieve tissue bulking in a region of gastro-intestinal tissue to treat GERD. The implant may also facilitate the delivery of bulking agents to a treatment site if the implant is configured to carry the agent by such means as coating.

In another aspect of the invention, tissue abrasion means are provided with the capsule to improve the adherence of tissue surfaces that are joined together. The abrasion means serves to create a slight injury to the tissue surfaces that will be joined by the apposition capsule. The injury initiates a healing process on those tissue surfaces that will lead to common tissue ingrowth between the surfaces over time to permanently join the tissues. The improved tissue apposition device and methods provided by the present invention can be used to join internal tissues via an endoscope for a wide variety of purposes such as: attaching a feeding tube to the small intestine; enclosing intestinal openings in the case of the fistula, repairing esophageal tears and suturing tissue sites of localized bleeding. However, the present invention is believed to be especially useful in endoscopic treatment of gastroesophageal reflux disease (GERD).

The abrasion means provided by the present invention may operate by a variety of mechanisms. Mechanical abrasion means may be provided by providing a roughened surface area to frictionally engage and abrade the tissue near the suction ports of the device. Alternatively, mechanical abrasion means may be employed by ejecting from the device an abrasive substance such as salt or sugar crystals. Chemical abrasion may be provided by releasing a chemically abrasive substance such as a suitably high concentration of hydrochloric acid. Electrical abrasion may be actuated by providing electrical elements near the suction port through which electrical current is passed to heat and abrade areas of tissue. Laser energy may also be applied to tissue to abrade and initiate the healing process. Alternatively, ultrasonic energy may be applied near the suction port opening. However, a preferred method of abrading a tissue is through the use of radio frequency (RF) energy adjacent the opening of the suction port.

The abrasion means may be incorporated in devices having a single suction port as those disclosed in the patents referenced above, but preferably the abrasion means is incorporated in an apposition device having multiple suction ports such as described herein. The arrangement and operation of the suction ports facilitates use of the abrasion means in that tissue can be held in place, in contact with the abrasion means, by applying light vacuum pressure through the vacuum chambers to collect tissue into the suction ports. By positioning the abrasion means adjacent the suction ports, tissue is reliably brought into contact with the abrasion means. Also facilitated is the correct positioning of the abrasion in the tissue area that will be brought into contact during the apposition procedure.

It is believed that joining area of tissue that have been injured slightly or abraded will undergo a healing process that promotes tissue ingrowth between the joined tissue surfaces resulting in a new, unified tissue mass rather than two separate tissues attached together by a tissue securement mechanism that could be subject to failure over time. Another advantage of the tissue ingrowth process is that biodegradable tissue securement means can be used which will degrade over time. In this situation, the tissue securement need only hold the tissues together temporarily, for sufficient time for the healing tissues to join together to form a unified tissue segment. In abrading the tissue to a sufficient degree to initiate the healing process, it is believed that only slight abrasion affecting the mucosal layer of the tissue is required. Accordingly, the tissue abrasion means discussed herein are intended to inflict only a slight amount of abrasion.

It is an object of the invention to provide an endoscopic tissue apposition device that reduces the number of intubations required to attach or repair internal tissue by a tissue securement mechanism comprising suture or staples.

It is another object of the invention to provide an endoscopic apposition device that is simple and economical to fabricate by injection molding techniques.

It is another object of the invention to provide a tissue apposition device having longitudinal flexibility to be easily navigable through a natural body lumen while mounted at the distal end of an endoscope.

It is another object of the invention to provide a tissue apposition device having multiple suction ports into which subject tissue may be collected and joined by a tissue securement device.

It is another object of the invention to provide a simplified tissue suture means having an anchor at one end which can remain on the through side of tissue during the process of tissue securement.

It is another object of the invention to provide an endoscopic tissue apposition device having a multiple suction ports in communication with a common vacuum chamber that operates to collect tissue into the multiple ports by applying vacuum to the common vacuum chamber.

It is another object of the invention to provide an endoscopic tissue apposition device having multiple suction ports in communication with multiple vacuum chambers that are independently operable to collect tissue sequentially into the multiple ports.

It is still another object of the invention to provide a tissue apposition device having a tissue securing device magazine configured to automatically and sequentially advance tissue securement devices into position for advancement through the tissue.

It is another object of the invention to provide a tissue apposition device with improved tissue suction capability.

Another object of the invention is to provide a method of joining internal tissue that comprises capturing at least two areas of tissue simultaneously to delivery tissue securement device through the areas of tissue to join them together.

It is an object of the present invention to provide an improvement to endoscopic tissue apposition devices that will provide a more reliable securement of internal tissues by promoting common ingrowth between those tissues in addition to attachment of tissue securement means.

It is another object of the invention to provide an endoscopic tissue apposition device that incorporates an abrasion means that utilizes a mechanical, electrical, chemical, laser, ultrasonic or radio frequency energy to abrade the subject tissue.

It is another object of the invention to provide an endoscopic tissue apposition device that safely abrades tissue sufficiently to initiate an injury response in that tissue without adversely and permanently damaging the tissue.

It is another object of the invention to provide an abrasion means that may be employed with an endoscopic tissue apposition device having a single or multiple suction ports.

It is another object of the invention to provide a tissue abrasion means that is equally applicable to tissue apposition devices utilizing a staple, suture, or suture tag securement means.

It is another object of the invention to provide a method for joining internal tissues of the human body comprising the abrading an area of tissue and joining multiple tissue portions such that the abraded area of tissue is brought into contact with itself or other tissue and undergoes a healing process that unites results in the bonding of the multiple tissue portions.

BRIEF DESCRIPTION OF THE DRAWINGS

The foregoing and other objects and advantages of the invention will be appreciated more fully from the following further description thereof, with reference to the accompanying diagrammatic drawings wherein:

FIG. 30 is an isometric view of a multiple suction port tissue apposition device employing a suture tag lock system;

FIG. 30A is a highly diagrammatic illustration of the tissue orientation after application of the suture tag lock system and depicted in FIG. 30;

FIG. 32 is an isometric view of a multiple suction port tissue apposition device employing a suture tag lock system using three suture leads;

FIG. 32A is a highly diagrammatic illustration of the tissue orientation after application of the suture tag lock system and depicted in FIG. 32;

FIG. 35 is an isometric view of a multiple port tissue apposition device employing a tag lock band;

FIG. 35A is a detailed illustration of a tag lock band;

DESCRIPTION OF THE ILLUSTRATIVE EMBODIMENTS

Figure 1:
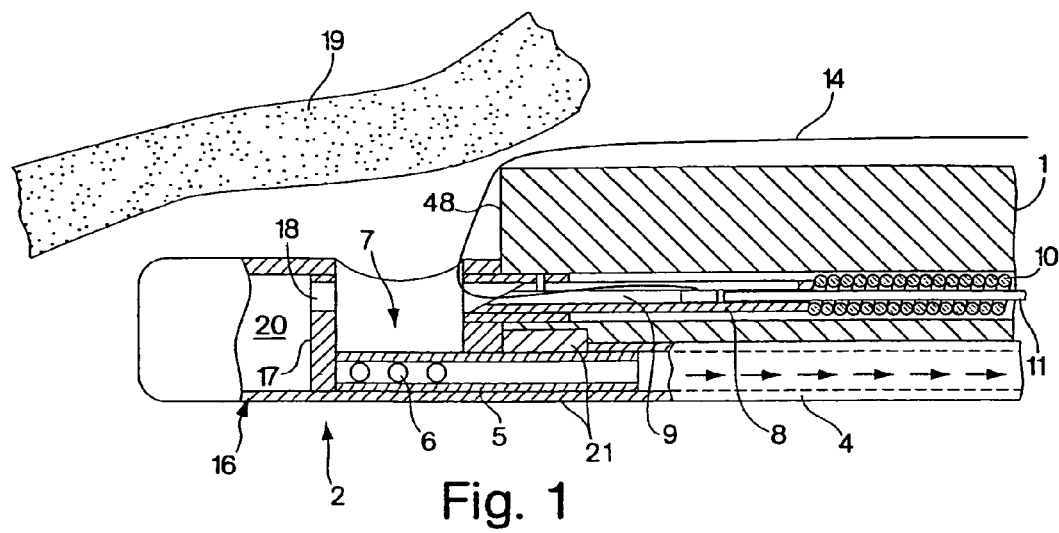
FIGS. 1-3 show successive steps in the operation of a prior art single stitch sewing device.
Figure 2:
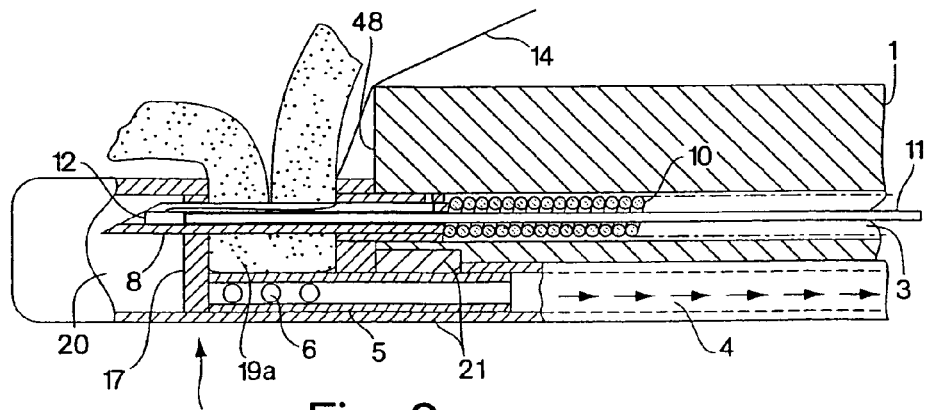
Figure 3:
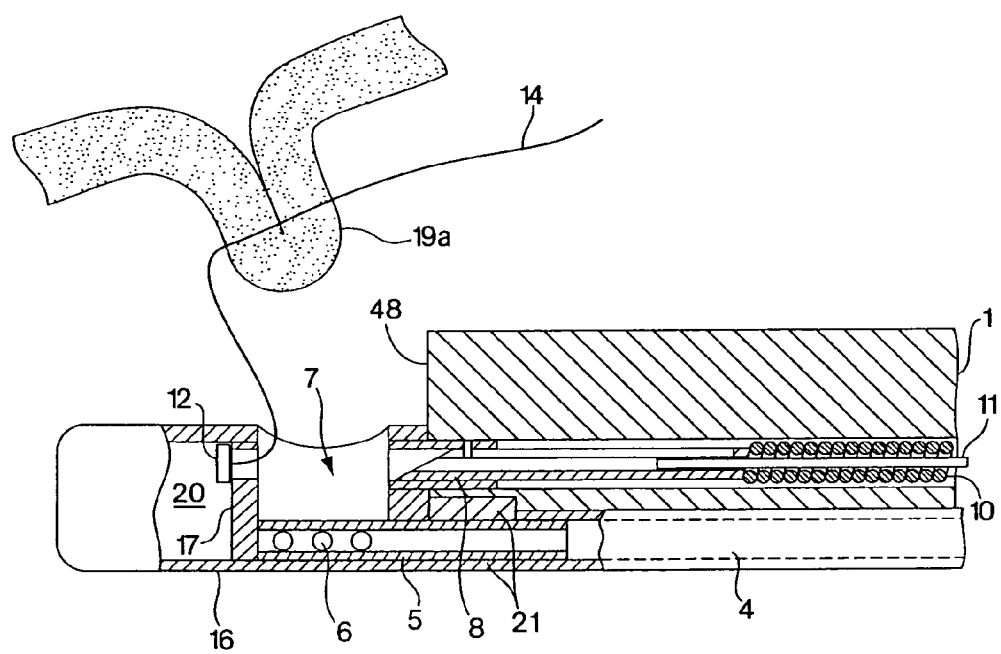

A description of the embodiments of the present invention is best presented in conjunction with an explanation of the operation of a prior art tissue apposition device, which this invention serves to improve. FIGS. 1-3 depict a prior art endoscopic suturing device disclosed in U.S. Pat. No. 5,792,153. FIG. 1 shows the distal end of a flexible endoscope 1, on which a sewing device 2 is attached. The endoscope is provided with a viewing channel, which is not shown, but which terminates at a lens on the distal face of the endoscope. The endoscope is further provided with a biopsy or working channel 3, and a suction channel 4 the proximal end of which is connected to a source of vacuum (not shown). The suction channel 4 may comprise a separate tube that runs along the exterior of the endoscope, rather than an internal lumen as shown. The sewing device 2 has a tube 5, which communicates with the suction pipe 4 and has a plurality of perforations 6 therein. These perforations communicate with an upwardly open vacuum chamber 7 formed in the sewing device.

Figure 1A:
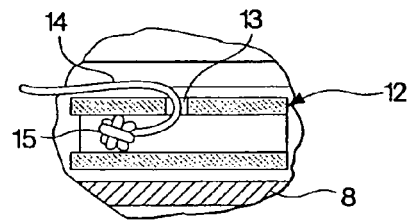

A hollow needle 8 is mounted in the biopsy channel 3, with its beveled tip extending into the sewing device. The needle has a channel 9 extending therethrough. A flexible, wire-wound cable 10 has its forward end attached to the rear of the needle 8, and a center wire 11 runs within the cable 10, along the entire length thereof, and is longitudinally movable with respect thereto. The diameter of the wire 11 is such that it is longitudinally movable within the channel 9 and, in the position shown in FIG. 1, the forward end portion of the wire 11 extends into the rear end portion of the channel 9. A thread carrier in the form of a tag 12 is slidably and releasably mounted in the channel 9. The tag is shown in detail in FIG. 1A. The tag is hollow and has an aperture 13 extending through the sidewall thereof. As can also be seen in FIG. 1, one end of a thread 14 is secured to the tag by passing it through the aperture 13 and tying in the end of a knot 15 of sufficient size to prevent the thread escaping from the tag. The tag may be made from a relatively rigid material such as stainless steel.

At the distal end of the sewing device is defined a hollow head portion 16 defining a chamber 20 therein. Between the chamber 20 and the cavity 7 is a wall 17, in which an aperture 18 is formed. The aperture 18 has a diameter that is marginally greater than the external diameter of the needle 8, and is aligned therewith. The clearance between the needle 8 and the aperture 18 must be sufficiently small to prevent tissue being forced through the aperture and causing the needle to jam.

Finally, FIG. 1 shows a portion of the patient's tissue 19, in which a stitch is to be formed.

In operation, suction is applied to the suction pipe 4, and thence, via the perforations 6 in the tube 5 to the cavity 7. This sucks into the cavity a U-shaped portion 19a of the tissue 19, as shown in FIG. 2. The hollow needle 8 is pushed through the U-shaped tissue portion 19a by extending distally the wire-wound cable 10 and associated needle 8. After full advancement of the needle through both folds of the U-shaped tissue portion, the tip potion of the needle 8 is distal to the wall 17 and within the chamber 20 in the hollow head portion 16. Distal movement of wire 11, slidably received within the wound cable 10, pushes the tag 12 out of the channel 9 and into the chamber 20 where it rotates out of alignment with aperture 18 to become captured in the chamber.

The wire 11 is then withdrawn proximally, followed by proximal withdrawal of the cable 10, to withdraw the needle 8 from the tissue portion 19a. The suction is then discontinued allowing the U-shaped tissue portion 19a to be released from the cavity 7. As shown in FIG. 3, the released tissue is left with a suture thread 14 passing through the two layers of tissue that form the U-shaped fold 19a. One end of the suture is joined to the tag 12 that remains captured in the chamber 20 and the other end of the suture extends through the patient's esophagus and out of the mouth. Finally, the endoscope and dewing device are withdrawn from the patient. In so doing, the thread 14 is pulled partially through the tissue portion 19a, as the captured tag 12 is withdrawn proximally and brought outside the patient.

With both ends of the thread 14 outside of the patient, the thread can be knotted and the knot endoscopically pushed down to the suture site and severed by an endoscopic knot pusher such as that disclosed in U.S. Pat. No. 6,010,515 (Swain et al). As an alternative to tying a knot, a suture lock or clip may be guided over the suture thread, down the esophagus and secured via an endoscope or suitable delivery catheter to hold the suture thread tight against the tissue. Examples of suitable suture locks and delivery systems are disclosed in U.S. patent application entitled Suture Lock, Delivery Systems and Methods filed Feb. 2, 2001.

In using the endoscopic suturing device to treat G.E.R.D. it is believed that capture of multiple tissue portions and suturing and gathering them together provide an effective treatment. To accomplish this using the prior art device, multiple intubations of the endoscope down the patient's esophagus are required. Once, multiple (tissue portions, have been captured and sutured with thread, they are gathered together and secured by tying of surgical knots in the thread or application of suture lock devices. It should be noted that a multiple stitch embodiment also is disclosed in U.S. Pat. No. 5,792,153. However, that embodiment requires the user to release the currently sutured tissue portion and relocate the device to collect a new tissue portion before making the second stitch. It is an object of the present invention to reduce the number of intubations required to capture multiple tissue portions and to enhance the security of the attachment of the tissue portions.

Figure 4:
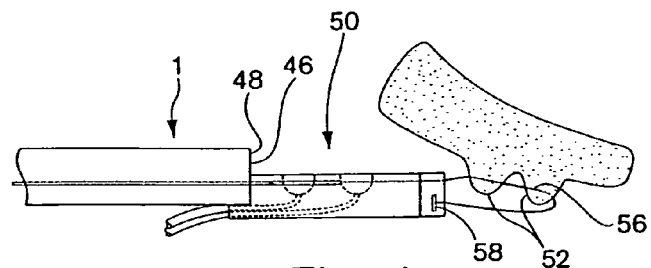
FIG. 4 is a diagrammatic side view of a tissue apposition device mounted to an endoscope.
Figure 5:
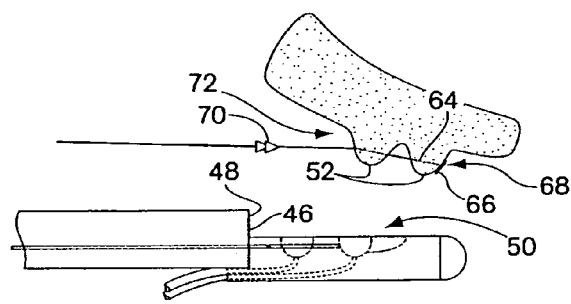
FIG. 5 is a diagrammatic side view of a tissue apposition device mounted to an endoscope.

FIGS. 4-5 illustrates the advantages provided by the operation of a multiple suction port apposition device 50. Specifically, the device can secure multiple tissue portions 52 simultaneously for application of a tissue securing device, such as a suture, tag or staple. Securing two tissue portions 52 in the same number of steps that the prior art device requires to secure a single tissue portion doubles efficiency, reducing the total number of endoscopic intubations required to complete the procedure and reducing the time needed to complete the procedure. Though dual suction port embodiments are discussed for illustration purposes, it should be understood that the multiple port device could be configured to have three or more suction ports.

The dual suction port tissue apposition device shown in FIG. 4 passes through both tissue portions a suture 56 with a tag 58 capturable in the end cap 60 of the sewing capsule 62, in similar fashion to the prior art device discussed above. The dual suction port tissue apposition device shown in FIG. 5 passes through both tissue portions a suture 64 having a permanent tag 66 at its end. The permanent tag is not captured by the suturing device to later provide a lead for tying a surgical knot. Rather, the permanent tag remains in the body, anchored on the through side 68 of the distal tissue portion. The tissue portions are then secured tightly together, not by a surgical knot, but by a frictionally engageable two piece suture lock device 70 advanced along the single suture lead 64 to abut the proximal side 72 of the tissue portion.

Figure 7:
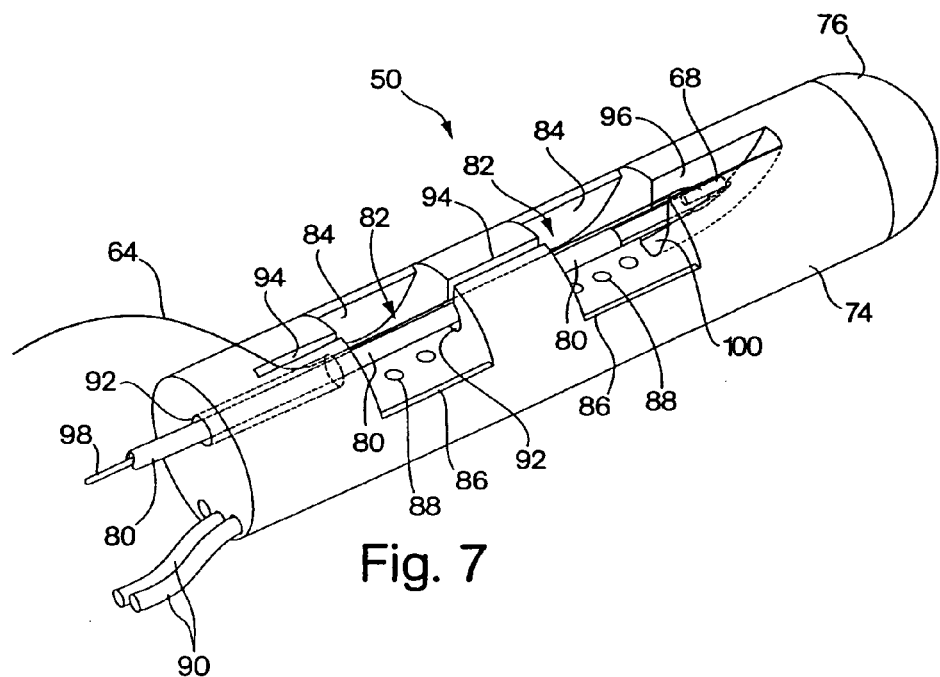
Figure 8:
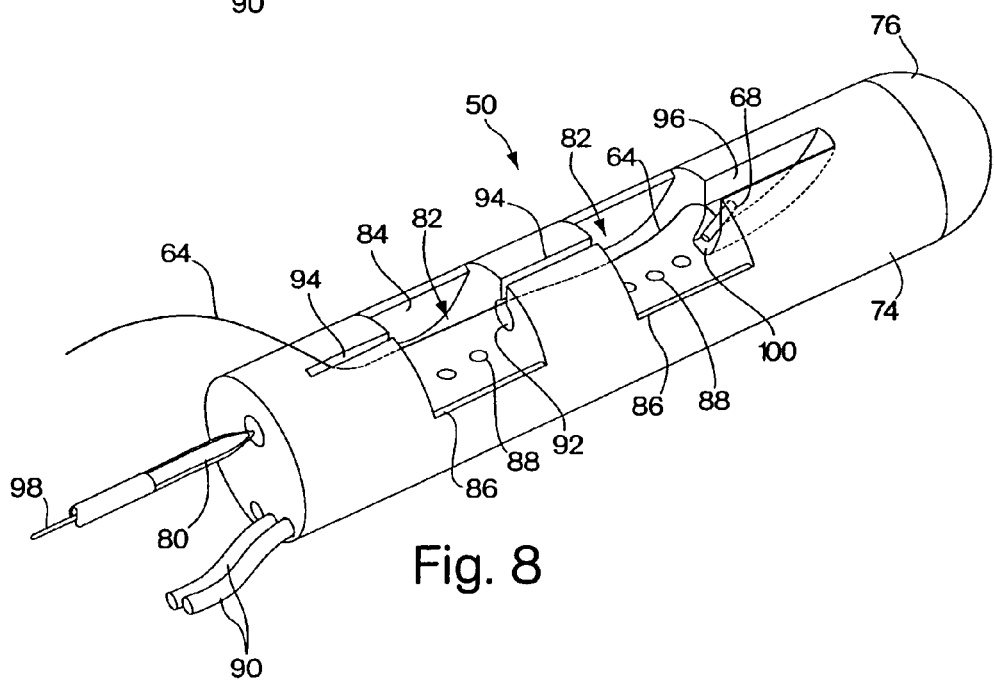

In one embodiment of the invention, multiple suction ports are defined in line on the sewing device, along a common longitudinal axis that is parallel to the longitudinal axis of the device. An isometric view of an in-line dual suction port endoscopic tissue apposition device 50 is shown in FIGS. 6-8, in various stages of operation.

Figure 6:
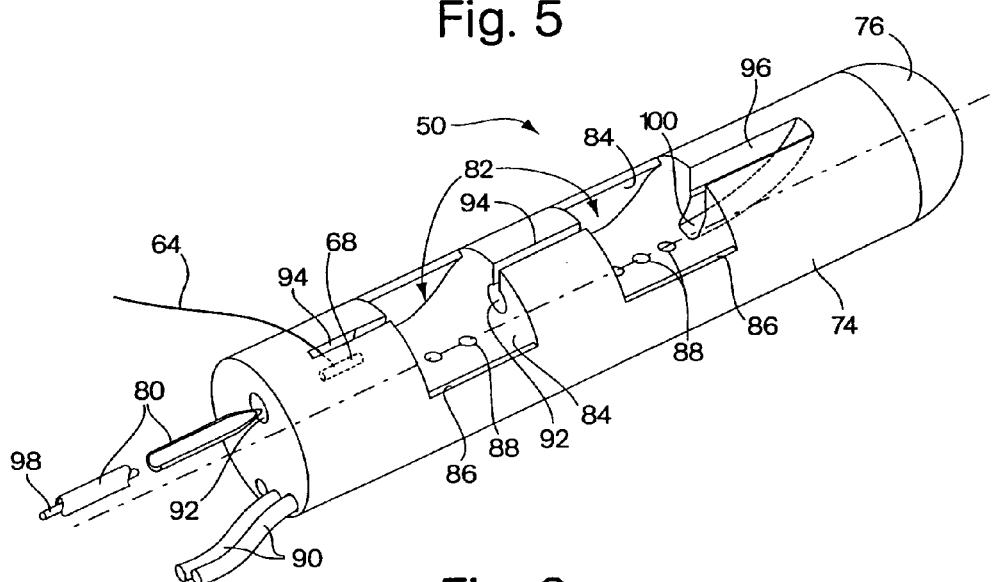
FIGS. 6-8 are isometric views of a multiple suction port apposition device in various stages of operation.

In FIG. 6, a slotted and beveled hypodermic suturing needle 80 is in the fully retracted position, with suture tag 68 not yet loaded, and the capsule ready to receive tissue. The sewing device 50 is characterized by a tubular body or capsule 74 that is machined from metal or injection molded from a rigid polymer material. The body may be formed with an atraumatic distal tip 76 to avoid injury to the walls of a body lumen through which the device is delivered. A plurality of suction ports 86 are formed into the body along its length. Suction ports 86 are large openings defined through the capsule 74, and open to one or more vacuum chambers 82. The chambers are defined in the capsule by surfaces forming sidewalls 84. Communication of the suction ports with the vacuum chambers 82 permits vacuum to reach tissue that is adjacent to the ports to accomplish capture of tissue portions 52 into the chamber. Any number of suction ports can be formed on the capsule body. However, two suction port devices are shown here as illustrative examples because often in the treatment of GERD, a series of two sutures joined together are formed along the stomach wall, below the Z-line. Though more ports and chambers can be formed on the body, the extra body length they would require in the in-line embodiment could potentially present difficulty during navigation of the rigid body through the curves of a natural body lumen.

Tissue portions are drawn into the suction ports and into the vacuum chambers by suction introduced to the chambers through air passages 88. The air passages are open to independent internal channels in the body that are joined to vacuum lines 90. The vacuum lines extend from the proximal end of the capsule body, external to the endoscope, to the proximal end of the scope. Outside the patient, the vacuum lines can be joined to a portable or institutional vacuum source (not shown). A control valve may be inserted in-line near the proximal end of the tubes for selective control of the vacuum by the user. The air passages of all cambers may be joined and controlled by a single vacuum line. Alternatively, as shown in FIG. 6, separate vacuum lines may be used to supply suction to the air passages of different vacuum chambers. Use of separate vacuum lines permits independent control of suction provided to the several chambers by the use of separate control valves for each vacuum tube at their proximal ends.

Independent vacuum supply to the air passages of each chamber not only helps to ensure adequate vacuum pressure to each chamber, but also permits sequential suctioning of tissue into the chambers. When tissue is collected into both chambers simultaneously, the distal chamber is blocked from the viewing lens 48 on the distal face 46 of the endoscope 1, as shown in FIG. 5. Therefore, the physician is unable to visually determine whether tissue has been adequately collected into the vacuum chamber so that the needle 80 can be safely advanced through. By applying vacuum first to the distal chamber, tissue collection into that chamber can be visually verified before the view is blocked by tissue entering the proximal chamber. Next, vacuum can be applied to the proximal chamber to capture tissue so that tissue is collected in both chambers simultaneously and held in readiness for penetration by the suture needle (or staple) through both tissue portions with one stroke. However, even with independent vacuum lines, it is possible, and may be desirable to apply a vacuum to all chambers simultaneously.

The needle 80 is longitudinally slidable through the capsule body 50, as in the prior art devices. In the in-line dual chamber embodiment shown in FIGS. 6-8, a tunnel-like needle track 92 extends longitudinally through solid portions in the upper half of the body, not otherwise defined by the vacuum chambers. From the needle track, a thin suture channel 94 extends upwardly through the top surface of the capsule body to provide a space through which the suture lead 64 may pass as the suture tag 68 is advanced by the needle through the needle track 92. The channel 94 is only a sufficient width to permit the suture to pass but is too small to permit passage of the larger needle or suture tag 68. The small dimension of the channel helps maintain the needle and suture tag with in the needle track until they are extended distal to the most distal chamber. An enlarged exit channel 96 extends upwardly from the needle track along the body a short distance distally from the distal chamber 82. The enlarged channel facilitates exit of the suture tag 68 from the body, to follow the released tissue to which it has been attached after being ejected from the extended needle 80 by pusher wire 98, as is shown in FIGS. 7 and 8. It is noted that tissue portions normally captured in the vacuum chambers during advancement of the needle and ejection of the tag are not shown in FIG. 7 for clarity. Additionally, a ramp 100 may be formed in the bottom surface of the needle track along the length of the exit channel 96. Extending upwardly as it extends distally, the ramp 100 helps guide an ejected tag up and out from the exit channel and away from the capsule body.

Figure 9:
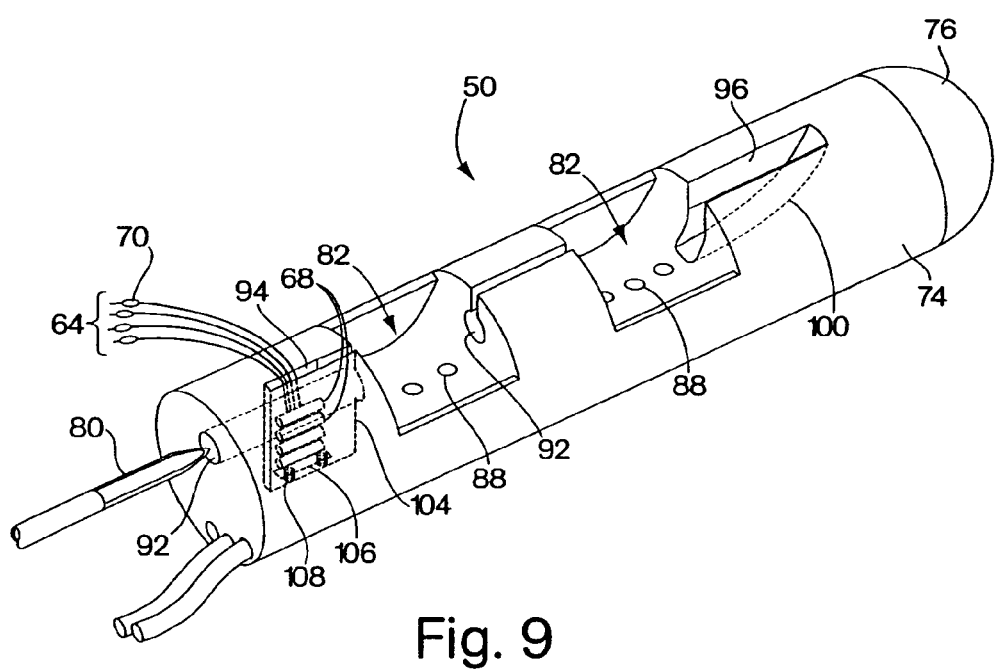
FIG. 9 is an isometric and partial cutaway view of a multiple suction port apposition device with a suture magazine.

Another feature that may be integrated into the multiple chamber tissue apposition device to reduce intubations and procedure time is a magazine 102, shown in FIG. 9. The magazine is configured to hold multiple suture tags or permanent tags or staples in readiness for automatic and sequential loading into the needle or other advancement device during the procedure. The magazine may comprise a rectangular cavity 104 extending from the suture channel 94 down through the needle track 82. Several tags 68 can be preloaded into the cavity 104 before the procedure. Spring-loaded support tray 106 provides an upwardly biasing force on the stack of tags by virtue of the resiliency of several springs 108 supporting the tray from the bottom of the cavity. Upward travel of the tags in the cavity is limited by the limited clearance of the suture channel 94, which is too small to accept a suture tag. Therefore, the top tag is biased into position along the needle track.

When the needle advances distally from its starting position shown in FIG. 9, it receives the top tag within its lumen and carries it through the tissue portions. When the needle is withdrawn proximally again, vacating the needle track, the next tag is free to move upward under the biasing force of the springs 106, into cue in the needle track. Because the endoscope does not have to be withdrawn for reloading after delivery of each suture, the number of intubations made during a procedure can be greatly reduced. In the case of permanent suture tags 68, the several suture leads 64 may each be preloaded with suture lock devices 70 to further hasten the tissue apposition procedure. For additional details regarding suitable suture lock devices see related provisional application entitled "Suture Lock, Delivery Devices and Methods" filed Mar. 2, 2001. Alternatively, with some embodiments of the apposition device, the suture tags may be driven into one or more tag lock devices that remain in the body, on the through side of the tissue and are joined to another tag or to a suture lead extending back outside the patient. Embodiments employing multiple suture tags are best suited to use tag locks, which will be described in greater detail below.

Figure 10:
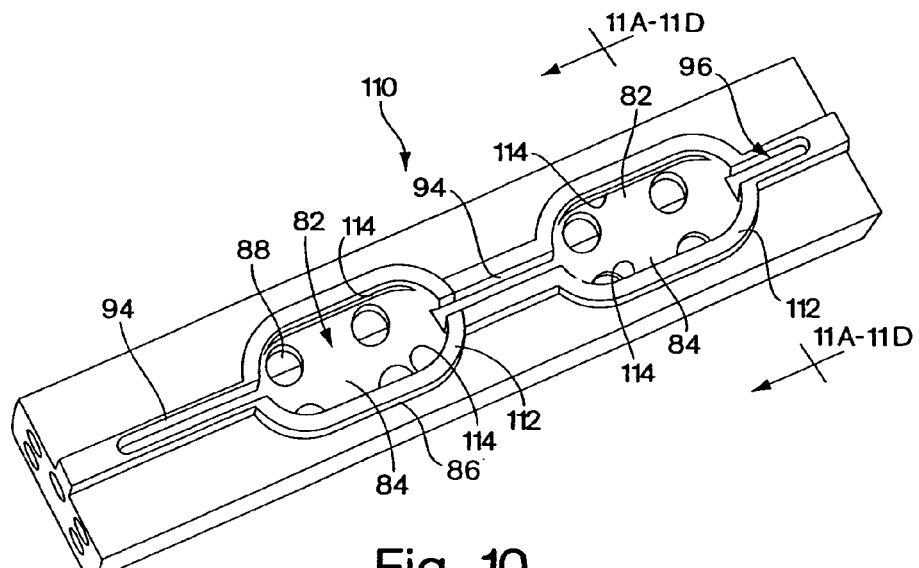
FIG. 10 is an isometric view of a modified multiple suction port apposition device.
Figure 11A:
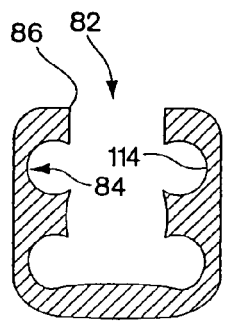
FIGS. 11A-11D are various cross-sectional views taken along the representative line 11A-11D-11A-11D of FIG. 10.
Figure 11B:
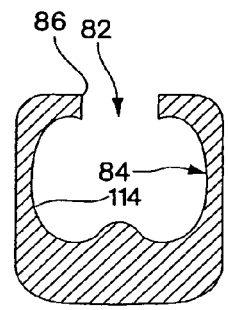
Figure 11C:
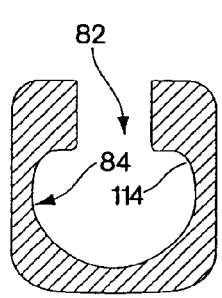
Figure 11D:
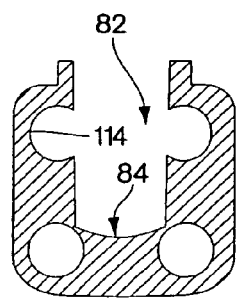

FIG. 10 shows additional modifications that may be made to a multiple suction port capsule body 110 to improve tissue suction and retention. First, circumferential ridges 112 can be formed around the chamber openings defining suction ports 86 during formation of the body. The ridges protrude from the surface of the body slightly and are believed to improve sealing contact with surrounding tissue thereby increasing suction efficiency. The improved suction helps to ensure that tissue is drawn fully into the chamber so that suture is properly located through the tissue fold.

Another aspect of the invention, shown in FIG. 10, is the addition of capture recesses on the surfaces of the sidewalls 84 of the vacuum chambers, just below the suction port 86. It is believed that the addition of the recesses 114 will help retain tissue fully within the chamber after it has been sucked in initially. It is believed that after tissue has been sucked in, it will fill the chamber under vacuum, including the recesses. After the recesses have become filled, the upper surface of the recesses will act as a flange to hold the tissue in the chamber. The modifications shown in FIG. 10 may be employed in any of the apposition device embodiments illustrated herein.

Figure 12A:
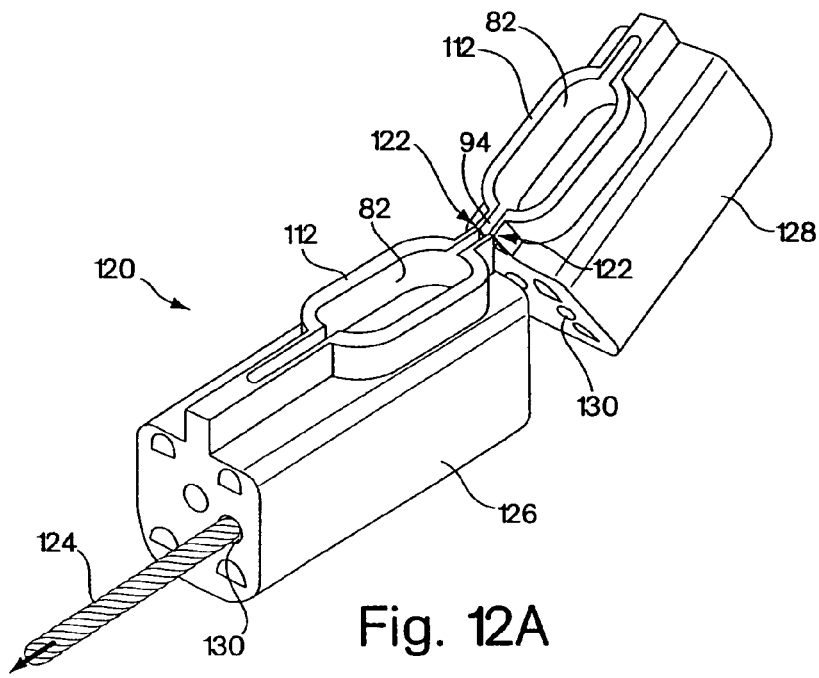
FIGS. 12A-12B are isometric view of a hinged multiple suction port apposition device.
Figure 12B:
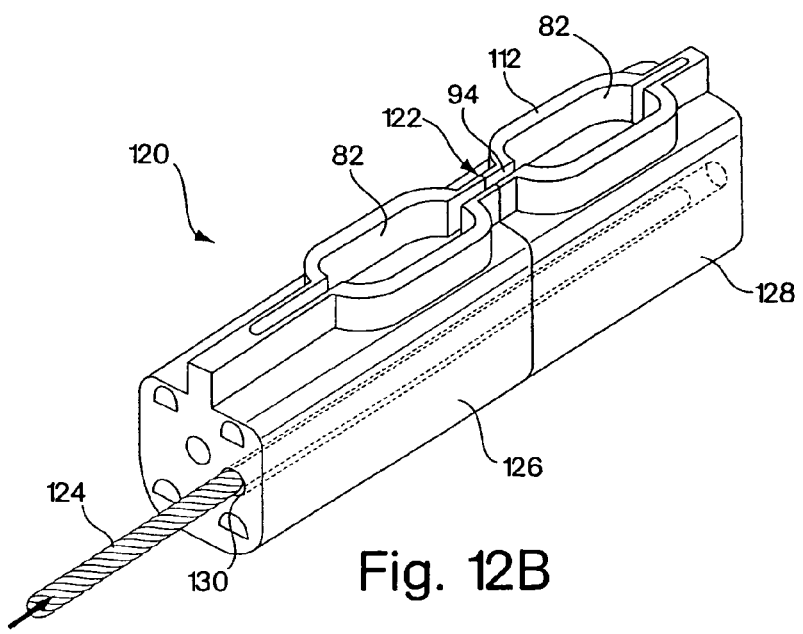

FIGS. 12A and 12B show another aspect of the invention. A hinge 122 may be incorporated into the capsule body 120, along its length to permit bending of the otherwise rigid body during navigation through curved body passages. In the case of an injection molded polymer body, the hinge 122 may be a living hinge defined by a thin line of material joining the two halves 126 and 128. The living hinge permits the halves to articulate relative to each other, in one direction, providing some longitudinal flexibility to the rigid body having an increased length due to the incorporation of additional suction ports. Articulation in one direction about only one hinged line is expected to provide adequate flexibility for the various curves encountered in a body lumen because, regardless of the direction of the curve encountered, the endoscope can simply be rotated until the direction of bending freedom of the capsule body coincides with the direction of the curve. Multiple hinges can be provided along one body and though they could be oriented in different directions, such varied positioning may be unnecessary in light of the forgoing statements.

Because the capsule body must aligned and straight to accept passage of the reciprocating needle during the procedure, a remotely operable locking mechanism is provided to lock the hinged halves 126 and 128. A locking rod 124 is longitudinally slidable through a locking channel 130, which extends longitudinally through both articulating halves 126 and 128 of the hinged body 120. The rod 124 extends to the proximal end of the endoscope to be operable by the physician. In its retraced position, shown in FIG. 12A, the rod occupies channel 13 only in the first half 126 of the hinged body, permitting half 128 to articulate freely about the hinge 122. In the advanced position, shown in FIG. 12B, the rod occupies the channel 130 in both halves 126 and 128 of the body 120, locking them together in a straight configuration.

Figure 13:
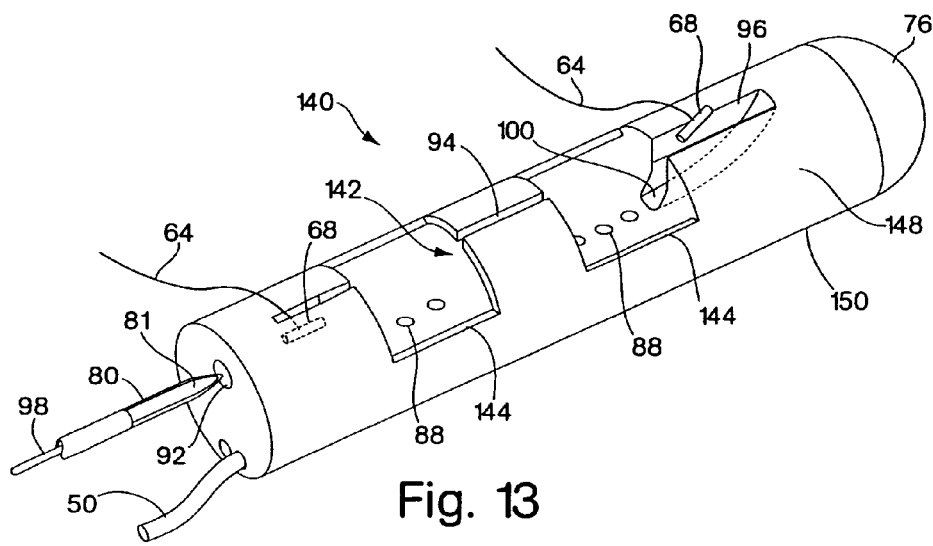
FIG. 13 is an isometric view of a multiple suction port, single chamber tissue apposition device.

FIG. 13 shows an alternate embodiment of the present invention that operates multiple suction ports from a single vacuum chamber 142 that is common to multiple ports 144. A multiple port tissue apposition device 140 comprises a capsule body 148 having an outer surface 150 through which several suction ports 144 are formed. Suction to collect the tissue through the ports 144 is provided through a single vacuum chamber 142 within the interior of the capsule body 148 that is common to at least two of the suction ports 144. As in the embodiments discussed above, vacuum is provided through air passages 88 at the bottom of the vacuum chamber 142. Those vacuum ports are joined to a vacuum line 50 that is in communication with a source of vacuum external to the patient.

In the embodiment shown in FIG. 13, two tissue suction ports 144 are provided on the capsule body 148 and a single vacuum chamber 142 is common to both suction ports. However, any number of ports may be formed into the capsule body surface 150 to provide the desired number of individual ports through which tissue can be collected and formed. It may be desirable to provide other combinations of ports 144 and vacuum chambers 142. For example, it may be preferred to provide a single vacuum chamber 142 in communication with two ports 144 and provide a separate vacuum chamber in communication with a third port at another location on the capsule body 148. Alternatively, if four ports were desired, two vacuum chambers could be provided, each serving two ports. Regardless of the configuration of vacuum chambers to tissue suction ports, the purpose of the invention is achieved with the present embodiment because multiple portions of tissue can be collected by the device at one time to permit attachment of a tissue securement device (such as a suture, permanent tag, or staple) with one operation of the device.

The operation of the present embodiment is essentially the same as has been outlined above for the previous embodiment. Specifically, the device 140 is secured to the distal end of an endoscope and is navigated to a site of internal tissue intended to be sutured. Using the viewing capability of the endoscope, the suction ports 144 are positioned adjacent tissue to be treated. Vacuum is introduced through vacuum line 50, in communication with air passages 88 to provide suction to the vacuum chamber 142, commonly shared by suction ports 144. Tissue is collected into the chamber 142 through individual suction ports 144, forming distinct portions of tissue within each chamber. Because the suction ports 144 share a common vacuum chamber, sequential suctioning of tissue into individual suction ports is not possible with this embodiment, unless several vacuum chambers are provided, each serving multiple suction ports.

A tissue securement advancement mechanism such as a hollow and slotted needle 80 carrying a pusher wire 98 may then be advanced distally through needle track 92 and through the vacuum chamber 142 where the tissue has been collected. As the needle 80 is advanced distally, it receives in its lumen 81 a suture tag 68, which is joined to a suture 64. As the needle penetrates the individual portions of tissue that have been collected in the vacuum chamber 142, it passes the suture tag and suture through the tissue as well. After passing through all portions of tissue, the suture tag is ejected from the distal end of the needle into exit channel 96 extending distally of the most distal suction port 144. Ramp 100 of the exit channel guides the suture tag 68 upward and outward from the device when the vacuum is discontinued and tissue is released from the suction ports 144. The suture 64 passes through the suture chamber 94 extending along the top surface of the capsule 148. The suture and tag then remain permanently with the tissue as is described in detail above in connection with the preferred embodiments.

Figure 14:
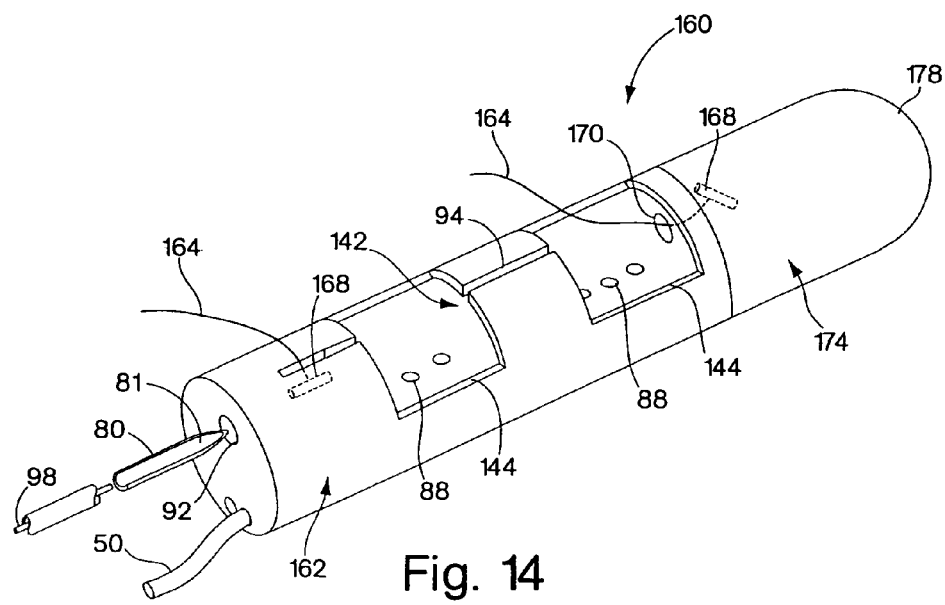
FIG. 14 is an isometric view of a multiple suction port, single vacuum chamber tissue apposition device.

FIG. 14 illustrates another alternate embodiment of the multiple suction port concept described above in FIG. 13. The multiple suction port tissue apposition device shown in FIG. 14; however, is configured to utilize a capturable suture tag 168 as was employed in the prior art devices described above. In comparison to the embodiment of FIG. 13, the suture tag 168 is ejected from the advanced needle into a capture chamber 174 where it is retained and removed from the patient with withdrawal of the endoscope so that a surgical knot may be tied in advance to secure the suture. The capture chamber 174 is defined by a removable end cap 178 that is secured to the distal end of the capsule 162. The suture tag 168 is advanced into the capture chamber 174 after the needle has been advanced through portions of tissue captured through suction ports 144 into chamber 142 and passed through the capture chamber entrance 170. After the pusher wire 98 is advanced through the lumen 81 of the needle to eject the tag into the capture chamber 174, the tag becomes trapped because it is free to rotate out of alignment with the capture chamber entry 170. It is noted that needle track 92 need not extend through the entire length of the vacuum chamber but may optionally be provided through areas of the chamber not defined by suction ports 144 to provide longitudinal directional stability for the needle as it passes through the mounds of tissue 144.

Figure 15:
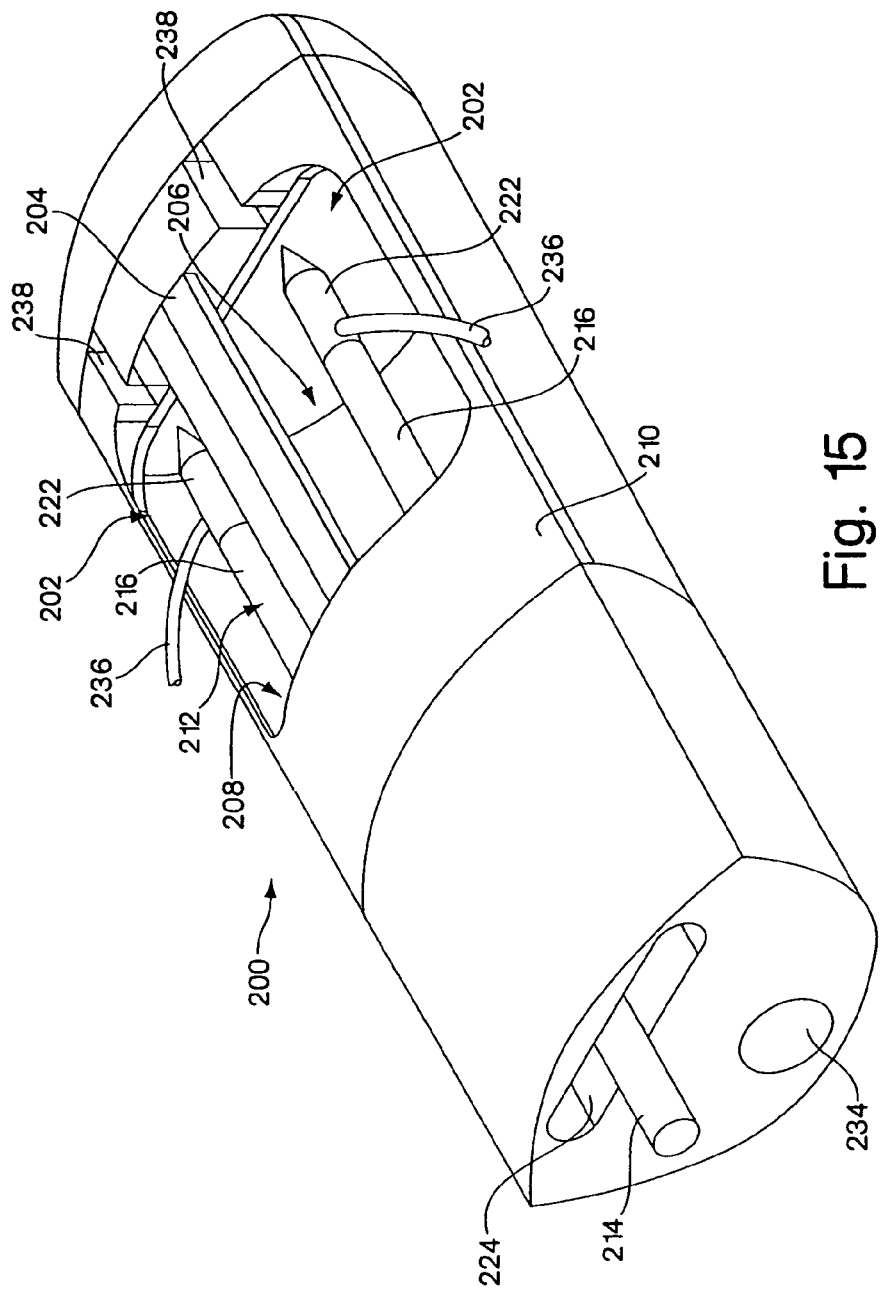
FIG. 15 is an isometric view of a side-by-side multiple suction port device having a forked needle.

FIG. 15 shows another embodiment of the multiple port tissue apposition device in which the suction ports are arranged side-by-side rather than longitudinally in line as were the above-described embodiments. The suturing capsule 200 has a tissue capture mechanism comprising two or more suction ports 202 that arranged side-by-side, angularly offset but substantially aligned with each other longitudinally (referring to the longitudinal axis of the capsule and endoscope). The suction ports 202 define openings into the capsule 200 and are separated by partition 204. As with the previous embodiments, suction ports 202 open to a vacuum chamber 206 defined by sidewalls 208 inside the capsule 200. As with the above embodiments, vacuum is created in the vacuum chambers through negative pressure introduced by air passages 88 (not shown) to cause tissue to be drawn into the vacuum chambers through suction ports 202. The air passages are in communication with vacuum channel 234 formed through the capsule body and joinable to a vacuum channel 4 of the endoscope or an independent vacuum line.

As tissue is drawn into the suction ports 202 under vacuum, the partition 204 causes the tissue to be separated into two distinct mounds or portions into which tissue securement means such as sutures may be driven as is described below. The suction ports 202 may be in communication with a single, common vacuum chamber 206 (as shown in FIG. 15) or each suction port may open to independent, dedicated vacuum chambers that can be separately evacuated. Separate vacuum chambers would further be defined by a sidewall extending from partition 204 into the vacuum chamber 206.

Figure 16:
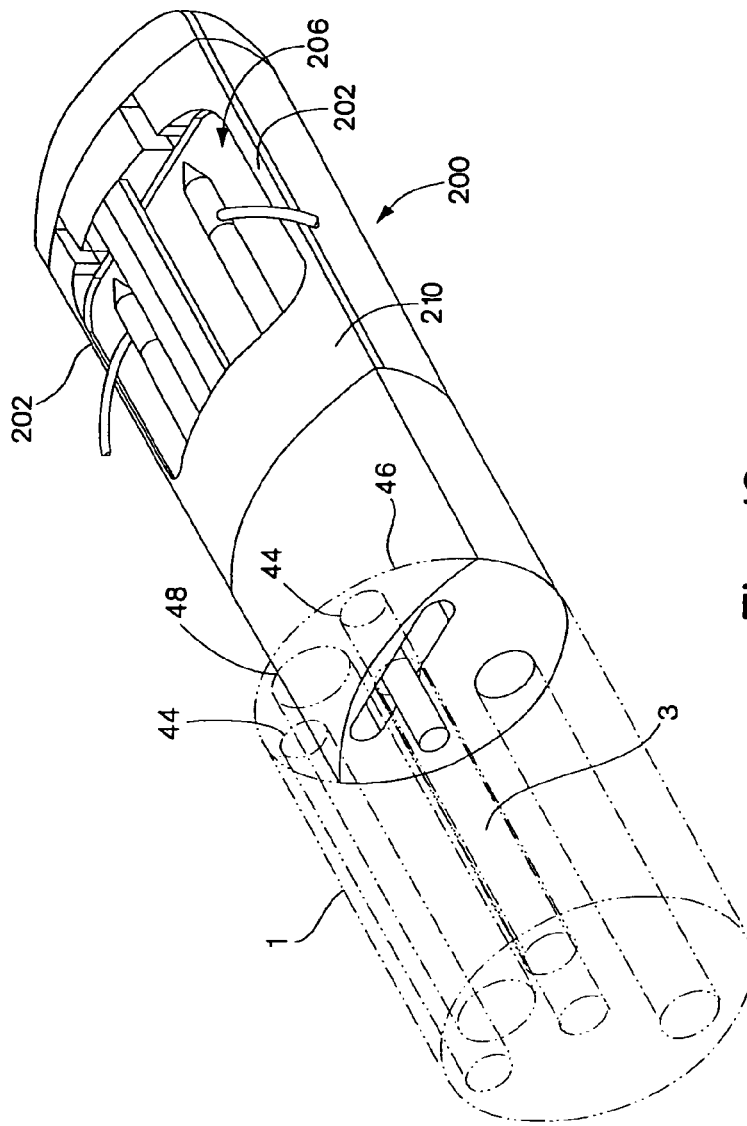
FIG. 16 is an isometric view of a side-by-side multiple suction port device having a forked needle attached to the distal end of an endoscope shown in phantom.

As shown in FIGS. 15 and 16, the side-by-side suturing capsule 200 may be formed to have a substantially D-shaped cross-section, as opposed to the cylindrical cross-sectional shape of the above-described embodiments. The D-shaped cross-sectional shape of the capsule provides a tissue engagement surface 210 that is effectively more flat and wide than would be presented by a cylindrical capsule having side-by-side suction port arrangement. The added width of the tissue engagement surface 210 provides a wider area in which the suction ports 202 may be formed. The wider tissue engagement surface 210 maximizes the width of the side-by-side suction ports 202 to insure that an adequate amount of tissue can be drawn into the vacuum chamber 206 during the procedure. Additionally, as shown in FIG. 15, the D-shaped cross-section of the capsule body 200 preserves the viewing capability through viewing lens 48 and lights 44 on the distal face 46 of an endoscope 1 (shown in phantom) to which the capsule is attached. Preservation of the viewing capability of the endoscope is important in design of the capsule body so that the physician can visually verify the positioning of the suturing capsule and verify that tissue portions have been fully captured within the vacuum chamber 206 prior to suturing.

With the side-by-side capsule embodiment 200, there are several possible mechanisms for tissue securement may be employed. Tissue securement may comprise suture material passed through the tissue portions. Alternatively, the tissue securement mechanism may comprise a clip that is driven into the tissue to secure the portions and remains in the patient, such as a helical wire coil described below. Several tissue securement advancement mechanisms are also possible. Specifically, several needle configurations and suture tag securement embodiments are possible with the multiple suction port capsule 200.

In one embodiment of the side-by-side device, shown in FIGS. 15-18, a forked needle 212 slidably mounted in the capsule 200 is employed to penetrate simultaneously the tissue portions captured in suction ports 202 for suture delivery. As best shown in the sectional isometric view of the capsule 200, shown in FIG. 18, the forked needle 212 may comprise a forked stainless steel structure having a base 214 and two fork prongs 216 that are hollow and terminate in sectioned tips 218 that define U-shaped receptacles 220 for receiving and frictionally engaging pointed suture tags 222 (shown in FIG. 15). Alternatively, the tags may be carried within the hollow fork prongs during delivery and ejected out with a pusher wire on the through side of the tissue after tissue penetration (as with the prior art device of FIGS. 1-3).

Figure 17:
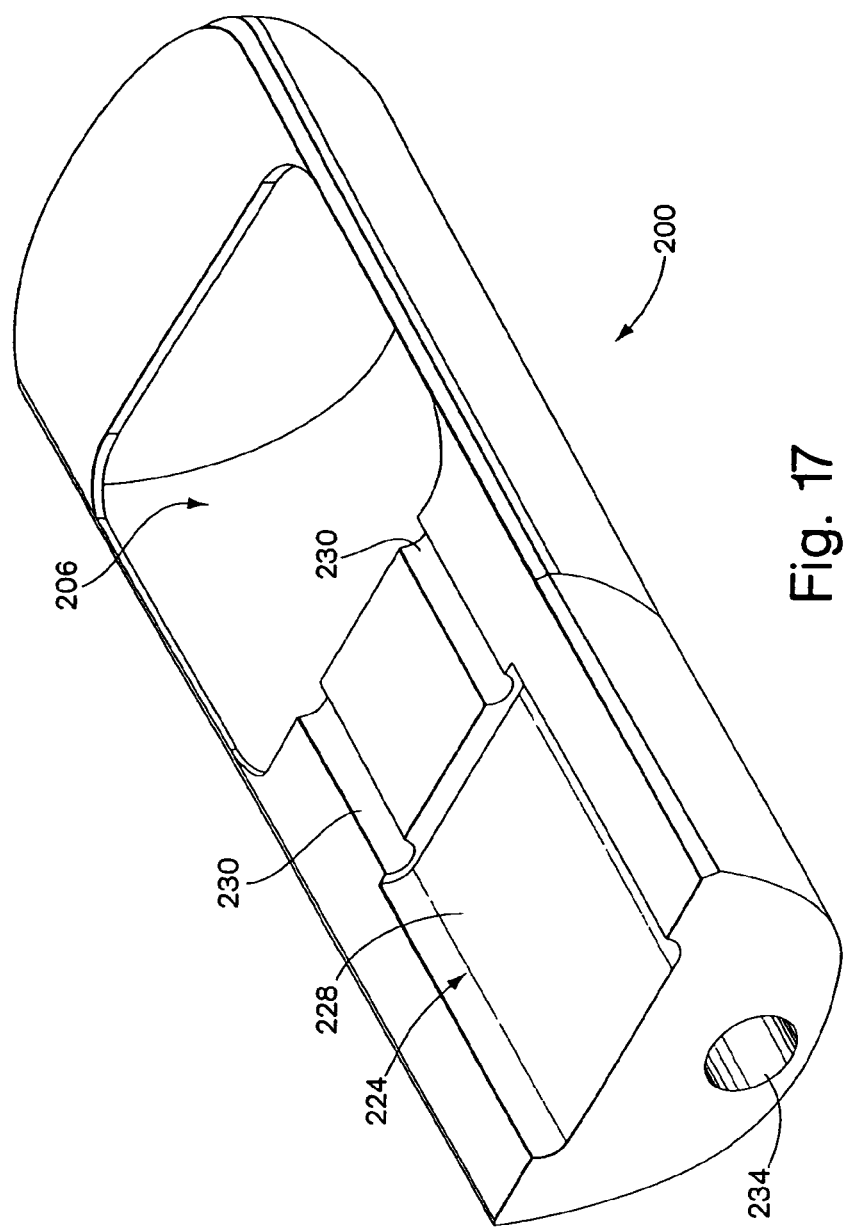
FIG. 17 is a sectional isometric view of a side-by-side multiple suction port device having a forked needle.
Figure 18:
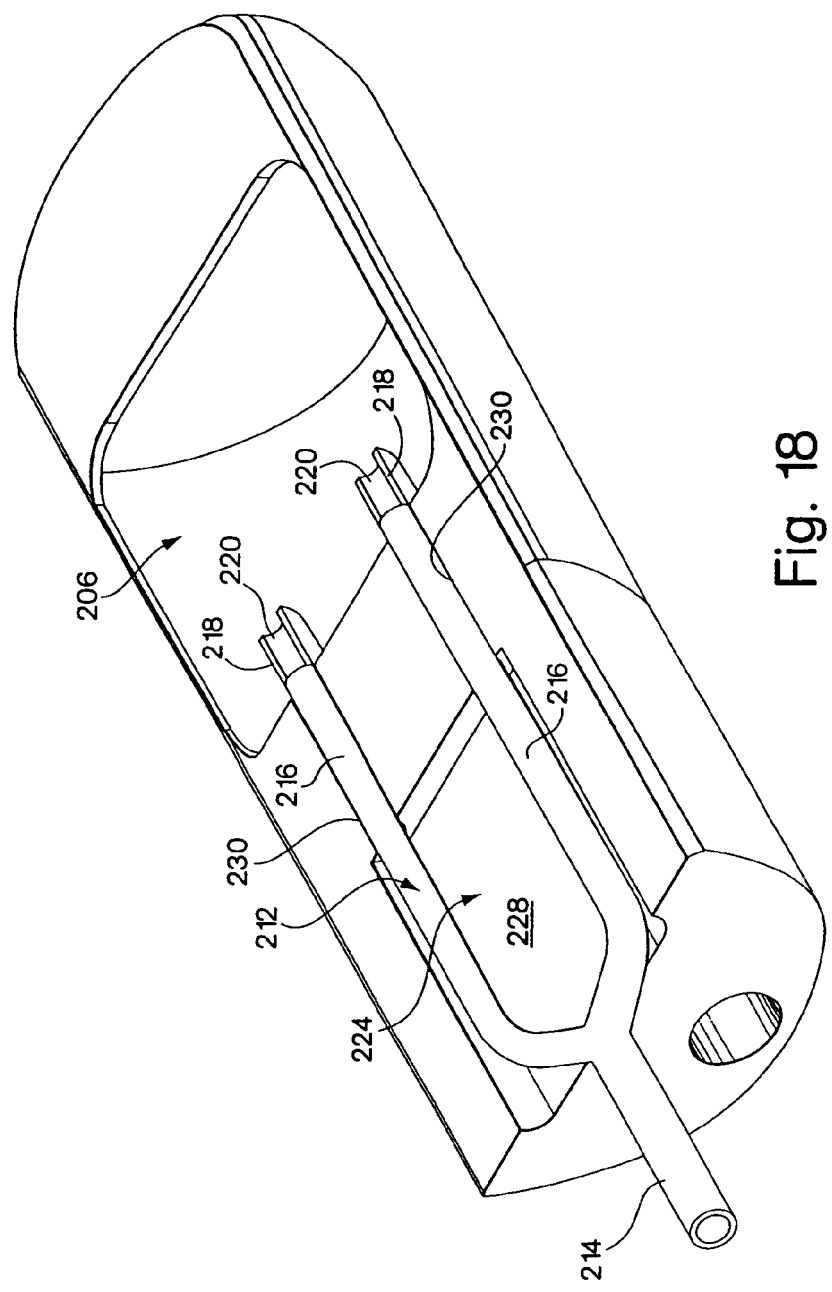
FIG. 18 is a sectional isometric view of a side-by-side multiple suction port device having a forked needle.

The forked needle 212 is slidable within the capsule and track 224, best shown in the sectional views of the capsule in FIGS. 17 and 18. The track 224 is comprised of a rectangular section 228 that accommodates the needle prongs 216 and the needle based 214 during sliding movement. Distal to the rectangular portion, the track also comprises needle guideways 230, which locate the prongs 216 of the needle in its sliding movement proximal to traversing the vacuum chamber 206. It is noted that the sectional views in FIGS. 17 and 18 do not show the partition 204, which is formed in the top surface 210 of the capsule 200. The base 214 of the fork needle may be joined to a cable 10, which extends through the working channel 3 of an endoscope 1 (as shown in FIG. 2) to control longitudinal movement of the needle.

In use, the side-by-side suture capsule 200 is advanced into the patient at the distal end of an endoscope. The forked needle 212 is withdrawn proximally so that the needle prongs 216 reside within the fork guides 230, to keep the suction ports 202 open and ready to receive tissue. The forked needle 212 is placed sufficiently proximal so that the pointed suture tags 222 are also withdrawn into the fork guides 230. Sutures 236 joined to tags 222 are also partially withdrawn into the fork guides 230 slightly and are permitted to extend outward from the fork guides and out from the suction ports 202 then extend along the endoscope and outside of the patient's body. The sutures 236 are securely fastened to the center of the suture tags 221 either by heat bonding in the case of polymer tag, or by a knot formed internal of the tag if formed of a hollow rigid material such as stainless steel. The tags are located in the tag receptacles 220 or within the inside diameter of the needle by a friction fit.

The capsule is maneuvered to the treatment site and the suction ports 202 are placed against tissue to be joined. After positioning the capsule, suction is applied through the vacuum channel 234 causing tissue to be drawn into the suction ports 202 and into the vacuum chamber 206. The partition 204 and sidewalls 208 cause the tissue to conform into two equally shaped mounds or portions, useful in forming a plication once sutures have been applied and secured. Next, the forked needle 212 is advanced distally through the tissue that has been captured and retained in the vacuum chamber 206. The prongs 216 of the distally advancing needle continue across the suction ports 202 as the pointed suture tags 222 pierce and penetrate the tissue.

After exiting the tissue portions the prongs of the needle continue distally slightly into the area of tag catches 238 located at the distal side of each suction port 202. The sutures 236 will have been drawn through the tissue along the pathway that has been created by the forks 216 of the needle 212. The tag catches are formed as notches in the top surface of the capsule that are aligned with the path of the advancing forked needle. The tags may be expelled from the needle forks on the through side of the tissue by several mechanisms. The suture catches may be sized so that the suture tags become temporarily frictionally engaged in the suture catches such that when the forked needle 212 withdraws proximally, the tags remain in the catches 238, being withdrawn from the tag receptacles 220 of the withdrawing needle. Alternatively, the suture tags may be ejected from the hollow needle forks by a distal movement of a pusher wire 11 slidable within the control cable and needle (as shown in the prior art device of FIGS. 1-3).

After the needle has been withdrawn so that both forks 216 are again concealed within fork guides 230, proximal to the suction ports 202, suction may be discontinued to release the tissue portions, now with sutures 236 passing through the tissue portions. As the tissue withdraws from the capsule and the capsule is withdrawn from the patient, suture tags 222 are pulled from the suture catches 238, overcoming the force of the frictional engagement with the sidewalls of the catches. The freed catches 222 will tend to rotate perpendicular to the longitudinal axis of the suture that is passing through the suture. Accordingly, the suture and suture tag form a T-shape that effectively anchors the suture in the tissue. The tag 222 becomes oriented to transverse to the path of the suture through the tissue so that penetration into the tissue is resisted when a pulling force is applied to the suture material in the proximal direction. Alternatively the tags 222 may be driven into securement device that remains in the patient, such as a tag lock device described in greater detail below. The free ends of the sutures passed through the two portions of tissue may then be tied in a knot that that is advanced to the suture location or may be secured by a suture lock device in order to secure and hold the tissue portions together to form a plication.

An alternative side-by-side capsule embodiment utilizes separate vacuum chambers 206 for each suction port 202 that may be opened to vacuum independently. In this embodiment (not shown in the figures), separate vacuum chambers may be formed by extending the partition 204 downward through the chamber 206 dividing it into two separate chambers that may be independently opened to negative pressure. An advantage provided by separate vacuum chambers 206 is the ability to draw tissue portions into the chambers separately and sequentially. Sequential capturing of the tissue portions permits the physician to verify that the first tissue section has been fully captured in the vacuum chamber before attempting to capture a second tissue portion. The physician may verify complete tissue capture visually by using the viewing capability of the endoscope. Additionally, the physician may capture a first tissue section then reposition the capsule slightly against the tissue to alter where the second captured tissue section will be to better orient the placement of the sutures and the configuration of the resulting tissue plication.

Figure 19:
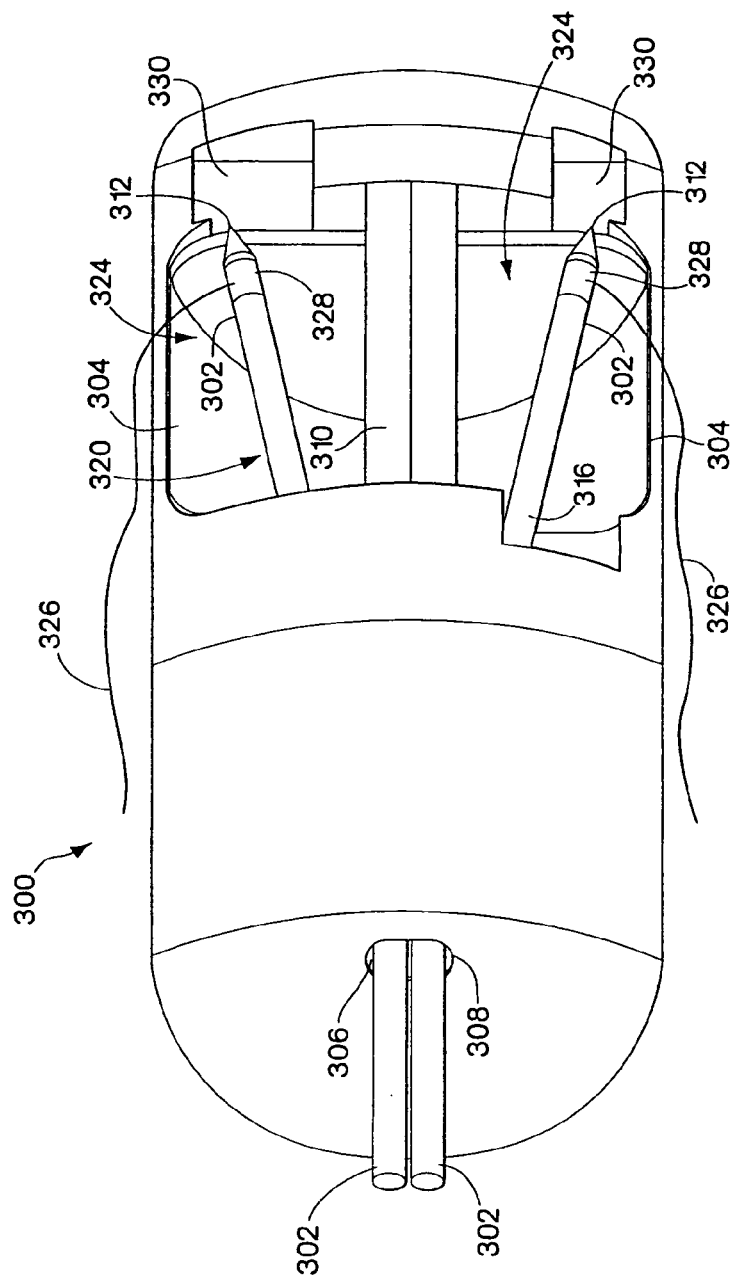
FIG. 19 is a top view of a side-by-side multiple suction port device having independently controlled needles.
Figure 20:
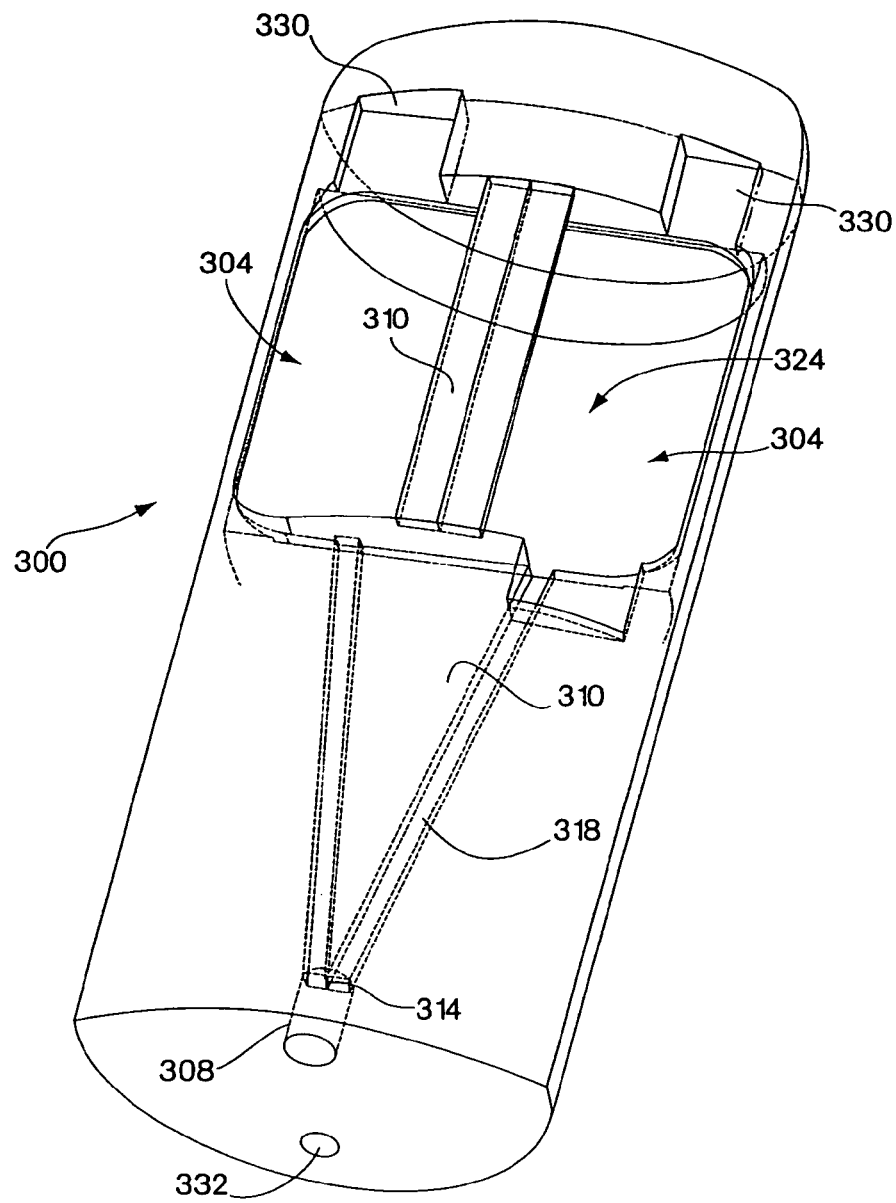
FIG. 20 is a sectional view of a side-by-side multiple suction port device having independently controlled needles.
Figure 21:
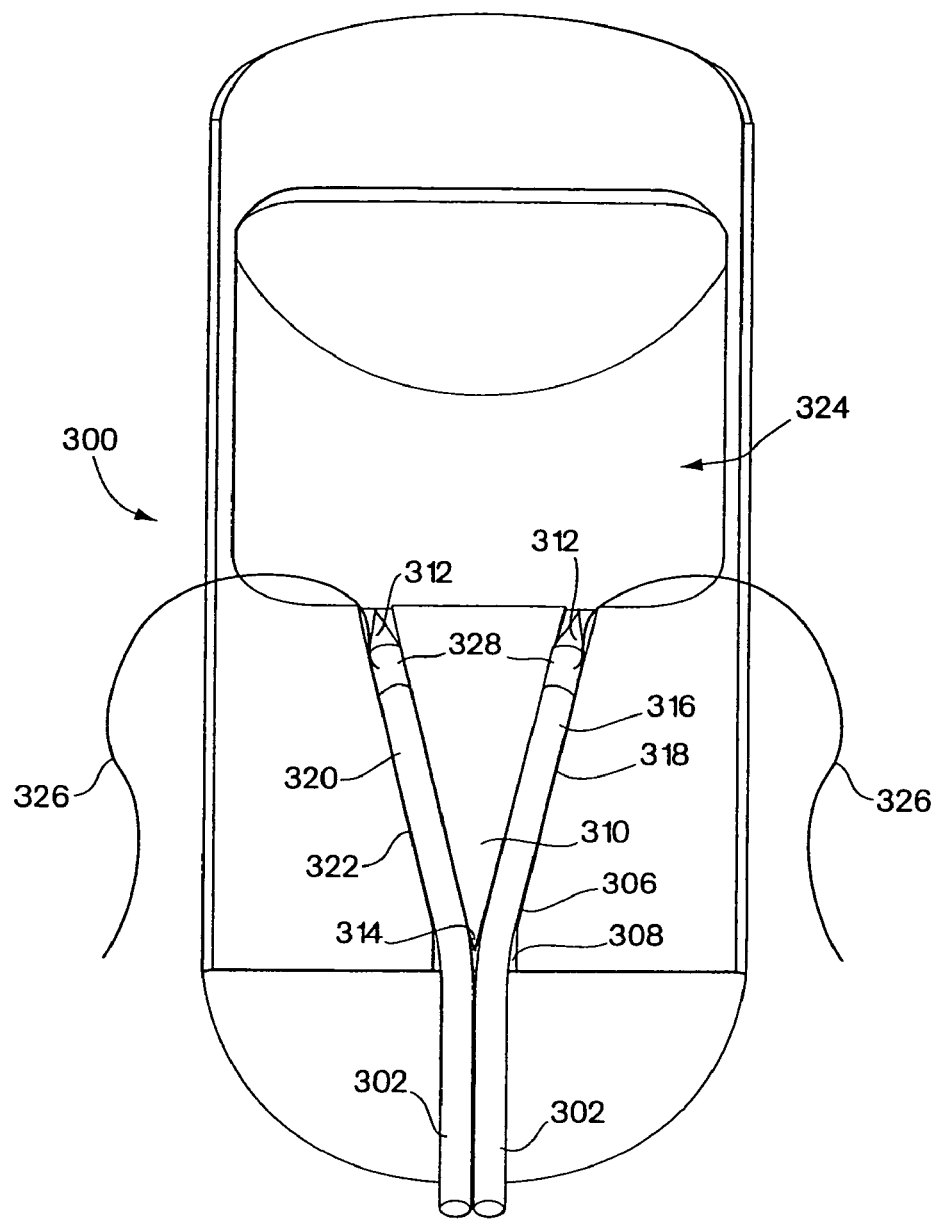
FIG. 21 is a top view of a side-by-side multiple suction port device having independently controlled needles.

In another embodiment of the side-by-side tissue apposition device shown in FIGS. 19-21, independently advanceable flexible needles are employed for each suction port. The side-by-side capsule 300 is configured substantially the same as the side-by-side embodiment described above, but defines a unique needle guide is structure that causes each flexible needle 302 to be diverted slightly from a longitudinal axis of the capsule to cross each suction port 304 as it is advanced distally. The needles 302 are longitudinally slidable through the capsule 300 within needle track 306. At the proximal end of the needle track 306, the needles lie parallel to the longitudinal axis of the capsule, located to be in alignment with the working channel 3 of the endoscope 1 when the capsule is mounted to the distal end of the endoscope. Elongate cable 10 may be joined to the proximal end of the needles 302 so that longitudinal movement can be effected from the proximal end of the endoscope, outside the patient.

During distal advancement, the needles are diverted from their path along the longitudinal axis of the capsule by a diverter 310 placed within the needle track 306, as best shown in the sectional views of the capsule in FIGS. 20 and 21. The diverter 310 creates a fork in the needle track pathway that causes the distally bound needles 302 to diverge away from the longitudinal path parallel to each other, so that they will pass across the center of the suction ports that are spaced away from the longitudinal axis of the capsule due to their side-by-side arrangement. As the piercing distal tips 312 of the parallel needles 302 approach the tip 314 of the diverter 310 with the right needle 316 will be directed into the right needle pathway 318 and the left needle 320 will be directed into the left needle pathway 322. The right and left needle pathways 318 and 322 define an internal diameter that is slightly larger than the diameter of the needles to permit sliding movement, yet provide a secure directional control over the needles as they advance through the vacuum chamber 324. The proximal end 308 of the needle track 306 defines an internal diameter that is large enough to accommodate both needles 302 for slidable movement while the needles are in close parallel arrangement, prior to reaching the diverter 310. Alternatively, the proximal end 308 of the needle track may define separate lumens extending in parallel to guide the needles.

The needles of the diverter capsule embodiment 300 may be moved independently. The proximal ends of the needles may be joined to two independently movable elongate pushing cables extending through the working channel 3 of an endoscope in place of the single elongate cable 10 that serve to move the single needle of the previously described embodiments. Two cables of a reduced diameter may be placed within a single working channel endoscope to provide independent movement of the needles. Alternatively, an endoscope having dual working channels may be used with a pusher cable for each needle 302 placed in each working channel and joined to the proximal ends of the needles to provide independent control over their movement through the capsule 300. Alternatively, the needles 302 of the diverter capsule embodiment 300 may be joined to a single elongate cable to provide tandem, unified movement of the needles through the capsule with movement of the single cable.

In use, the diverter capsule 300 is navigated to an internal tissue location within a patient at the distal end of an endoscope. The needles 302 are maintained proximally withdrawn inside the left and right needle pathways 320 and 318 during delivery. Sutures 326 extend from tags 328 frictionally located at the distal tips of the needles 312. As with the embodiments described above, the tags 328 may form the piercing distal tip of the needle that is later separated from the needle to become a cylindrical anchor that later rotates to be perpendicular to the pathway of the suture extending through the tissue. Alternatively, if the needles are hollow, the tags 328 may be frictionally held within the tip of the needle and later ejected from the needle by a pusher wire slidably contained therein as with the embodiment 200 described above. Receptacles 330 formed distal to the suction ports 304 provides space for the tags to be ejected from the needle to rotate free of the capsule after being driven through the tissue portions. Alternatively, rather than receptacles, a passageway may be formed at the distal end of the suction ports 304 that permits the tags to be ejected into a chamber at the distal tip of the capsule where the tags will become captured, in similar fashion to the embodiments and prior art devices described above in FIGS. 1-3. A further alternative embodiment comprises use of tag lock devices that are temporarily frictionally engaged in receptacles 330 and receive suture tags 326, anchoring them in the tissue after the needles are withdrawn. The tag lock devices will be described in greater detail below.

Continuing with the operation of the diverter capsule embodiment, after the capsule is navigated to a tissue location, suction is applied to the vacuum chamber 324 through vacuum channel 332 to draw tissue portions into the suction ports 304 so that the tissue becomes seated in vacuum chamber 328. In the case of a diverter capsule embodiment having separate vacuum chambers 324 for each suction port 304, tissue portions may be drawn into the suction port sequentially as vacuum may be selectively open to each of the side-by-side chambers. If vacuum is open to one of the chambers to draw in tissue to that chamber, the needle 302 corresponding to that chamber may then be advanced distally to immediately capture the tissue section without necessitating that the needle for the other chamber be activated. After one tissue section has been sucked into the suction port 304 and pierced by the needle 302 driven distally through it, the physician can be assured that the tissue section will remain captured if repositioning of the capsule is required to capture the second section of tissue in the remaining suction port. Next, vacuum is introduced into the remaining free vacuum chamber 324 to capture a second section of tissue through the suction port 304. The second needle 302 may then be advanced distally to penetrate and capture the second tissue portion. The suture tags 328 may then be ejected from the needles 312 either by a pusher wire slidably received in one or both of the needles or by frictional engagement with the receptacles 330 or tag locks as will be described below. After the suture tags 328 have been ejected on the through side of the tissue, the needles may be withdrawn proximally from the tissue and vacuum is discontinued to release the tissue portions from the device. The free ends of the sutures, which extend outside the patient's mouth may then be secured by surgical knots or suture locks to secure the tissue.

Figure 22:
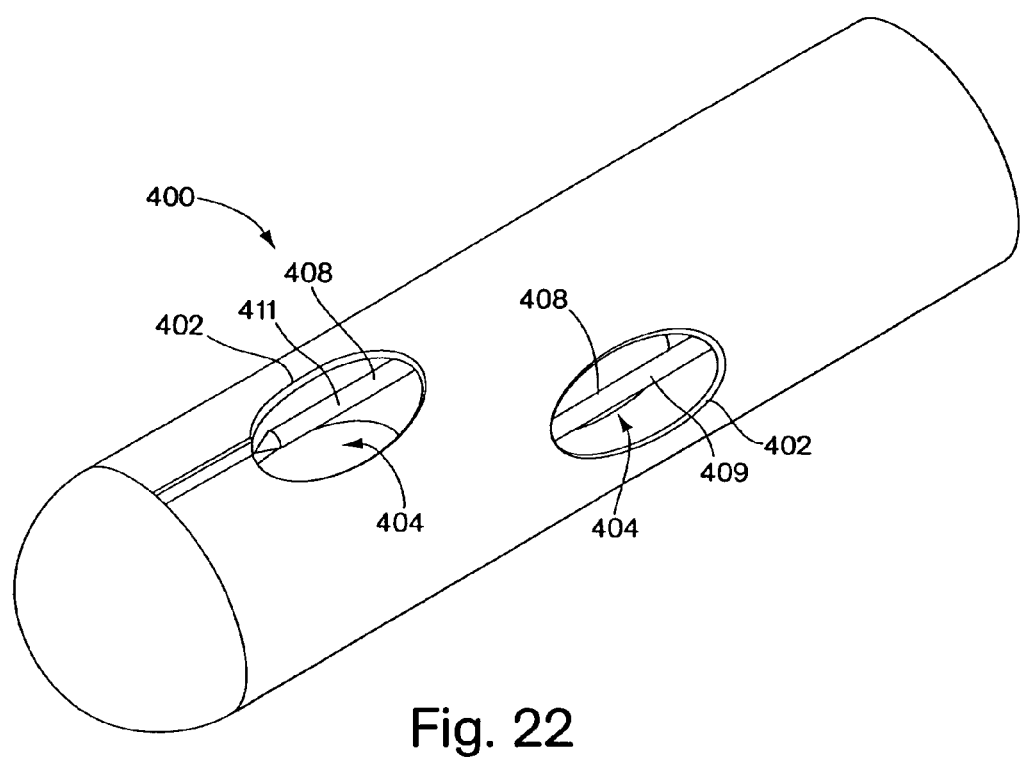
FIG. 22 is an isometric view of a tissue apposition device having multiple suction ports that are angularly and longitudinally offset.

FIG. 22 shows an alternate embodiment of a tissue apposition device having multiple suction ports that are longitudinally and angularly offset from each other. The offset capsule embodiment 400 may have a cylindrical shape having at least two suction ports 402 formed through the surface of the capsule that are spaced longitudinally on the capsule and angularly offset from each other. The exact placement of the ports on the suction chamber may be varied to obtain the preferred tissue plication shape for the given procedure. In the example of the offset capsule shown in FIG. 22, the suction ports 402 are arranged to be slightly spaced longitudinally of a distance of less than half the length of a suction port and are angularly displaced at less than 90°. This arrangement of suction ports offers a physician an alternative configuration of formed tissue plications that may better achieve the objective of the particular treatment. The arrangement of suction ports 402 is believed to be suitable for tissue plication formation useful in GERD treatment.

As with the previous embodiments, suction ports 402 open to vacuum chambers 404 into which tissue is drawn when vacuum is applied. It is preferred that in the offset embodiment 400 that the vacuum chambers 404 be configured to operate separately, each serving only one suction port 402 so that tissue can be selectively captured in the suction ports. Additionally, it is preferred that the needles 408 be separate and independently operable.

Figure 23:
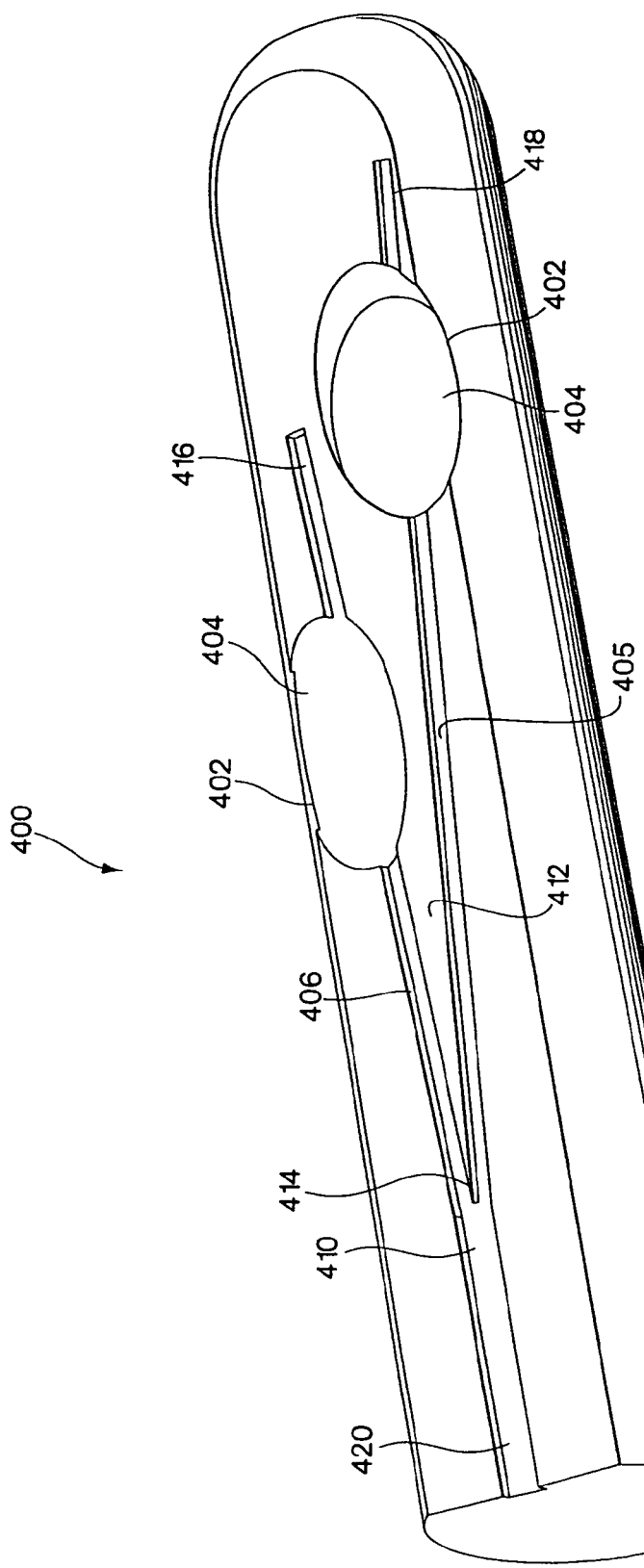
FIG. 23 is a sectional view of a tissue apposition device having multiple suction ports that are angularly and longitudinally offset.

FIG. 23 shows a sectional view of the offset capsule embodiment 400 having a diverging needle guide path 410, similar to the diverter capsule embodiment 300. As with the previous embodiment, separately advanceable needles 408 reside in parallel in the base portion 420 of the needle guide path so that the proximal ends of the needles can be joined to elongate cables 10 that extend through a common working channel 3 of an endoscope. The needle path 410 also has formed a diverter 412 that serves to direct a left needle 409 into a left needle path 406 and the right needle 411 into a right needle path 405 having been diverted into the left and right needle paths 405 and 406 during distal advancement. Proceeding distally, the needles each cross the center of the suction port to which the given needle path has been configured to access. After tissue has been drawn into a vacuum chamber 404 under negative pressure, the appropriate needle 408 may be advanced through the guide path 410 in a distal direction where it will be diverted as it passes the point 414 of the diverter 412 to enter the appropriate needle path to access the appropriate vacuum chamber containing the tissue. After penetrating one tissue section, the physician may verify that the remaining vacuum or suction port 402 is properly aligned to receive tissue, then activate the vacuum source to draw tissue into that vacuum chamber 404. During suctioning of the second tissue section, the presence of the first advanced needle through the first tissue section insures that the captured tissue section will not migrate from the capsule so that the location of the next tissue section relative to the first tissue section will be known. After the second tissue section has been sucked into the vacuum chamber 404, the second needle may be advanced through the needle path where it will be guided by diverter 412 to the appropriate needle path (406 or 405) to penetrate tissue captured in the vacuum chamber. After the tissue portions have been penetrated by the needles, a tissue securement device such as a suture carrying tag may be ejected from the needle by the mechanisms described above in connection with the previous embodiments. The needle recesses 416 and 418 defined distal to the suction ports 402 provide clearance for the needles 408 to extend slightly distal to the suction ports 402, not only to insure complete penetration of the tissue, but also to permit space for the suture tags to be ejected distally from the needle. Additionally, tag locks may be utilized with this embodiment as will be described below.

Figure 24:
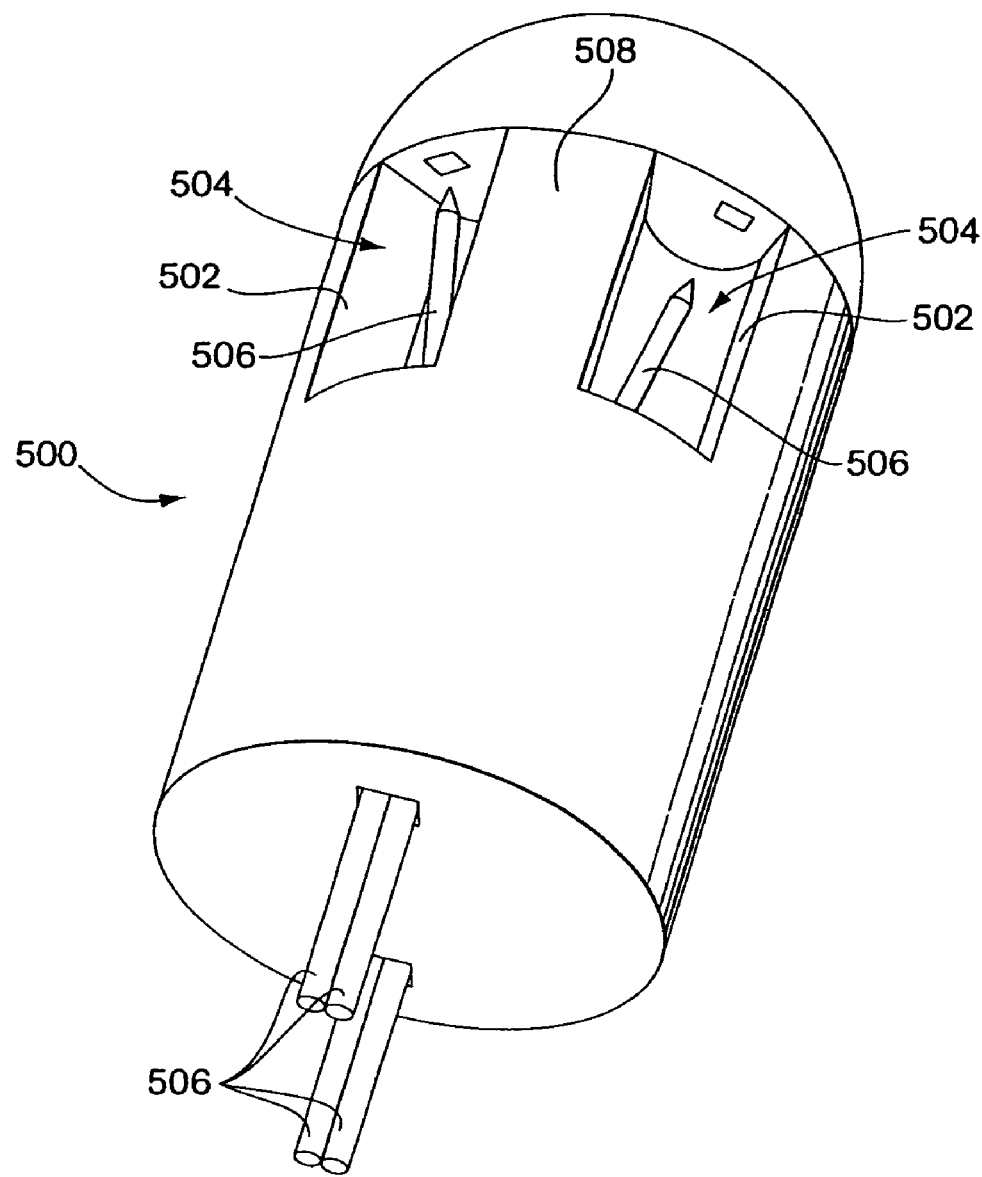
FIG. 24 is an isometric view of a tissue apposition device having four suction ports.
Figure 25:
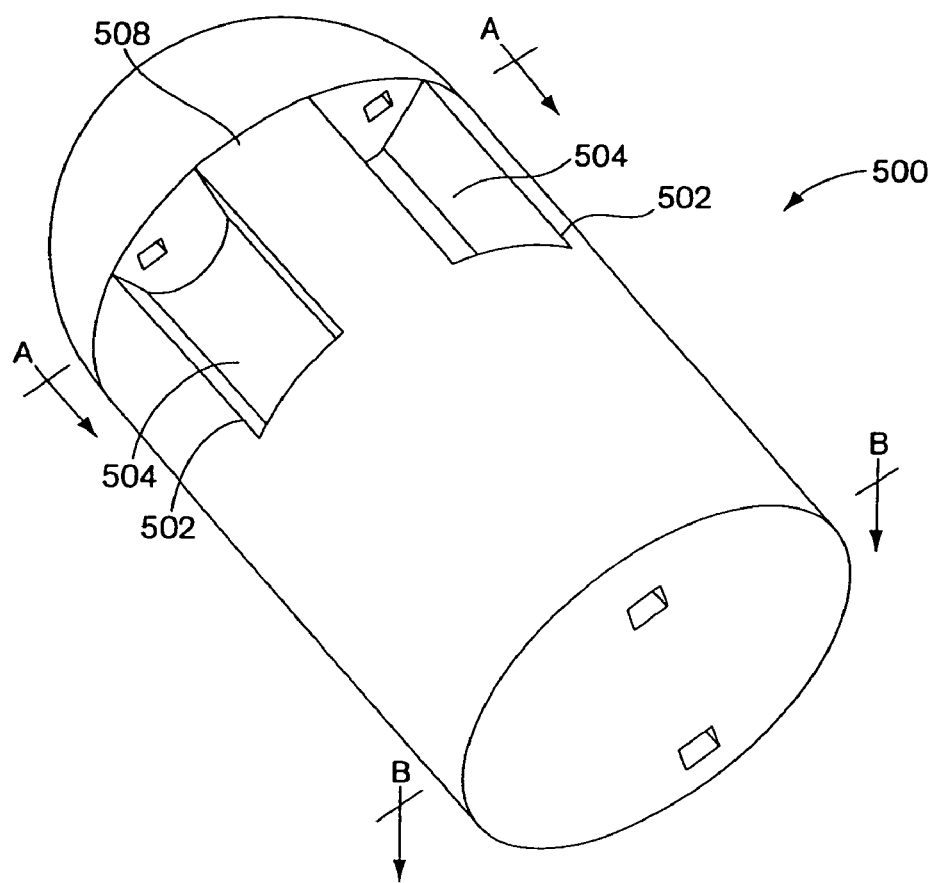
FIG. 25 is an isometric view of a tissue apposition device having four suction ports.
Figure 26:
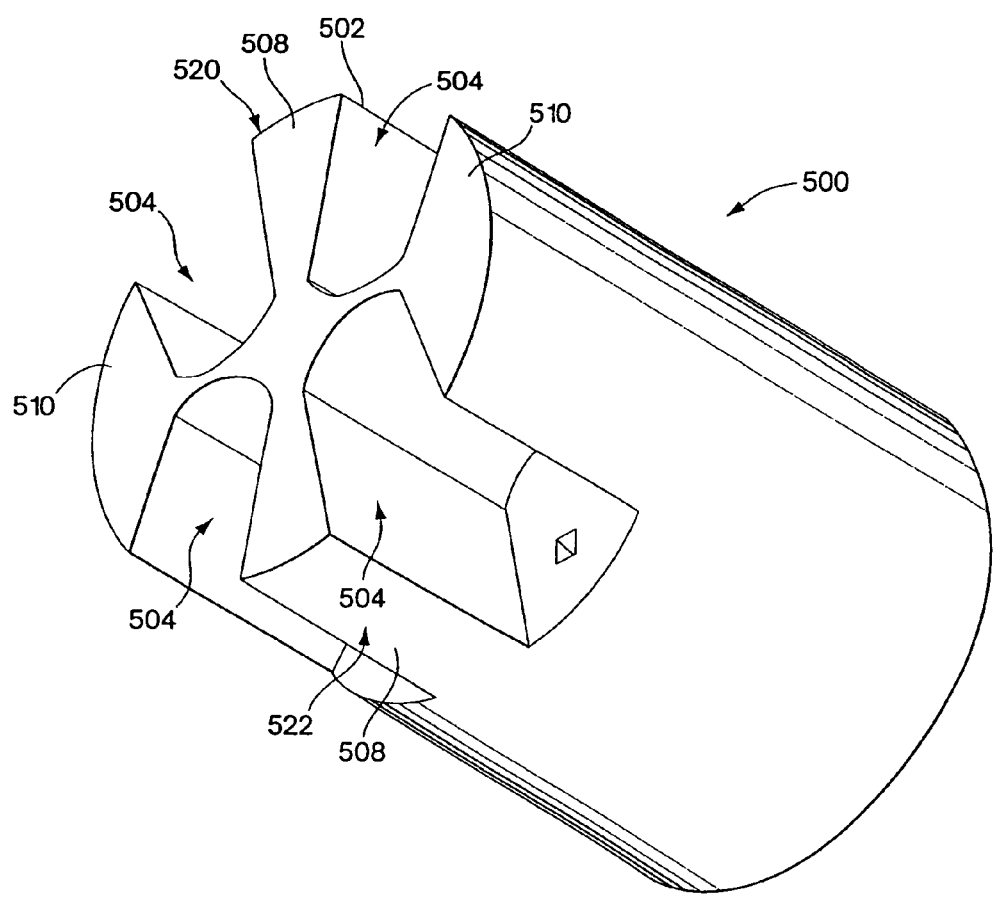
FIG. 26 is a sectional view of the tissue apposition device of FIG. 25 taken along the line A-A.

FIG. 24 shows another alternate embodiment of the multiple suction port tissue apposition device having four suction ports. The quad port apposition device 500 is similar to the side-by-side apposition device 300 described above, but comprises an additional set of two suction ports and two needles on the opposite side of the capsule. Additionally, the quad port embodiment 500 may have a cylindrical shape having a circular cross-section with suction ports 502 spaced around the circumference of the capsule. Preferably, each suction port 502 opens to an independent vacuum chamber 504 serviced by an independently operable needle 506. Preferably, the quad port capsule is used in conjunction with an endoscope 1 having multiple working channels 3 to accommodate the movement of the multiple needles 506. For example, an endoscope having two working channels 3 could accommodate two pusher cables 10 slidable within each working channel 3. Each pusher cable could then be joined to a separate needle 506 for independent movement of that needle through the capsule to a particular vacuum chamber 504. As shown in FIGS. 24 and 25, the capsule is similar to the side-by-side capsule 300 in that a partition wall 508 separates the chambers 504. As best shown in FIG. 26, a sectional view of the quad port device taken along the line A-A of FIG. 25, the capsule may be considered to have a top side 520 having two vacuum chambers 504 and a bottom side 522 having two vacuum chambers. A narrow partition 508 is employed between the two chambers oriented on one side. Wide partitions 510 define the space between the two sides. With this arrangement, the chambers 504 are not arranged 90° apart from one another but more appropriately characterized as two sets of side-by-side chambers arranged on top and bottom sides of the suturing capsule. However the capsule may be arranged in other configurations, such as equal spacing between all four vacuum chambers 504.

Figure 27:
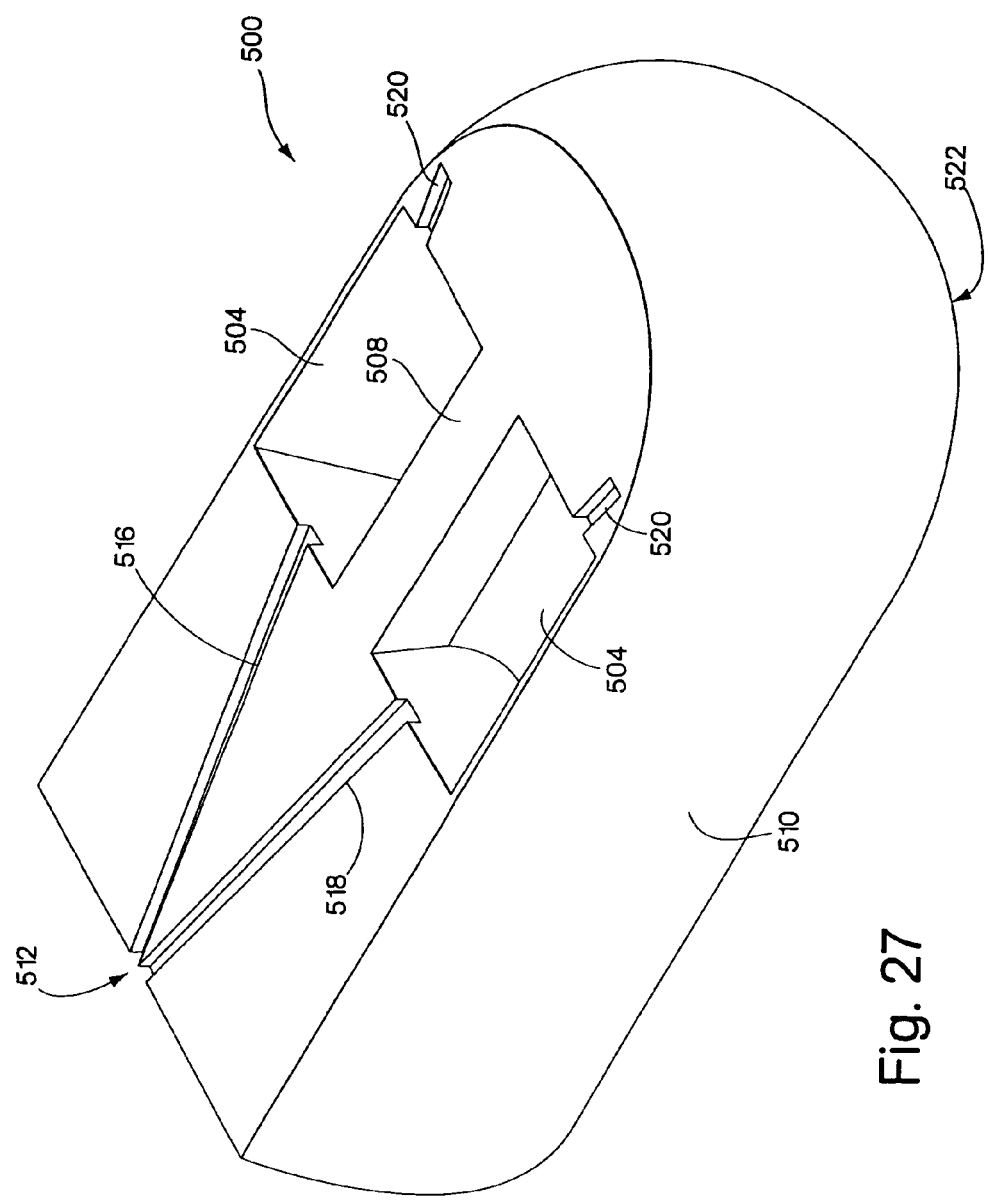
FIG. 27 is a sectional view of the tissue apposition device of FIG. 25 taken along the line B-B.

As best shown in FIG. 27, which is a sectional view taken along the line B-B of FIG. 25, a needle path 512 is defined by a diverter 514 creating a left needle path 516 and a right needle path 518 to divert the needles into the appropriate vacuum chamber 504 after tissue has been collected under the force of the vacuum. As with the embodiments described above, needle receptacles 520 at the distal side of the suction ports provide a space for the needles to advance distal of the captured tissue portions to insure complete penetration and permit suture tags to be ejected from the needles after penetration. The arrangement of the needle track and vacuum chambers 504 is mirrored on the opposite side of the capsule 500 shown in FIG. 27 to provide four independently operable suction ports and suturing needles. Independent operation of the suction port and needles is especially important in the quad port embodiment because the broad area of tissue that will ultimately be captured by the single intubation of the endoscope. Operation of the device is optimized if each section of tissue is separately drawn in and secured before suctioning of the next portion of tissue to avoid risk of inadvertently losing contact with a section of tissue already captured. However, simultaneous activation of some or all vacuum chambers to collect tissue portions is possible if the physiology of treatment area is such that the device can be positioned to have tissue adjacent each suction port simultaneously.

Figure 28:
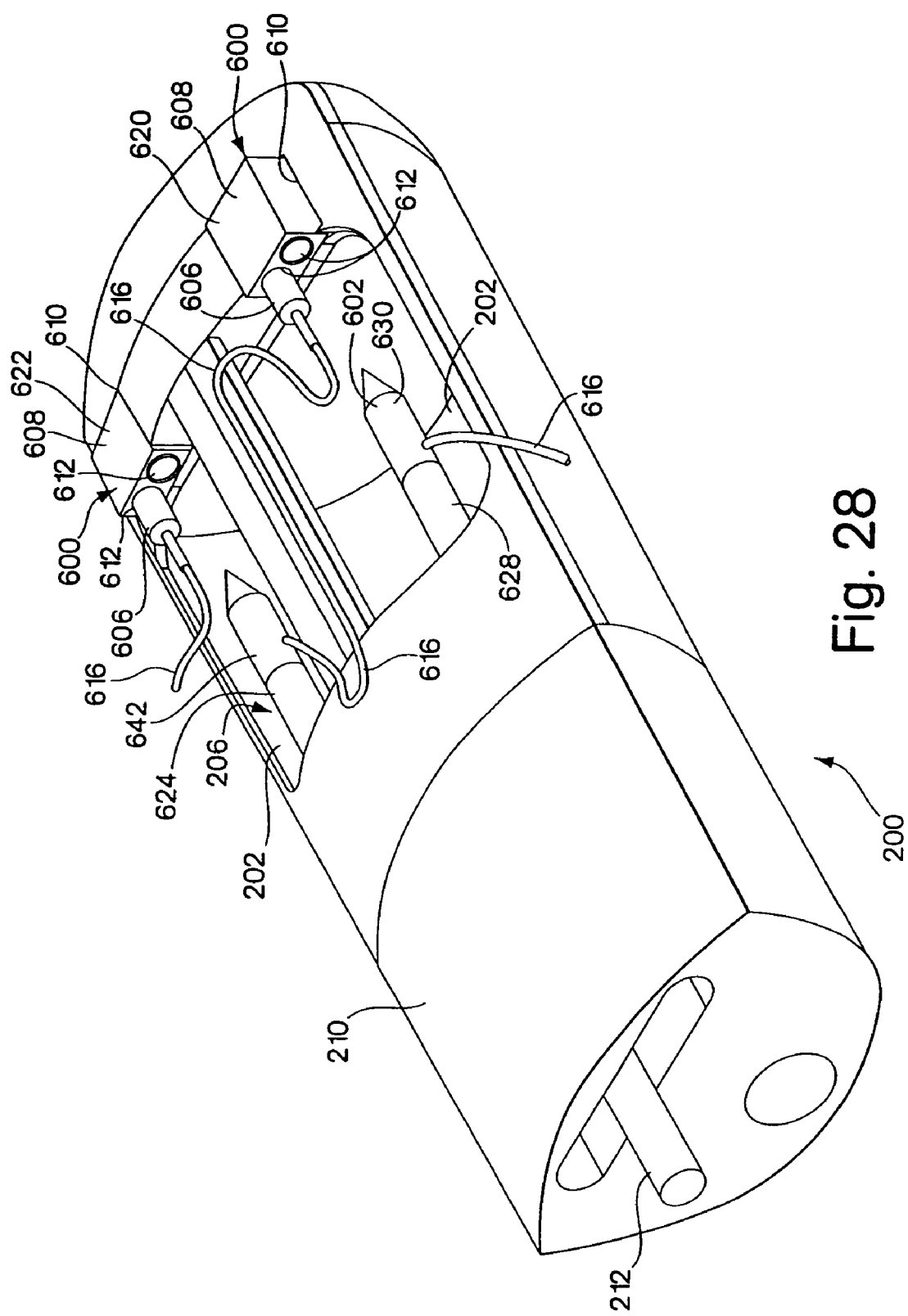
FIG. 28 is an isometric view of a multiple suction port tissue apposition device employing a suture tag lock system.

An alternative tissue securement device for the captured tissue portions is shown in FIG. 28. A tag lock device 600 may be detachably mounted to a suturing capsule of any of the embodiments described above in order to receive and hold a suture tag 602 inserted by a distally advancing needle 604. The tag lock remains at the suture site to keep the suture tag secured at the through side of the tissue so that the sutures may be manipulated to tighten connection of the tissue portions. In FIGS. 28-34, various embodiments of the tag lock 600 are shown, each illustrated in combination with the side-by-side suture capsule 200 using a forked needle 212. Each embodiment uses at least one tag lock block 608 having one or more tag receptacles 612 that each receive in frictional locking engagement a suture tag 602 or preloaded suture tag 606. In each of the embodiments, the lock block 608 is frictionally received in a tag lock receptacle 610 formed on the capsule tissue engagement surface 210 adjacent to a suction port 202. The differences between the various embodiments is defined in how many lock blocks and tags are utilized in securing a captured tissue section and the arrangement of those components on the capsule during suturing.

Figure 29A:
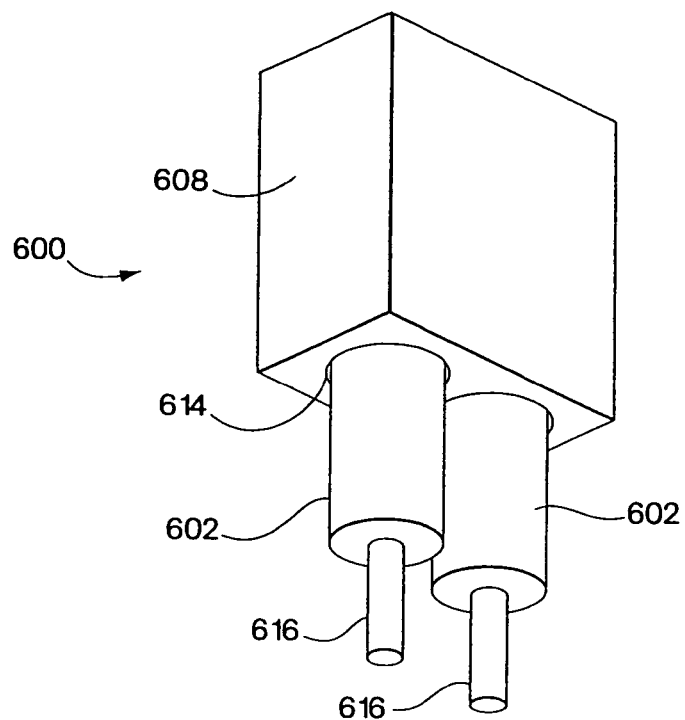
FIG. 29A is a bottom isometric view of a suture tag lock.
Figure 29B:
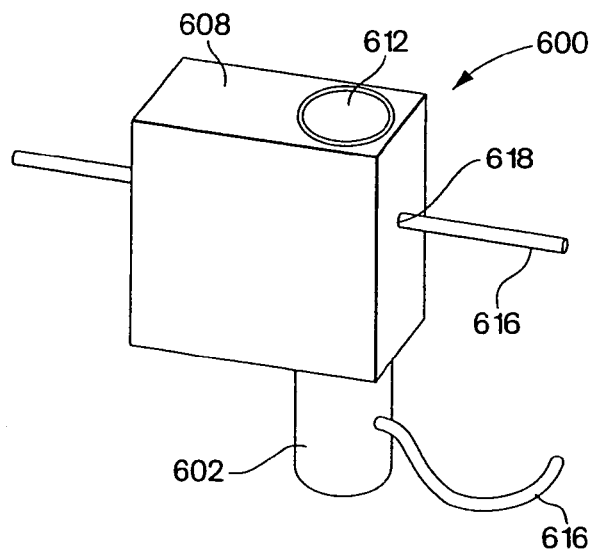
FIG. 29B is a top isometric view of a suture tag lock.

FIGS. 29A and 29B show the components of a tag lock device 600 in detail. The tag lock components are preferably made from a material that is relatively rigid, biocompatible, resistant to stress failure under compression and tension, resistant to the corrosive effects of internal bodily substances, such as acid in the stomach, and conducive to frictional engagement when in contact with like surfaces. Suitable materials may be polymers such as PEEK or metals such as stainless steel. The preferred material is PEEK. PEEK is a trade designation for a linear aromatic semi-crystalline polymer, polyaryletherketone, available from Victrex. The dimensions of the tag lock block 608 may be on the order of about 0.10 by 0.10 by 0.050 inches. The dimensions of the tag lock receptacles formed on the surface 210 of the capsule 200 approximately match the shape and size of lock blocks 608 so that they retain the lock blocks by temporary frictional engagement during delivery of the sutures to the tissue. The suture tags 602 may be on the order of 0.035 inches in diameter. The tag receptacles 612 formed into the lock block that receive the suture tags are sized closely to match the tag size so that a frictional fit is created when the suture tag 602 is inserted into the receptacle. The opening 614 of the receptacles may be flared to a slightly larger diameter to facilitate entry of the suture tag into the receptacle.

The suture material 616 is conventional surgical suture of about 0.010 inches in diameter. The suture material may be joined to the tags by heat bonding if a polymer material such as PEEK is used to form the tags. Sutures may be attached to stainless steel tags by forming the tags to be hollow and forming a hole through the surface of the tag. The suture material may be passed through the hole and knotted to create a diameter that will not pass back through the hole. This securement mechanism is also used for the prior art suture tag described in connection with FIG. 1A.

As an alternative to capturing the suture tags by frictional engagement, the tag receptacles 614 may be sized to permit the tag to pass completely through the lock block 608 and become captured on the through side of the lock block. To accomplish successful capture of the tag by this method, the suture should be joined to the center of the tag as shown in FIG. 29A rather than to the end so that the tag will tend to rotate to be perpendicular to the suture line and receptacle passage after passing through the receptacle, thereby preventing passage of the tag back through the receptacle. Attachment of the suture to the center of the tag may also facilitate temporary frictional securement of the tags to the needle, when retained either in the inside diameter of a hollow needle or in tag receptacles 220 shown in FIG. 18.

FIG. 29A shows another optional configuration of the tag lock device that permits sliding passage of a suture through the lock block. A sliding passage 618 may be formed in the block 608 in addition to the tag receptacle 612. The sliding passage may be formed through the block in any orientation relative to the receptacle 612 but should not interfere with the passage formed for the receptacle. The sliding passage should be of a diameter sufficient to permit free sliding movement of a suture. A lock block 608 formed to receive a tag 602 in the receptacle 612 and having a sliding passage 618 oriented transverse to the longitudinal axis of the receptacle and associated suture may be used in similar fashion to a lasso to tighten the tag lock against tissue with the sutures as will be described in greater detail below.

FIG. 28 shows one of several various tag lock configurations that may be employed with the multiple suction port devices of the present invention to secure tissue. Lock blocks 608 are frictionally engaged with lock receptacle 610 at the distal side of suction ports 202 of the capsule 200. The right lock block 620 is formed to have two tag receptacles 612. One tag receptacle is preloaded prior to the procedure with a tag 606 having a suture 616 that is joined with an appropriate amount of slack to left suture tag 642 that is attached to left needle fork 624. An appropriate amount of slack is such that the length of suture between right preloaded tag 606 and left tag 642 is sufficient to permit the left tag to traverse a portion of tissue collected in the vacuum chamber 206, yet hold the tissue portion securely collected after the tissue and tag are released from the capsule. Left needle fork 624 is aligned to place left tag 642 into the receptacle 612 of left lock block 622. Left lock block 622 holds another preloaded tag 606 having a suture 616 that extends out of the patient. The right needle fork 628 is aligned with the open receptacle 612 of right lock block 620. The right suture tag 630 is releasably attached to the right needle fork 628 and is aligned to be driven into the open receptacle 612 of right lock block 620 when the fork needle is advanced distally. Right tag 630 also has a suture 616 that extends outside of the patient's body.

FIG. 30 shows the arrangement of the tag lock system after the needle has been advanced distally to secure the suture tags 630 and 642 into the previously open receptacles 612. It should be recognized that in actual use, the needles will have penetrated tissue portions that were maintained in the vacuum chambers 206 during the distal advancement of the needle. After advancement of the needle, both left and right lock blocks 622 and 620 each contain one preloaded suture tag 606 and one needle driven suture tag 602 frictionally secured in tag receptacles 612. The tissue section penetrated by the left needle fork 624 will have passing through it a suture 616 that joins the left and right lock blocks 622 and 620. The tissue section penetrated by the right tissue fork 628 will have passing through it the suture 616 secured at one end in the right lock block 620 and extending at the other end outside the patient. Likewise, lock block 622, will have a free suture lead 616 that passes outside of the patient. After the tissue is released and the capsule 200 is withdrawn, the sutures may be tightened to form plications in the tissue that are best shown diagrammatically in FIG. 30A.

In the diagrammatic representation of the resulting tissue configuration shown in FIG. 30A, the left tissue portion (penetrated by the left needle fork 624) is represented by reference numeral 654 and the right tissue portion (penetrated by right needle fork 628) is represented by reference numeral 656. It is expected that the tissue segments will be secured together to form a plication by the figure eight arrangement of sutures 616, preloaded as described above, using the tag lock system 600. The sutures and tag lock device are secured tightly against the tissue by a suture lock 650 comprising a ring into which is frictionally engageable a pin to capture suture leads therebetween. It is noted that the lines shown in phantom represent suture material that is passing through the tissue.

Figure 31:
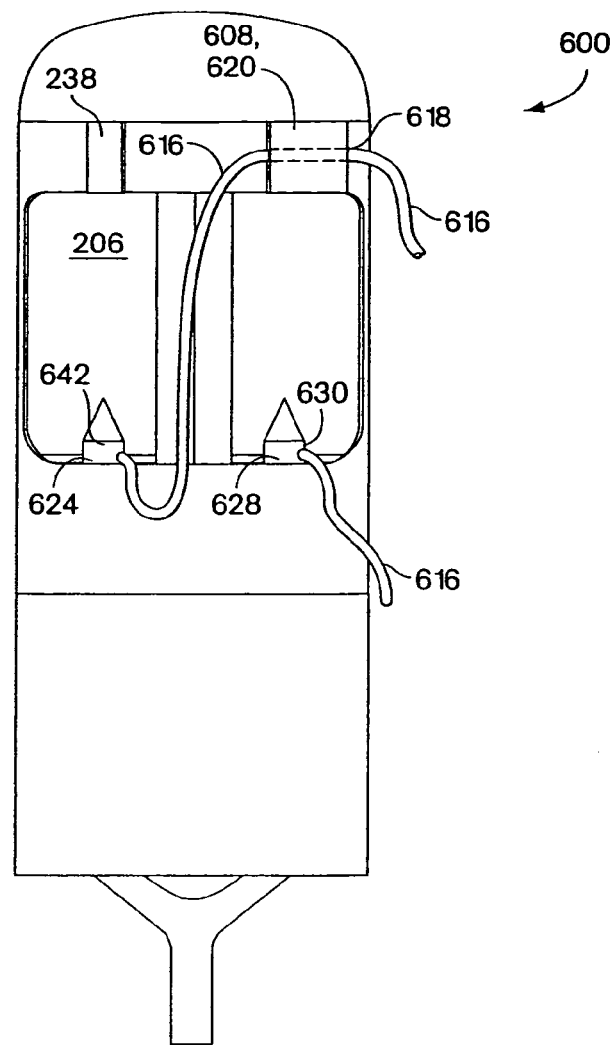
FIG. 31 is an isometric view of a multiple suction port tissue apposition device employing a suture tag lock system having a sliding suture passage.

FIG. 31 shows another possible configuration of the tag lock system 600 in which a lock block 608 having a sliding suture passage 618 (shown in phantom) is used. In particular, a right lock block 620 is placed in the lock receptacle 610 in line to receive a suture tag 630 from the right needle fork 628. The suture tag 630 loaded into the right needle fork 628 holds a suture 616 that extends outside the patient. The left fork 624 releasably holds the left suture tag 642 that is joined to a suture 616 that passes through the sliding suture passage 618 of right lock block 620. In this embodiment, the suture tag 642 of the left needle fork 624 will not be inserted into a lock block 608 upon distal advancement of the fork needle, but rather will itself serve as a T-shaped anchor after penetrating the tissue as it rotates to become perpendicular to the suture passage created through the tissue. The tag receptacle 238 is formed in the capsule body 200 to permit the tag 602 to be ejected from the needle 624 and be released from the capsule.

Figure 31A:
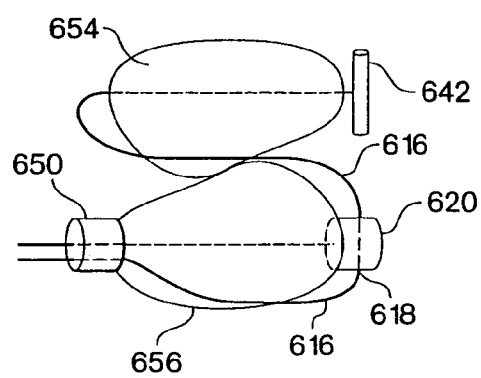
FIG. 31A is a highly diagrammatic illustration of the tissue orientation after application of the suture tag lock system and depicted in FIG. 31.

FIG. 31A shows a schematic drawing of the expected orientation of the tissue portions having received a suture tag lock system configured as shown in FIG. 31. The left tissue portion 654 will be twisted slightly as the suture 616 passing through a sliding suture passage 618 is pulled taut and secured with suture lock 650. As described above, the suture tag 642, alone, provides anchoring for the suture 616 in the left tissue section 654 while the right lock block 620, will provide the suture anchor support for right tissue portion 656.

FIG. 32 shows yet another potential configuration for the tag lock system 600 that utilizes three suture leads 616 that extend outside of the patient for securement of the internal tissue. In this embodiment, the left lock block 622 receives a suture tag 642 from the left needle fork 624 upon distal advancement of the needle. The left lock block 622 is joined to the right lock block 620 by suture 616, which passes through a sliding suture passage 618 of the right lock block 620. Right lock block 620 also receives the suture tag 630 from the right needle fork 628 upon distal advancement of the needle.

FIG. 32A shows a diagram of the expected tissue orientation after delivery of the sutures with the present tag lock configuration. Because the left and right lock blocks 622 and 620 are joined together by a suture that can slide through sliding suture passage 618, the left and right tissue portions 654 and 656 are drawn together at the ends closest to the lock block devices as the joining suture is tightened in the suture lock 650 along with the two sutures 616 passing through the tissue portions.

Figure 33:
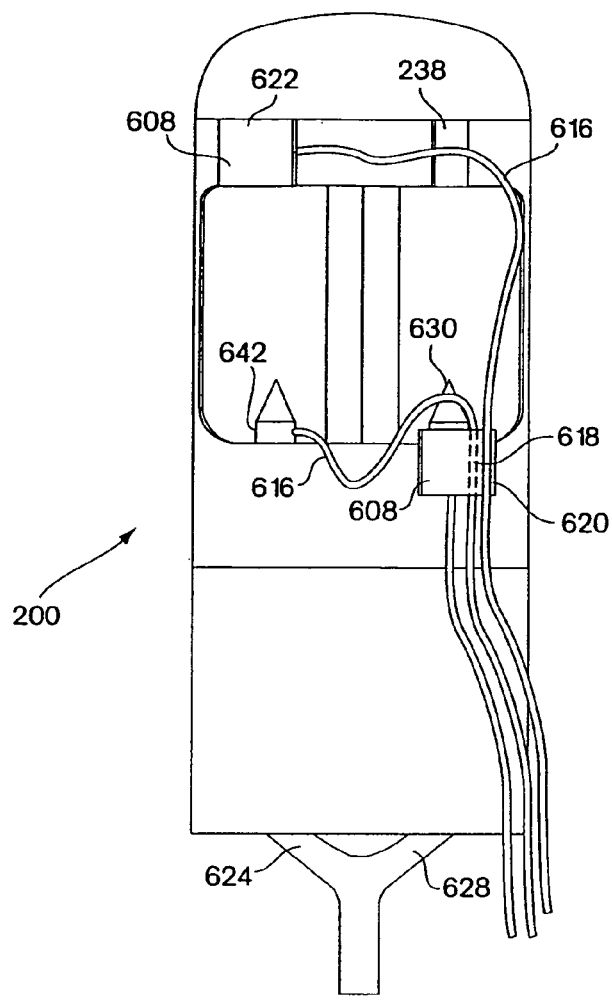
FIG. 33 is an isometric view of a multiple suction port tissue apposition device employing a suture tag lock system using three suture leads.
Figure 33A:
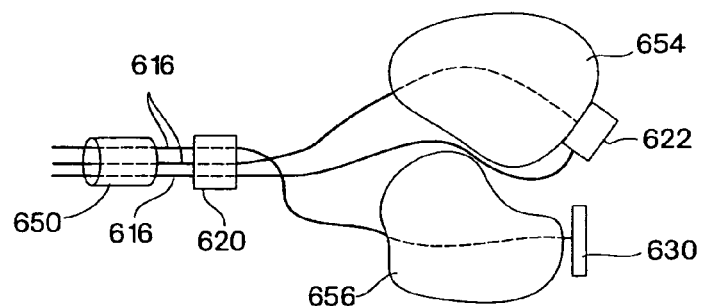
FIG. 33A is a highly diagrammatic illustration of the tissue orientation after application of the suture tag lock system and depicted in FIG. 33.

FIG. 33 shows another configuration of the tag lock system 600 in which three suture leads 616 extend from the patient for securement of the internal suture tissue. The left suture lock block 622 receives the left suture tag 642 having joined to it a suture 616 that passes through a sliding suture passage 618 formed in the right lock block 620. The right lock block 620 is releasably secured on the proximal side of the suction port rather than the distal side of the suction port as in the previously described embodiments. Additionally, left lock block 622 has fixedly joined to it a suture 616 that passes through a second sliding suture passage 618 formed into the right lock block 620. The suture tag 630 delivered through the tissue by the right needle fork 628 is received in tag receptacle 238, which permits the tag to release freely to rotate to be perpendicular to the suture line passed through the tissue so that the tag 630 serves as its own anchor. In FIG. 33A, it can be seen that the suture extending from the left lock block 622 through the sliding suture passage 618 of the right lock block 620 tends to pull the left tissue section 654 into a twisted configuration slightly when the three sutures 616 are secured by suture lock 650.

Figure 34:
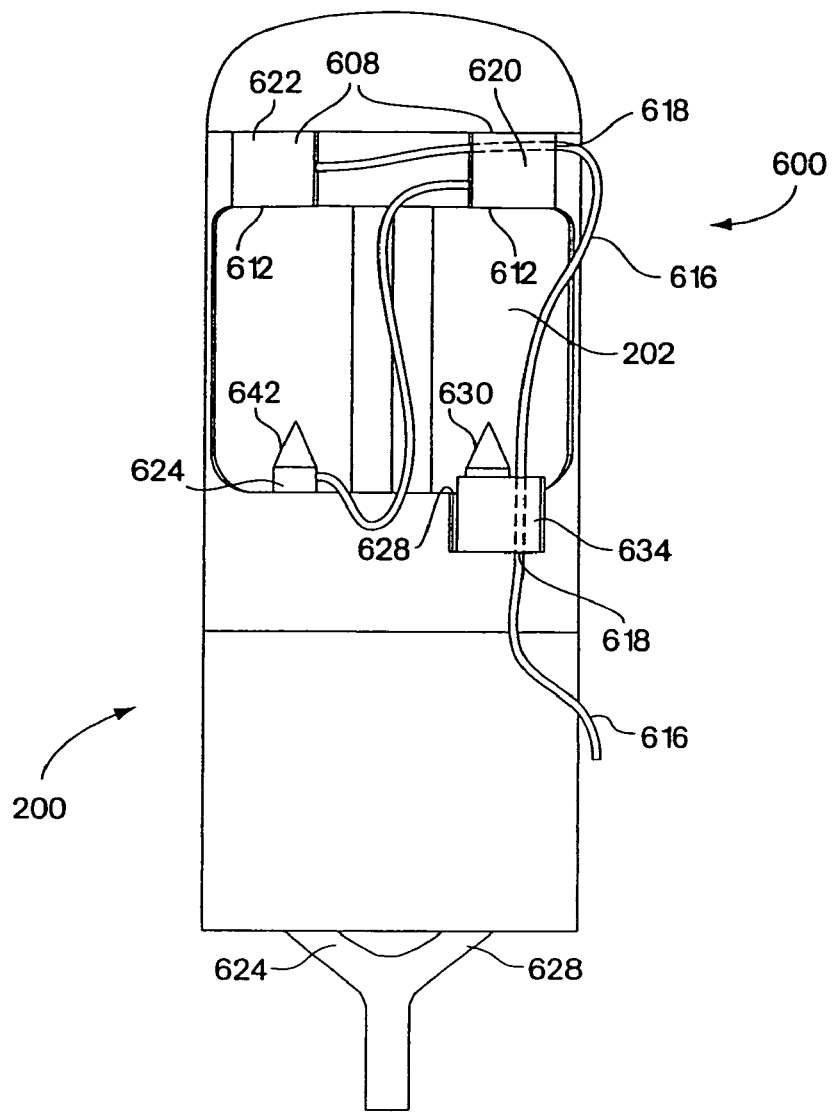
FIG. 34 is an isometric view of a multiple suction port tissue apposition device employing a suture tag lock system using a single suture lead.

FIG. 34 shows another configuration of the tag lock system 600 in which only a single suture lead 616 extends from the patient body for tightening to secure the tissue. The left suture lock block 622 has a permanently affixed suture 618 extending from its side over to right lock block 620 through which it passes in a sliding suture passage 618 formed in the right lock block. That suture continues proximally and further passes through a second right lock block 634 releasably positioned at the proximal side of the suction port 202. The suture passes through the lock block 634 via a sliding suture passage 618 and continues to extend outside of the patient. The left needle fork 624 carries a suture tag 642 that becomes secured into the left lock block 622 upon distal advancement of the needle. The suture tag 642 delivered by the left needle fork 624 has joined to it a suture 616 that is securely fastened to right lock block 620. It is noted that sutures of fixed length between lock blocks and suture tags described in this section are measured to be of an appropriate length that will accommodate the expected tissue portion size that is collected in the vacuum chamber of the capsule so as not to put too great or too little stress on the tissue portion when finally secured in a plication form.

Figure 34A:
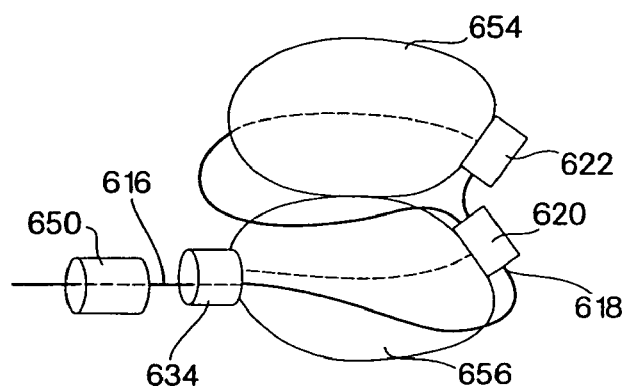
FIG. 34A is a highly diagrammatic illustration of the tissue orientation after application of the suture tag lock system and depicted in FIG. 34.

Suture tag 630 is delivered by the right needle fork 628, through the lock block 634 and into the right lock block 620 where it becomes secured in receptacle 612. Tag 630 carries with it a length of suture 616 (not shown) only sufficiently long to traverse the right tissue section 656 as the suture is also securely fastened at the other end to the second right lock block 634. FIG. 34A shows the expected tissue configuration after applying the tag lock embodiment of FIG. 34. The suture lock 650 need only be secured to a single suture 616 extending from the patient to effectively secure the entire tag lock system of this embodiment.

FIG. 35 shows the side-by-side tissue apposition device using a fork needle 200 employing a tag lock band 660 to secure suture tags 602 in place on the through side of the tissue portions penetrated by the forked needle 212. The tag lock band 660 may be flexible or rigid and may be formed from any suitable material mentioned in connection with the tag lock devices described above. The tag lock band is releasably located at the distal side of the suction ports 202 of the capsule 200 and is held in place by frictional engagement. The tag lock band 660 may have a cylindrical or rectangular shape and has two tag receptacles 662 formed through it, as is best shown in the detailed drawing of FIG. 35A. When positioning the tag lock band in receptacle 664 at the distal end of the suction port, the tag receptacles 662 align with the path of left and right needle forks 624 and 628. When the fork needle 212 is advanced distally, the suture tags 602 are driven into the tag receptacles 662 of the band 660. The tags may be frictionally engaged in the receptacles 662 or may pass completely through and rotate to be transverse to the receptacle openings to prevent passage back through the receptacles.

After the tags are ejected from the needles and the needles are withdrawn proximally, the tag lock band and captured tags may be pulled from the capsule. The tag lock band 660 is easily removed from its receptacle 664 and tag receptacles 234 are sized to easily release the tags as the capsule is withdrawn from the patient. The tag lock band offers a broader tissue contact surface area that offers better support and confinement of tissue that is being secured, which may help to form more usefully shaped tissue plications.

Figure 36:
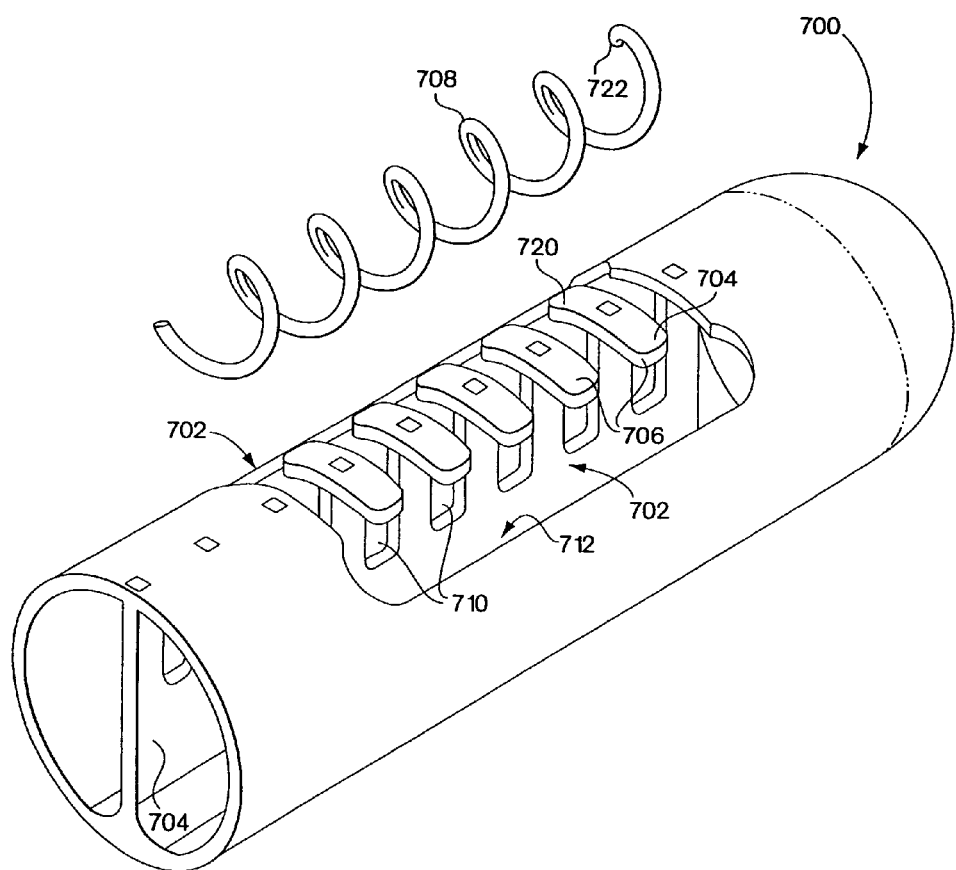
FIG. 36 is a multiple suction port tissue apposition device employing a helical wire tissue securement mechanism.

FIG. 36 shows another embodiment of a multiple suction port tissue apposition device using an alternate tissue securement mechanism. The capsule 700 uses a helical coil wire implant 708 to secure and hold captured tissue portions together. The helical coil may be formed from stainless steel wire and may be provided with a piercing sharpened tip 722 at the end of its distal most coil for piercing tissue. As with previous embodiments, the capsule 700 utilizes multiple suction ports 702 formed into the surface of a cylindrical capsule separated by a partition 704. However, in the present embodiment, the partition 704 has a series of radially extending slots 710 that serve to divide the partition 704 into a series of prongs 706 creating a comb-like partition. The slots 710 in the partition wall 704 are created to provide a passageway for the advancement of the helical coil 708 distally through the vacuum chamber 712 of the capsule as is shown in FIG. 37.

Figure 37:
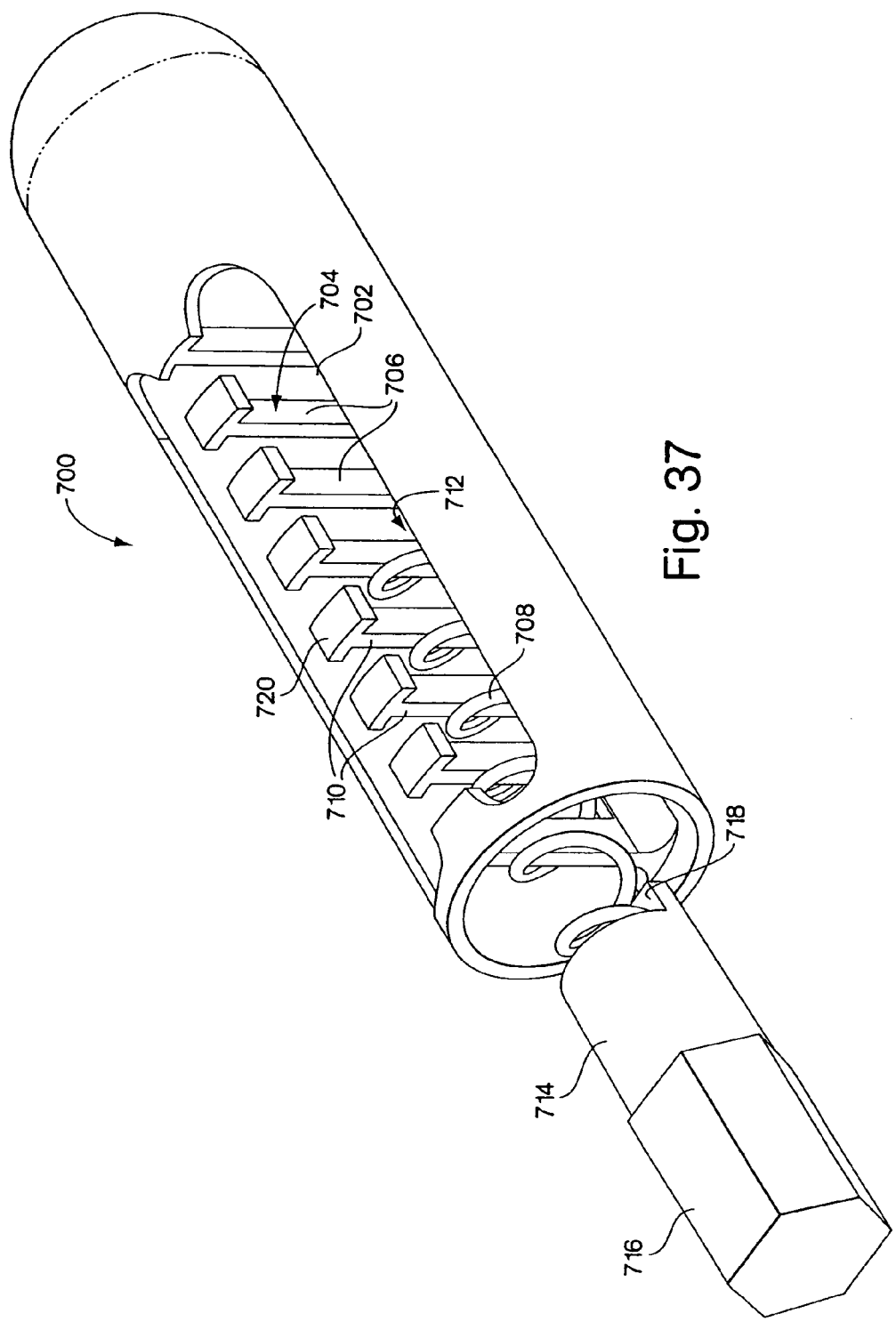
FIG. 37 is a multiple suction port tissue apposition device employing a helical wire tissue securement means.

FIG. 37 shows the helical wire 708 being advanced through the openings 710 formed in the partition 704. The helical coil advances distally and rotates as it advances to become threaded between the prongs 706 that divide the vacuum chamber 712 of the capsule. Rotational movement of the helical wire may be imparted by drive connector 714 having a drive surface 718 that contacts the proximal end of the helical wire 708 to impart a rotational force upon the wire. The drive connector 714 is rotated by rotating shaft 716 that extends through the working channel 3 of an endoscope to be rotationally and longitudinally driven, preferably, by external electric motor means. Alternatively, the shaft 716 may be manually operated by use of an operator handle connected at its proximal end that enables a physician to push and rotate the coil through the captured tissue portions.

In use, the capsule 700 is delivered to a tissue location at the distal end of an endoscope as with the previous embodiments described above. Suction is applied to the vacuum chamber 712 to draw tissue through the suction ports 702 and into the chamber. The tissue is divided into two sections by partition 704. Despite the presence of slots 710, broad surfaces 720 at the top of each prong 706 help to hold tissue back along the partition wall 704 so that it does not herniate into the openings of the slots 710. After the tissue has been captured within the vacuum chamber 712 through each suction port 702, the helical coil 708 is rotated and advanced distally through the vacuum chamber and along the center partition 704, threading into left and right tissue portions captured in the vacuum chambers to hold them together. The leading tip of the helical wire 722 is sharpened to facilitate penetration through the tissue. A stop may be provided at the distal end of the partition to prevent further rotation and distal advancement of the coil once it has been threaded through all slots that are open to the suction ports 702. After the helical wire has been completely threaded through the tissue portions, spaces 710 permit the helical wire to move upward and out from the vacuum chamber without interference with the partition 704 when vacuum is discontinued to release the tissue. It is believed that the helical wire securement device may provide a more reliable securement of the tissue portions because of its multiple penetration points through both portions of tissue in comparison to the single penetration a suture thread may provide.

In addition to securing tissue, the present embodiment may be used to endoscopically deliver implants to internal tissue locations for other purposes. Implants such as coil implant 708 may be delivered into tissue to promote bulking of the tissue area. Tissue bulking in certain regions of tissue may achieve a similar effect in the treatment of GERD that tissue plication formation achieves. Use of implants to achieve bulking may be useful in the Z-line region between the esophagus and stomach, which is easily reachable by an endoscope carrying capsules of the present invention. Additionally the implant may configured to carry bulking agents to the tissue site, by coating or other means.

In another aspect of the present invention the tissue apposition device may incorporate tissue abrasion means in the capsule body. It is believed that abrading the portions of tissue sufficiently to initiate a healing process, before securing the tissue portions into contact, will lead to combined tissue ingrowth throughout the tissue surface interface. The tissue will heal together, eventually becoming one tissue portion. Such connective strength would be an improvement over the reliability and strength of means currently available to secure tissue plications together in procedures such as endoscopic suturing for GERD treatment.

Figure 38:
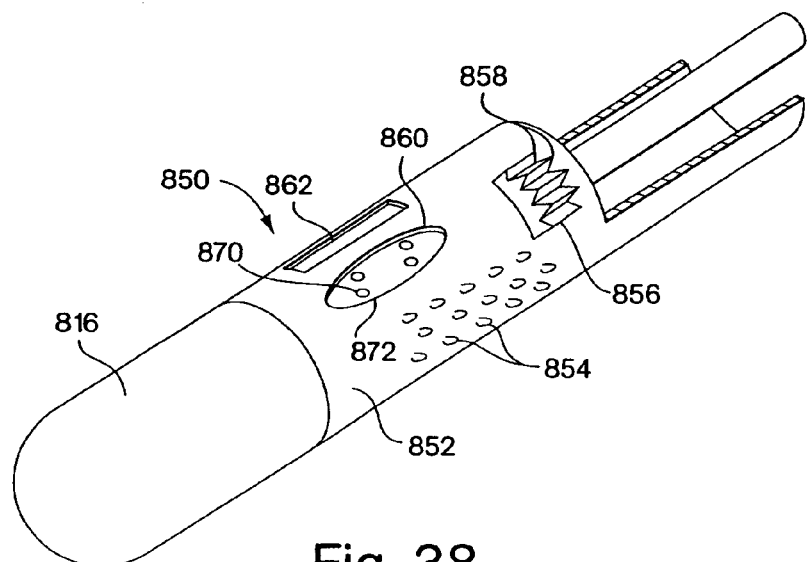
FIG. 38 is an isometric view of a single suction port tissue apposition device having mechanical abrasion means.

FIG. 38 shows an embodiment of a single suction port apposition device 850 having mechanical abrasion means on its external surface 852. Though the abrasion means can be implemented on any configuration of single or multiple suction port device, examples of the abrasion means are illustrated in connection with a single port device for simplicity. The mechanical abrasion means comprises a plurality of surface ridges 854 formed directly into the surface of the device and located adjacent the suction port 860 to score tissue lying near the chamber. Additionally, mechanical abrasion means may comprise an abrasion block 856 having a plurality of sharp protrusions 858 to frictionally abrade the tissue adjacent the suction port. With the abrasion block, the rough surface need not be formed directly into the material of the capsule body, but may be applied later during a secondary operation. The mechanical abrasion means may be actively rubbed against the tissue by moving the device back and forth to score the tissue.

It is noted that with the mechanical abrasion means, as well as with all abrasion means discussed herein, light vacuum is applied at the vacuum chamber to hold tissue in or against the suction ports and in contact with the surface 852 of the device 850 during the abrasion activity. Holding the tissue against the device not only insures that abrasion takes place, but also insures that the abrasion is applied to the tissue surfaces that will placed into contact with each other when the tissue portions are joined. After the abrasion action is complete, a full vacuum is applied to fully draw tissue into the vacuum chamber for tissue securement means attachment such as by needle and suture or staple placed through the tissue or other form of tissue adhesion.

Alternatively, or in addition to, the mechanical abrasion caused by structural elements applied to the capsule body 852, abrasive substances may be ejected from the capsule through an ejection port 862 arranged near the suction ports. Abrasive substances include salt or sugar or any biocompatible crystalline substance capable of flowing adequately to be injected through a tube running the length of the endoscope and being ejected through the small port 862. The substance may be carried in an aqueous media to facilitate delivery. It is expected that the presence of the abrasive substance will abrade the tissue adequately through its motion rubbing against itself and against the device to initiate a healing response.

Figure 39:
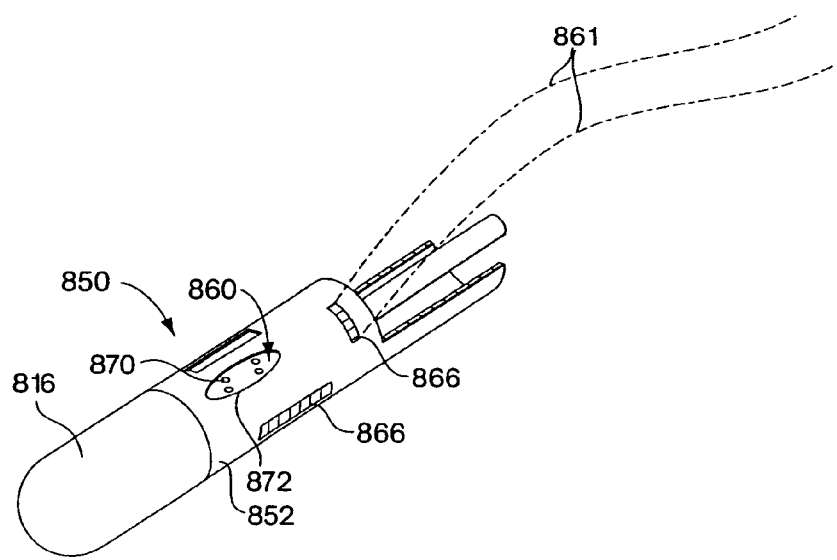
FIG. 39 is an isometric view of a single suction port tissue apposition device having radio frequency abrasion means.

FIG. 39 shows an isometric view of another single suction port tissue apposition device displaying various types of abrasion means on the capsule body surface 852 adjacent the suction port 860. Specifically, the capsule body surface 852 has several radio frequency (RF) transmitting elements 866 located around the suction port, which holds the subject tissue. The RF energy can be transmitted to the element 866, from a source outside of the patient, through small wires (not shown) that are insulated and extend through a channel of the endoscope 1. RF is believed to provide a level of energy that is well suited to creating the light injury desired to initiate the healing process in tissue. As mentioned above, it is desired to only damage or destroy the mucosal layer of tissue in this process.

Alternative means can be used for abrading the tissue with elements, such as element 866 that transmit other types of energy such as laser, ultrasonic or electrical energy. In the case of laser energy, an optical fiber can be extended through the endoscope to transmit the laser energy to a lens on the capsule surface. Ultrasonic energy may be transmitted through a small vibratory horn element, also positioned on the surface of the capsule, adjacent the suction port. Electrical energy, which injures the tissue by heat generated from electrical resistance at the element 866 may be transmitted from a source outside the patient through small wires led through a channel of the endoscope, as can be arranged for the transmission of RF energy or ultrasonic energy.

Chemical abrasion is also possible with the above-described devices. To utilize chemical abrasion, a chemically abrasive substance such as hydrochloric acid of a greater concentration than which naturally occurs in the stomach may be ejected from a port adjacent the suction port similar to port 862 discussed above with reference to FIG. 38.

Utilizing abrasion techniques in conjunction with a single suction port tissue apposition requires that the procedure be carried out in a specific manner in order to achieve the desired result of tissue segments healing together and bonding as one. Specifically, a tissue portion is first captured by the capsule body by applying light pressure through the suction port 860. The vacuum is achieved through suction ports 870 at the bottom of chamber 860, which are in communication with vacuum lines connected to a vacuum source external to the patient. A light vacuum applied should be sufficient only to hold the tissue against the opening 872 of the suction port, without sucking tissue inside the chamber. With the tissue held against the surface 852 of the capsule, the abrasion mechanism can be activated with assurance that it will be in contact with the tissue and that the tissue will not move relative to the abrasion mechanism. After the abrasion is complete, the tissue may be sucked into the vacuum chamber under full vacuum and a tissue securement device applied such as a suture, permanent tag or staple as is described in the prior art.

The tissue abrasion mechanism should be spaced from the suction port an appropriate distance so that when the tissue is later sucked completely into the chamber, and the suture is passed through the tissue portion, the abraded tissue will be near the suture entry point or otherwise in an area on the tissue surface that will be placed in contact with other abraded tissue when the plications are secured together. After a tissue securement device has been placed through the collected tissue, the vacuum may be terminated to release the tissue from the device, and the device moved to an adjacent area of tissue where the same process will be undertaken. After the second tissue securement device is placed through the second tissue portion, the tissue securement devices may be joined together by a surgical knot or suture lock component to hold the tissue plications together as a group. It is between these plications that tissue ingrowth and bonding is desired to supplement the connective force of the tissue securement device (suture, permanent tag or staple). Accordingly, the second and subsequent tissue treatment sites should be selected carefully so that the abrasion and tissue securement device are positioned in such a manner that the several tissue portions will align and have an opportunity to heal together. Ensuring proper alignment of the multiple tissue portions is made easier when the abrasion means is employed with a multiple suction port tissue apposition device as is described below.

Figure 40:
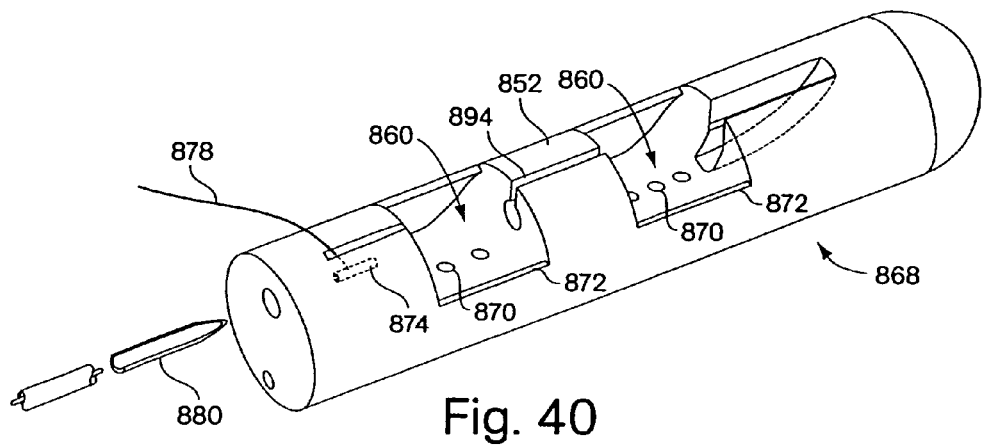
FIG. 40 is an isometric view of a dual suction port tissue apposition device without tissue abrasion means.

As shown in FIG. 40, a multiple suction port apposition device is similar in construction to the single chamber device, but accepts two tissue portions under suction simultaneously. A detailed discussion of various embodiments of multiple suction port apposition devices is provided above. All embodiments may employ the tissue abrasion means discussed here. A multiple port device is the preferred platform for implementing the tissue abrasion means because it facilitates placement of the tissue abrasion between the two adjoining plications of tissue that are to be bonded together through tissue healing. Abrasion placement is facilitated because both tissue portions are captured simultaneously in fixed positions by vacuum chambers 860 during application of the abrasion technique.

Figure 41:
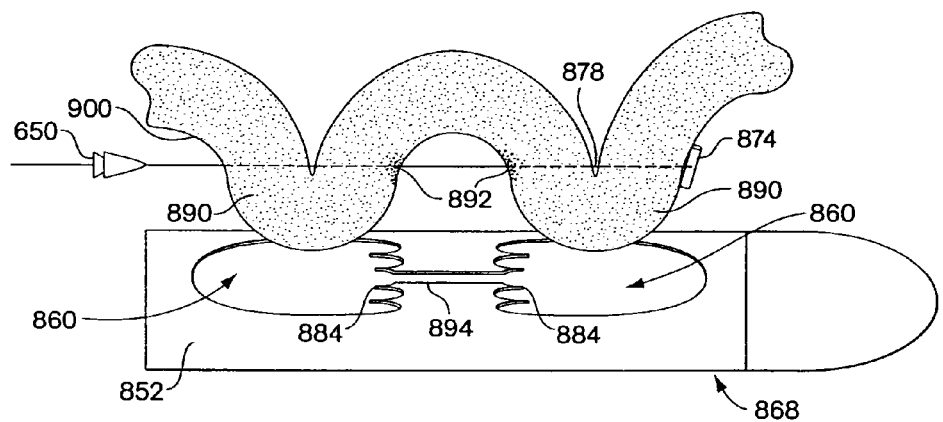
FIG. 41 is an isometric view of a dual suction port tissue apposition device having mechanical abrasion means.
Figure 42:
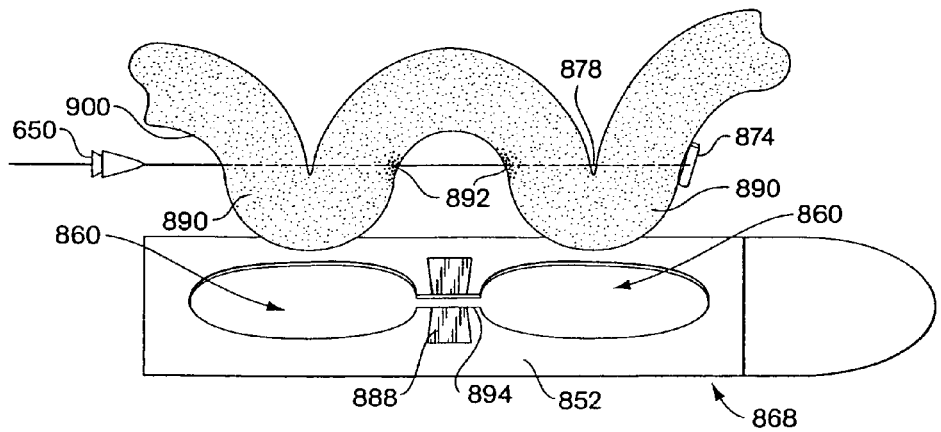
FIG. 42 is an isometric view of a dual suction port tissue apposition device having electrical and radio frequency abrasion means.

As shown in FIG. 41, a dual suction port suturing capsule 868 may be modified to have mechanical abrasion elements formed directly on the adjacent ends of the suction ports 872. Barbs 884 are formed on the port openings to achieve mechanical abrasion. FIG. 42 shows use of a RF transmitting element 888 located centrally between the two suction port openings 872. Positioning of the abrasion means near the center of the two suction ports results in the abraded tissue becoming aligned and placed in contact after the two tissue portions 890 are formed in the vacuum chambers 860 and a tissue securement device such as a suture 878 with permanent suture tag 874 is inserted through the two portions as is shown in FIGS. 41 and 42. When the suture 878 is pulled tight and the two plications are brought in contact, abraded tissue areas 892 will be placed in contact and tissue ingrowth between the abraded areas 892 will be facilitated.

Accordingly, the process for utilizing the multiple suction port tissue apposition devices with abrading means as shown in FIGS. 40-42 is discussed below. First, the dual chamber device is brought into contact with subject tissue and light vacuum applied through the suction port 872 of each vacuum chamber 860 to draw tissue into secure contact with the top surface 852 of the capsule. Next, the tissue abrasion mechanism is used to abrade tissue area lying between the two areas 890 of tissue captured over the vacuum chambers 860. Note that, although mechanical means 884 and RF means 888 are shown in FIGS. 41 through 44, any of the previously discussed abrasion means may be applied through the dual suction port device in similar fashion to that described in connection with the single suction port device above.

After the tissue abrasion is complete, full vacuum may be applied through the suction ports 872 to draw the tissue portions 890 fully into each vacuum chamber 860. The needle 880 may then be advanced through the double folds of tissue simultaneously, carrying the suture 878 and suture tag 874 through the two double fold portions of tissue. After the tag is ejected on the through side of the tissue and the needle 880 is withdrawn, the vacuum may be discontinued to release the double folds of tissue or plications 890 newly formed by the suction into the vacuum chamber. The securement mechanism for the anchored suture will later be tightened to draw the plications into close contact.

After the tissue is released from the device, the suture material 878 passes through channel 894 formed between the suction ports to permit release of the system in the in-line embodiment of FIG. 40. Later, a suture lock such as the two-piece plug and ring frictional lock member 650 shown in FIGS. 30A-34A and 41 and 42 may be advanced along the suture 878 to the proximal side 900 of the tissue. For a complete discussion of suitable suture lock devices, see co-pending PCT patent application entitled "Suture Locks, Delivery Systems and Methods" filed Mar. 5, 2001. The suture 878 can be pulled tight through the suture lock and the lock engaged to hold the suture taut with the tissue plications 890 sandwiched between abraded regions 892 held in close contact to promote healing between them. The tissue is held tightly together because suture tag 874 and suture lock 898 serve as anchors on both sides of the double plicated tissue with the suture 878 in tension between them.

Because the tissue healing that will occur at tissue areas 892 is believed to ultimately bond the tissue portions 890 together, the suture material 878, tag 874 and lock 650 may be fabricated from biodegradable materials such as polymers of the poly-l-lactide family, configured to degrade after sufficient time for healing has occurred.

Figure 43:
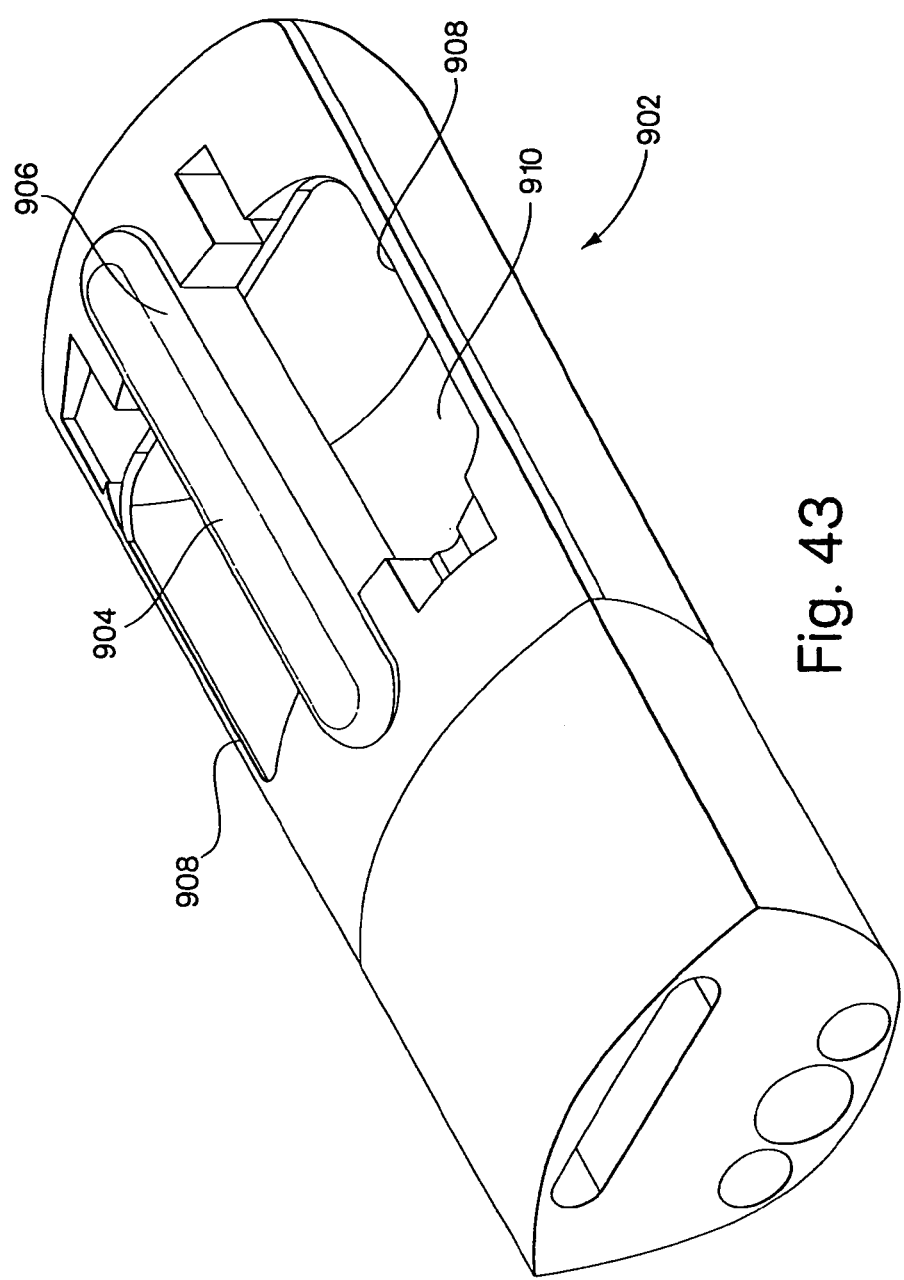
FIG. 43 is an isometric view of a side-by-side multiple suction port tissue apposition device having tissue abrasion means.

FIG. 43 shows a side-by-side multiple suction port apposition device 902 having an abrasion means 904 integrated with a partition 906 that divides the suction ports 908. In the figure, the abrasion means 904 comprises an RF energy transmitting source integrated into the partition 906. The partition may include a lens through which RF energy is transmitted to tissue. Specifically, the abrasion means 904 will contact the area directly between tissue portions that are to be joined after release from the vacuum chamber 910 of the capsule. However, other types of tissue abrasion means, such as those described above may be employed in the partition 906.

Figure 44:
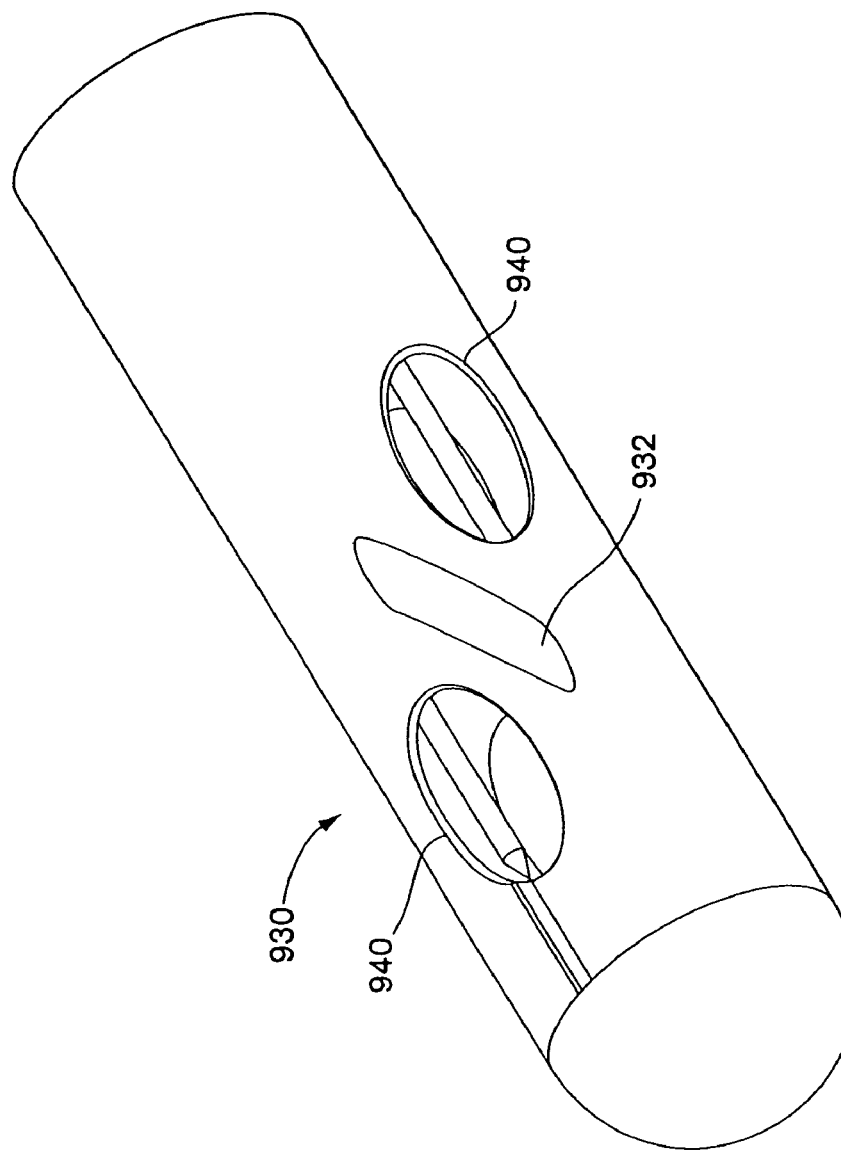
FIG. 44 is an isometric view of a tissue apposition device having multiple suction ports that are angularly and longitudinally offset and having tissue abrasion means.

FIG. 44 shows yet another embodiment of the tissue apposition device having multiple suction ports 930 employing abrasion means 932. As with the embodiment described in connection with FIG. 43, the abrasion means may comprises an RF energy transmitting element 932 positioned midway between two suction ports 940. In this embodiment, the suction ports are angularly and longitudinally offset and do not form a uniform partition between them as was defined in the previous embodiment. However, the abrasion means may be positioned on the apposition device at any point between suction ports that will experience contact with the tissue surfaces that are to be joined during the procedure. As noted above other types of abrasion means may be employed in the location of the RF means 932.

From the forgoing it should be understood that novel and useful tissue apposition devices employing multiple suction ports and methods for their use have been provided. Various mechanisms and methods for tissue capture and tissue securement that are compatible with the apposition devices have also been presented. It should also be understood that while the inventive embodiments have illustrated in the context of forming tissue plications for GERD treatment, the invention may be used in a variety of other endoscopic procedures where tissue manipulation is required. Examples include: segregating portions of the stomach to reduce it's size in obese patients; delivery of radiopaque elements for use as fluoroscopic markers used to identify sections of cancerous colon that need to be resected by a surgeon; attachment of sensor devices, such as pH, to the gastro-intestinal wall; closure of perforations or ulcers; and creation of anastomoses.

It should be understood however, that the foregoing description of the invention is intended merely to be illustrative thereof and that other modifications, embodiments and equivalents may be apparent to those who are skilled in the art without departing from its spit. Having thus described the invention what we desire to claim and secure by Letters Patent is:

The invention claimed is:

1. A method of stomach reduction, the method comprising: endoscopically segregating portions of a stomach by performing acts of:
   (a) endoscopically abrading a surface of at least two tissue portions of stomach tissue; and
   (b) endoscopically securing the surfaces of the at least two tissue portions of abraded tissue together and in contact with each other.

2. The method according to claim 1, wherein act (a) is performed prior to act (b).

3. The method according to claim 1, wherein act (b) is performed with an endoscopic apposition device.

4. The method according to claim 3, wherein act (a) is performed with the endoscopic apposition device.

5. The method according to claim 3, wherein the endoscopic apposition device includes at least one suction port, and act (b) includes suctioning the stomach tissue into the apposition device through the suction port.

6. The method according to claim 5, wherein the endoscopic apposition device includes at least one needle with at least one suture carried by the needle, act (b) includes advancing the needle and the suture through the captured tissue.

7. The method according to claim 6, wherein acts (a) and (b) include abrading a surface of a first tissue portion of stomach tissue, placing the at least one suture in the first tissue portion, abrading a surface of a second tissue portion, placing the at least one suture in the second tissue portion, and securing the at least one suture to bring the abraded surfaces of the first and second tissue portions into contact.

8. The method according to claim 6, wherein act (b) includes securing the at least one suture with a suture clip.

9. The method according to claim 1, wherein acts (a) and (b) are all performed during a single endoscopic intubation.

10. The method according to claim 1, wherein portions of the stomach are segregated to treat obesity.

* * * * *

UNITED STATES PATENT AND TRADEMARK OFFICE
CERTIFICATE OF CORRECTION

PATENT NO. : 8,152,821 B2  
APPLICATION NO. : 12/070809  
DATED : April 10, 2012  
INVENTOR(S) : Richard A. Gambale et al.

Page 1 of 1

It is certified that error appears in the above-identified patent and that said Letters Patent is hereby corrected as shown below:

On the cover page, in item (63), replace "March 24, 2003" with --March 2, 2001--.

Item (63) should read: Continuation of application No. 10/220,379, filed as application No. PCT/US01/06835 on March 2, 2001, now Pat. No. 7,399,304.

Signed and Sealed this  
Seventeenth Day of July, 2012

David J. Kappos  
*Director of the United States Patent and Trademark Office*